United States Patent
Chen et al.

(10) Patent No.: US 10,100,046 B2
(45) Date of Patent: *Oct. 16, 2018

(54) INHIBITORS OF LYSINE SPECIFIC DEMETHYLASE-1

(71) Applicant: Celgene Quanticel Research, Inc., San Diego, CA (US)

(72) Inventors: Young K. Chen, San Marcos, CA (US); Toufike Kanouni, La Jolla, CA (US); Zhe Nie, San Diego, CA (US); Jeffrey Alan Stafford, San Diego, CA (US); James Marvin Veal, Apex, NC (US)

(73) Assignee: CELGENE QUANTICEL RESEARCH, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/867,397

(22) Filed: Jan. 10, 2018

(65) Prior Publication Data

US 2018/0127408 A1 May 10, 2018

Related U.S. Application Data

(63) Continuation of application No. 15/323,277, filed as application No. PCT/US2015/038345 on Jun. 29, 2015, now Pat. No. 9,902,719.

(60) Provisional application No. 62/020,886, filed on Jul. 3, 2014.

(51) Int. Cl.
| | |
|---|---|
| *C07D 417/14* | (2006.01) |
| *C07D 519/00* | (2006.01) |
| *C07D 417/04* | (2006.01) |
| *C07D 417/06* | (2006.01) |
| *C07D 401/14* | (2006.01) |
| *C07D 471/10* | (2006.01) |
| *C07D 401/04* | (2006.01) |
| *C07D 487/04* | (2006.01) |
| *C07D 471/04* | (2006.01) |

(52) U.S. Cl.
CPC ......... *C07D 417/14* (2013.01); *C07D 401/04* (2013.01); *C07D 401/14* (2013.01); *C07D 417/04* (2013.01); *C07D 417/06* (2013.01); *C07D 471/04* (2013.01); *C07D 471/10* (2013.01); *C07D 487/04* (2013.01); *C07D 519/00* (2013.01)

(58) Field of Classification Search
CPC .. C07D 417/14; C07D 401/04; C07D 401/14; C07D 417/04; C07D 417/06; C07D 471/04; C07D 471/10; C07D 487/04; C07D 519/00

USPC ......................................................... 514/215
See application file for complete search history.

(56) References Cited

U.S. PATENT DOCUMENTS

| | | |
|---|---|---|
| 3,691,177 A | 9/1972 | Bossert et al. |
| 7,618,990 B2 | 11/2009 | Commons et al. |
| 2007/0049619 A1 | 3/2007 | Akahoshi et al. |
| 2008/0269196 A1 | 10/2008 | Briner et al. |

FOREIGN PATENT DOCUMENTS

| | | |
|---|---|---|
| CN | 101258131 A | 9/2008 |
| CN | 101501031 A | 8/2009 |
| JP | 2007-197324 A | 8/2007 |
| WO | 2008021309 A1 | 2/2008 |
| WO | 2008112498 A1 | 9/2008 |
| WO | 2011/130515 A1 | 10/2011 |
| WO | 2012/009475 A1 | 1/2012 |
| WO | 2013/132380 A1 | 9/2013 |
| WO | 2015173324 A1 | 11/2015 |

OTHER PUBLICATIONS

International Search Report and Written Opinion cited, dated Oct. 27, 2107, in related Singapore Appln. No. 11201610975R based on International Patent Application No. PCT/US2015/038345, filed Jun. 29, 2015.
International Search Report and Written Opinion cited, dated Sep. 30, 2015, in related International Patent Application No. PCT/US2015/038345, filed Jun. 29, 2015.
Cancer [online], [retrieved on Jul. 6, 2007] Retrieved from the Internet, URL; http://www.nlm.nih.gov/medlineeplus/cancer.html.
Lala et al., Role of nitric oxide in tumor prrogression: Lessons from experimental tumors, Cancer and Metastasis Reviews (1998), 17, 91-106.
Golub et al., Molecular Classification of Cancer: Class Discovery and Class Prediction by Gene Expression Monitoring , Science (1999), vol. 286, 531-537.
Partial Supplementary European Search Report cited, dated Jan. 26, 2018, in related European Appln. No. 15814038.4, filed Jan. 10, 2017, based on International Patent Application No. PCT/US2015/038345, filed Jun. 29, 2015.
First Office Action dated Feb. 24, 2018 by the State Intellectual Property Office of China, pp. 1-11.

*Primary Examiner* — Kristin A Vajda
(74) *Attorney, Agent, or Firm* — Wiley Rein LLP

(57) ABSTRACT

The present invention relates generally to compositions and methods for treating cancer and neoplastic disease. Provided herein are substituted heterocyclic derivative compounds and pharmaceutical compositions comprising said compounds. The subject compounds and compositions are useful for inhibition of lysine specific demethylase-1. Furthermore, the subject compounds and compositions are useful for the treatment of cancer, such as prostate cancer, breast cancer, bladder cancer, lung cancer and/or melanoma and the like.

8 Claims, No Drawings

INHIBITORS OF LYSINE SPECIFIC DEMETHYLASE-1

CROSS-REFERENCE

This application is a continuation of U.S. patent application Ser. No. 15/323,277, filed Dec. 30, 2016, which is a 371 of International Patent Application No. PCT/US2015/038345, filed Jun. 29, 2015, which claims the benefit of U.S. Provisional Application No. 62/020,886, filed Jul. 3, 2014, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted heterocyclic derivative compounds and pharmaceutical compositions comprising said compounds. The subject compounds and compositions are useful for inhibition lysine specific demethylase-1 (LSD-1). Furthermore, the subject compounds and compositions are useful for the treatment of cancer, such as prostate cancer, breast cancer, bladder cancer, lung cancer and/or melanoma and the like. The substituted heterocyclic derivative compounds described herein are based upon a central heterocyclic ring system, such as a thiazole or pyrimidinone, or the like. Said central heterocyclic ring system is further substituted with additional substituents, such as for example, a 4-cyanophenyl group and a heterocyclyl group.

One embodiment provides a compound having the structure of Formula (I), or a pharmaceutically acceptable salt thereof,

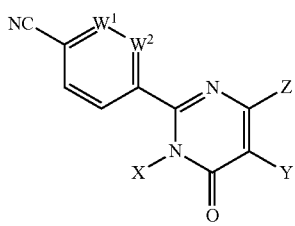

(I)

wherein,

W$^1$ and W$^2$ are independently chosen from N, C—H, or C—F;

X is chosen from hydrogen, optionally substituted alkyl, optionally substituted cycloalkyl, optionally substituted heterocyclyl, optionally substituted cycloalkylalkyl, optionally substituted heterocyclylalkyl, optionally substituted aralkyl, optionally substituted heteroarylalkyl, optionally substituted aryl, or optionally substituted heteroaryl;

Y is chosen from hydrogen, halogen, optionally substituted alkyl, or optionally substituted cycloalkylalkyl; and Z is chosen from an optionally substituted group chosen from N-heterocyclyl, —O— heterocyclylalkyl, —N(H)-heterocyclylalkyl, —N(H)-alkyl, —N(Me)-alkyl, or —N(Me)-heterocyclylalkyl.

One embodiment provides a compound having the structure of Formula (II), or a pharmaceutically acceptable salt thereof,

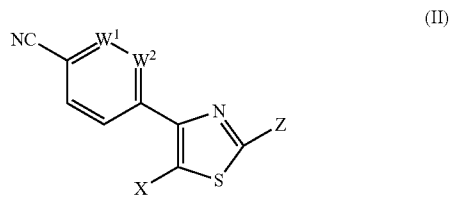

(II)

wherein,

W$^1$ and W$^2$ are independently chosen from N, C—H, or C—F;

X is chosen from hydrogen, optionally substituted alkyl, optionally substituted alkoxy, optionally substituted alkylamino, optionally substituted alkynyl, optionally substituted cycloalkylalkynyl, optionally substituted (cycloalkylalkyl)alkynyl, optionally substituted heterocyclylalkynyl, optionally substituted (heterocyclylalkyl)alkynyl, optionally substituted aryl, or optionally substituted heteroaryl; and Z is chosen from an optionally substituted group chosen from N-heterocyclyl, —C(O)—N— heterocyclyl, —O-heterocyclylalkyl, —N(H)-heterocyclylalkyl, —N(H)-alkyl, —N(Me)-alkyl, or —N(Me)-heterocyclylalkyl.

One embodiment provides a pharmaceutical composition comprising a compound of Formula (I), or a pharmaceutically acceptable salt thereof, and a pharmaceutically acceptable excipient.

One embodiment provides a method of regulating gene transcription in a cell comprising inhibiting lysine-specific demethylase 1 activity by exposing the lysine-specific demethylase 1 enzyme to a compound of Formula (I).

One embodiment provides a method of treating cancer in a patient in need thereof, comprising administering to the patient a compound of Formula (I), or a pharmaceutically acceptable salt thereof.

One embodiment provides a pharmaceutical composition comprising a compound of Formula (II), or a pharmaceutically acceptable salt thereof, and a pharmaceutically acceptable excipient.

One embodiment provides a method of regulating gene transcription in a cell comprising inhibiting lysine-specific demethylase 1 activity by exposing the lysine-specific demethylase 1 enzyme to a compound of Formula (II).

One embodiment provides a method of treating cancer in a patient in need thereof, comprising administering to the patient a compound of Formula (II), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O— alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —OC(O)—$N(R^a)_2$, —$N(R^a)C(O)R^a$, —$N(R^a)S(O)_tR^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkynyl" refers to a radical of the formula —R$^c$-carbocyclyl where R$^c$ is an alkynylene chain as defined above. The alkynylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

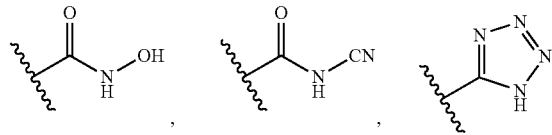

-continued

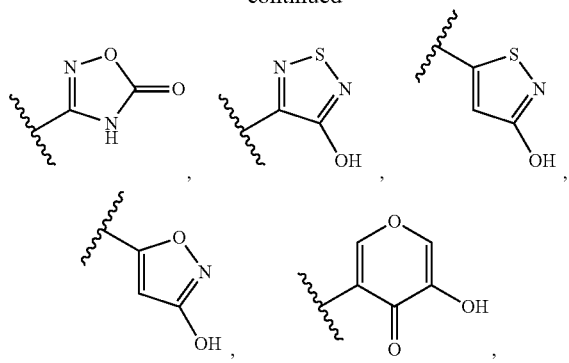

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O) $R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where R is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

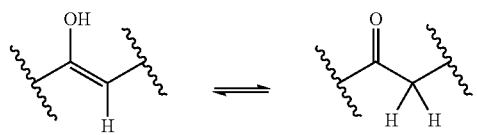

-continued

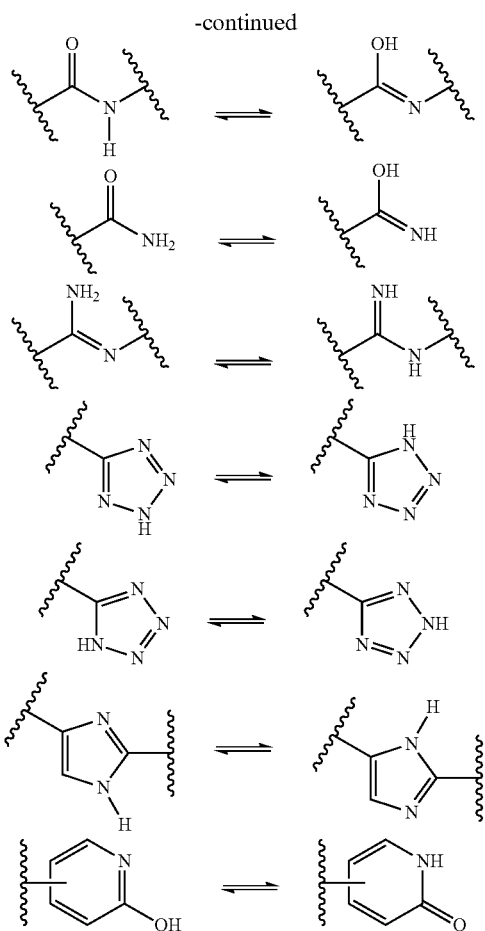

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted heterocyclic derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Heterocyclic Derivative Compounds

Substituted heterocyclic derivative compounds are described herein that are lysine specific demethylase-1 inhibitors. These compounds, and compositions comprising these compounds, are useful for the treatment of cancer and neoplastic disease. The compounds described herein are useful for treating prostate cancer, breast cancer, bladder cancer, lung cancer and/or melanoma and the like.

One embodiment provides a compound having the structure of Formula (I), or a pharmaceutically acceptable salt thereof,

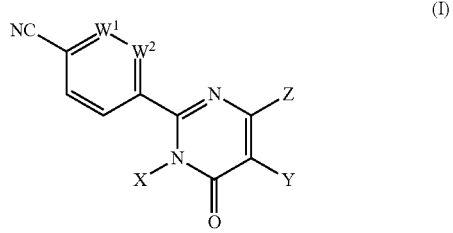

(I)

wherein, $W^1$ and $W^2$ are independently chosen from N, C—H, or C—F;

X is chosen from hydrogen, optionally substituted alkyl, optionally substituted cycloalkyl, optionally substituted heterocyclyl, optionally substituted cycloalkylalkyl, optionally substituted heterocyclylalkyl, optionally substituted aralkyl, optionally substituted heteroarylalkyl, optionally substituted aryl, or optionally substituted heteroaryl;

Y is chosen from hydrogen, halogen, optionally substituted alkyl, or optionally substituted cycloalkylalkyl; and Z is chosen from an optionally substituted group chosen from N-heterocyclyl, —O— heterocyclylalkyl, —N(H)-heterocyclylalkyl, —N(H)-alkyl, —N(Me)-alkyl, or —N(Me)-heterocyclylalkyl.

Another embodiment provides the compound or pharmaceutically acceptable salt of Formula (I), wherein $W^2$ is C—H. Another embodiment provides the compound or pharmaceutically acceptable salt of Formula (I), wherein $W^1$ is C—F. Another embodiment provides the compound or pharmaceutically acceptable salt of Formula (I), wherein $W^1$ is C—H. Another embodiment provides the compound or pharmaceutically acceptable salt of Formula (I), wherein $W^1$ is N.

Another embodiment provides the compound or pharmaceutically acceptable salt of Formula (I), wherein X is optionally substituted aryl, or optionally substituted heteroaryl.

Another embodiment provides the compound or pharmaceutically acceptable salt of Formula (I), wherein X is optionally substituted aryl. Another embodiment provides the compound or pharmaceutically acceptable salt of Formula (I), wherein X is optionally substituted aryl, and the optionally substituted aryl is an optionally substituted phenyl.

Another embodiment provides the compound or pharmaceutically acceptable salt of Formula (I), wherein X is optionally substituted heteroaryl. Another embodiment provides the compound or pharmaceutically acceptable salt of Formula (I), wherein X is optionally substituted heteroaryl, and the optionally substituted heteroaryl is chosen from an optionally substituted pyridinyl, optionally substituted pyrimidinyl, optionally substituted pyrazinyl, optionally substituted pyrazolyl, optionally substituted indazolyl, optionally substituted azaindazolyl, optionally substituted isoindazolyl, optionally substituted indolyl, or optionally substituted azaindolyl.

Another embodiment provides the compound or pharmaceutically acceptable salt of Formula (I), wherein Z is an optionally substituted —O-heterocyclylalkyl. Another embodiment provides the compound or pharmaceutically acceptable salt of Formula (I), wherein Z is an optionally substituted —O-heterocyclylalkyl, the heterocyclylalkyl group has the formula —$R^c$-heterocyclyl, and the $R^c$ is an optionally substituted $C_1$-$C_3$ alkylene chain. Another embodiment provides the compound or pharmaceutically acceptable salt of Formula (I), wherein Z is an optionally substituted —O-heterocyclylalkyl, the heterocyclylalkyl group has the formula —$R^c$-heterocyclyl, and the $R^c$ is an optionally substituted $C_1$ alkylene chain. Another embodiment provides the compound or pharmaceutically acceptable salt of Formula (I), wherein Z is an optionally substituted —O-heterocyclylalkyl, the heterocyclylalkyl group has the formula —$R^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (I), wherein Z is an optionally substituted —N(H)-heterocyclylalkyl. Another embodiment provides the compound or pharmaceutically acceptable salt of Formula (I), wherein Z is an optionally substituted —N(H)-heterocyclylalkyl, the heterocyclylalkyl group has the formula —$R^c$-heterocyclyl, and the $R^c$ is an optionally substituted $C_1$-$C_3$ alkylene chain. Another embodiment provides the compound or pharmaceutically acceptable salt of Formula (I), wherein Z is an optionally substituted —N(H)-heterocyclylalkyl, the heterocyclylalkyl group has the formula —$R^c$-heterocyclyl, and the $R^c$ is an optionally substituted $C_1$ alkylene chain. Another embodiment provides the compound or pharmaceutically acceptable salt of Formula (I), wherein Z is an optionally substituted —N(H)-heterocyclylalkyl, the heterocyclylalkyl group has the formula —$R^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (I), wherein Z is an optionally substituted —N(Me)-heterocyclylalkyl. Another embodiment provides the compound or pharmaceutically acceptable salt of Formula (I), wherein Z is an optionally substituted —N(Me)-heterocyclylalkyl, the heterocyclylalkyl group has the formula —$R^c$-heterocyclyl, and the $R^c$ is an optionally substituted $C_1$-$C_3$ alkylene chain. Another embodiment provides the compound or pharmaceutically acceptable salt of Formula (I), wherein Z is an optionally substituted —N(Me)-heterocyclylalkyl, the heterocyclylalkyl group has the formula —$R^c$-heterocyclyl, and the $R^c$ is an optionally substituted $C_1$ alkylene chain. Another embodiment provides the compound or pharmaceutically acceptable salt of Formula (I), wherein Z is an optionally substituted —N(Me)-heterocyclylalkyl, the heterocyclylalkyl group has the formula —$R^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (I), wherein Z is an optionally substituted N-heterocyclyl. Another embodiment provides the compound or pharmaceutically acceptable salt of Formula (I), wherein Z is an optionally substituted N-heterocyclyl, and the optionally substituted N-heterocyclyl is a 4-, 5-, 6-, or 7-membered N-heterocyclyl. Another embodiment provides the compound or pharmaceutically acceptable salt of Formula (I), wherein Z is an optionally substituted N-heterocyclyl, and the optionally substituted N-heterocyclyl is a 6-membered N-heterocyclyl. Another embodiment provides the compound or pharmaceutically acceptable salt of Formula (I), wherein Z is an optionally substituted N-heterocyclyl, and the optionally substituted N-heterocyclyl is an optionally substituted piperidine.

Another embodiment provides the compound or pharmaceutically acceptable salt of Formula (I), wherein Z is an optionally substituted N-heterocyclyl, the optionally substituted N-heterocyclyl is an optionally substituted piperidine, and the optionally substituted piperidine is an optionally substituted 4-aminopiperidine.

Another embodiment provides the compound or pharmaceutically acceptable salt of Formula (I), wherein Y is hydrogen. Another embodiment provides the compound or pharmaceutically acceptable salt of Formula (I), wherein Y is halogen. Another embodiment provides the compound or pharmaceutically acceptable salt of Formula (I), wherein Y is optionally substituted cycloalkylalkyl.

Another embodiment provides the compound or pharmaceutically acceptable salt of Formula (I), wherein Y is optionally substituted alkyl. Another embodiment provides the compound or pharmaceutically acceptable salt of Formula (I), wherein Y is optionally substituted alkyl, and the optionally substituted alkyl is an optionally substituted $C_1$-$C_3$ alkyl. Another embodiment provides the compound or pharmaceutically acceptable salt of Formula (I), wherein Y is optionally substituted alkyl, and the optionally substituted alkyl is an optionally substituted $C_1$ alkyl. Another embodiment provides the compound or pharmaceutically acceptable salt of Formula (I), wherein Y is optionally substituted alkyl, and the optionally substituted alkyl is a methyl group.

One embodiment provides a compound having the structure of Formula (II), or a pharmaceutically acceptable salt thereof,

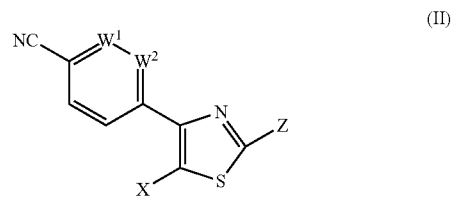

(II)

wherein, $W^1$ and $W^2$ are independently chosen from N, C—H, or C—F;

X is chosen from hydrogen, optionally substituted alkyl, optionally substituted alkoxy, optionally substituted alkylamino, optionally substituted alkynyl, optionally substituted cycloalkylalkynyl, optionally substituted (cycloalkylalkyl)alkynyl, optionally substituted heterocyclylalkynyl, optionally substituted (heterocyclylalkyl)alkynyl, optionally substituted aryl, or optionally substituted heteroaryl; and Z is chosen from an optionally substituted group chosen from N-heterocyclyl, —C(O)—N— heterocyclyl, —O-heterocyclylalkyl, —N(H)-heterocyclylalkyl, —N(H)-alkyl, —N(Me)-alkyl, or —N(Me)-heterocyclylalkyl.

Another embodiment provides the compound or pharmaceutically acceptable salt of Formula (II), wherein $W^2$ is C—H. Another embodiment provides the compound or pharmaceutically acceptable salt of Formula (II), wherein $W^1$ is C—F. Another embodiment provides the compound or pharmaceutically acceptable salt of Formula (II), wherein $W^1$ is C—H. Another embodiment provides the compound or pharmaceutically acceptable salt of Formula (II), wherein $W^1$ is N.

Another embodiment provides the compound or pharmaceutically acceptable salt of Formula (II), wherein X is optionally substituted aryl, or optionally substituted heteroaryl.

Another embodiment provides the compound or pharmaceutically acceptable salt of Formula (II), wherein X is optionally substituted aryl. Another embodiment provides the compound or pharmaceutically acceptable salt of Formula (II), wherein X is optionally substituted aryl, and the optionally substituted aryl is an optionally substituted phenyl.

Another embodiment provides the compound or pharmaceutically acceptable salt of Formula (II), wherein X is optionally substituted heteroaryl. Another embodiment provides the compound or pharmaceutically acceptable salt of Formula (II), wherein X is optionally substituted heteroaryl, and the optionally substituted heteroaryl is chosen from an optionally substituted pyridinyl, optionally substituted pyrimidinyl, optionally substituted pyrazinyl, optionally substituted pyrazolyl, optionally substituted indazolyl, optionally substituted azaindazolyl, optionally substituted isoindazolyl, optionally substituted indolyl, optionally substituted azaindolyl, optionally substituted benzimidazolyl, or optionally substituted azabenzimidazolyl.

Another embodiment provides the compound or pharmaceutically acceptable salt of Formula (II), wherein X is optionally substituted alkynyl, optionally substituted cycloalkylalkynyl, optionally substituted (cycloalkylalkyl)alkynyl, optionally substituted heterocyclylalkynyl, or optionally substituted (heterocyclylalkyl)alkynyl.

Another embodiment provides the compound or pharmaceutically acceptable salt of Formula (II), wherein Z is an optionally substituted —O-heterocyclylalkyl. Another embodiment provides the compound or pharmaceutically acceptable salt of Formula (II), wherein Z is an optionally substituted —O-heterocyclylalkyl, the heterocyclylalkyl group has the formula —R$^c$-heterocyclyl, and the R$^c$ is an optionally substituted C$_1$-C$_3$ alkylene chain. Another embodiment provides the compound or pharmaceutically acceptable salt of Formula (II), wherein Z is an optionally substituted —O-heterocyclylalkyl, the heterocyclylalkyl group has the formula —R$^c$-heterocyclyl, and the R$^c$ is an optionally substituted C$_1$ alkylene chain. Another embodiment provides the compound or pharmaceutically acceptable salt of Formula (II), wherein Z is an optionally substituted —O-heterocyclylalkyl, the heterocyclylalkyl group has the formula —R$^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (II), wherein Z is an optionally substituted —N(H)-heterocyclylalkyl. Another embodiment provides the compound or pharmaceutically acceptable salt of Formula (II), wherein Z is an optionally substituted —N(H)-heterocyclylalkyl, the heterocyclylalkyl group has the formula —R$^c$-heterocyclyl, and the R$^c$ is an optionally substituted C$_1$-C$_3$ alkylene chain. Another embodiment provides the compound or pharmaceutically acceptable salt of Formula (II), wherein Z is an optionally substituted —N(H)-heterocyclylalkyl, the heterocyclylalkyl group has the formula —R$^c$-heterocyclyl, and the R$^c$ is an optionally substituted C$_1$ alkylene chain. Another embodiment provides the compound or pharmaceutically acceptable salt of Formula (II), wherein Z is an optionally substituted —N(H)-heterocyclylalkyl, the heterocyclylalkyl group has the formula —R$^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (II), wherein Z is an optionally substituted —N(Me)-heterocyclylalkyl. Another embodiment provides the compound or pharmaceutically acceptable salt of Formula (II), wherein Z is an optionally substituted —N(Me)-heterocyclylalkyl, the heterocyclylalkyl group has the formula —R$^c$-heterocyclyl, and the R$^c$ is an optionally substituted C$_1$-C$_3$ alkylene chain. Another embodiment provides the compound or pharmaceutically acceptable salt of Formula (II), wherein Z is an optionally substituted —N(Me)-heterocyclylalkyl, the heterocyclylalkyl group has the formula —R$^c$-heterocyclyl, and the R$^c$ is an optionally substituted C$_1$ alkylene chain. Another embodiment provides the compound or pharmaceutically acceptable salt of Formula (II), wherein Z is an optionally substituted —N(Me)-heterocyclylalkyl, the heterocyclylalkyl group has the formula —R$^c$-heterocyclyl, and the heterocyclyl is an optionally substituted nitrogen-containing 4-, 5-, 6-, or 7-membered heterocyclyl.

Another embodiment provides the compound or pharmaceutically acceptable salt of Formula (II), wherein Z is an optionally substituted N-heterocyclyl. Another embodiment provides the compound or pharmaceutically acceptable salt of Formula (II), wherein Z is an optionally substituted N-heterocyclyl, and the optionally substituted N-heterocyclyl is a 4-, 5-, 6-, or 7-membered N-heterocyclyl. Another embodiment provides the compound or pharmaceutically acceptable salt of Formula (II), wherein Z is an optionally substituted N-heterocyclyl, and the optionally substituted N-heterocyclyl is a 6-membered N-heterocyclyl.

Another embodiment provides the compound or pharmaceutically acceptable salt of Formula (II), wherein Z is an optionally substituted N-heterocyclyl, and the optionally substituted N-heterocyclyl is an optionally substituted piperidine. Another embodiment provides the compound or pharmaceutically acceptable salt of Formula (II), wherein Z is an optionally substituted N-heterocyclyl, the optionally substituted N-heterocyclyl is an optionally substituted piperidine, and the optionally substituted piperidine is an optionally substituted 4-aminopiperidine.

Another embodiment provides the compound or pharmaceutically acceptable salt of Formula (II), wherein Z is an optionally substituted —C(O)—N-heterocyclyl. Another embodiment provides the compound or pharmaceutically acceptable salt of Formula (II), wherein Z is an optionally substituted —C(O)—N-heterocyclyl, and the optionally substituted N-heterocyclyl is an optionally substituted piperidine.

In some embodiments, the substituted heterocyclic derivative compound described herein has the structure provided in Table 1.

TABLE 1

| Chemical Synthesis Example | Structure | Name |
|---|---|---|
| 1 | 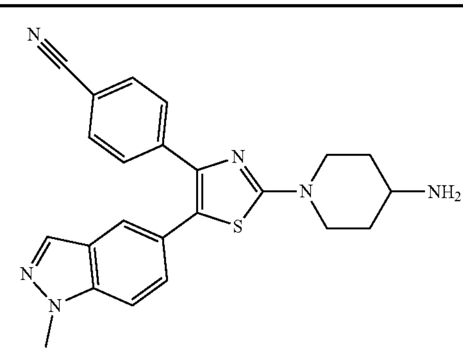 | 4-[2-(4-aminopiperidin-1-yl)-5-(1-methyl-1H-indazol-5-yl)-1,3-thiazol-4-yl]benzonitrile |

TABLE 1-continued
| Chemical Synthesis Example | Structure | Name |
|---|---|---|
| 2 | 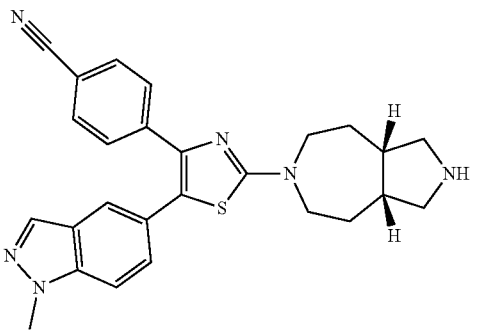 [SMILES: Cn1ncc2cc(-c3sc(N4CC[C@@H]5CNC[C@@H]5CC4)nc3-c3ccc(C#N)cc3)ccc21] | cis-4-(2-{decahydropyrrolo[3,4-d]azepin-6-yl}-5-(1-methyl-1H-indazol-5-yl)-1,3-thiazol-4-yl)benzonitrile |
| 3 | 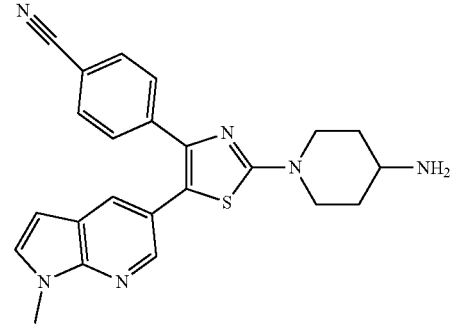 [SMILES: Cn1ccc2cc(-c3sc(N4CCC(N)CC4)nc3-c3ccc(C#N)cc3)cnc21] | 4-[2-(4-aminopiperidin-1-yl)-5-{1-methyl-1H-pyrrolo[2,3-b]pyridin-5-yl}-1,3-thiazol-4-yl]benzonitrile |
| 4 | 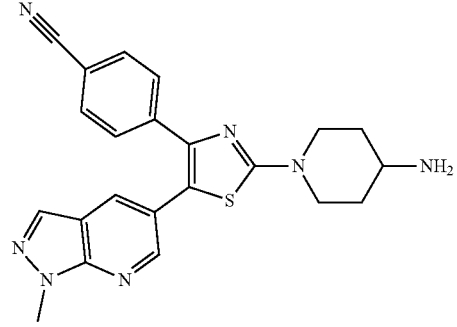 [SMILES: Cn1ncc2cc(-c3sc(N4CCC(N)CC4)nc3-c3ccc(C#N)cc3)cnc21] | 4-[2-(4-aminopiperidin-1-yl)-5-{1-methyl-1H-pyrazolo[3,4-b]pyridin-5-yl}-1,3-thiazol-4-yl]benzonitrile |
| 5 | 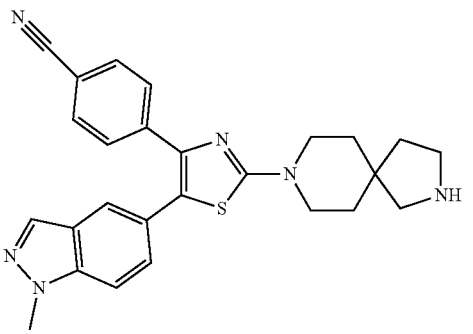 [SMILES: Cn1ncc2cc(-c3sc(N4CCC5(CCNC5)CC4)nc3-c3ccc(C#N)cc3)ccc21] | 4-(2-{2,8-diazaspiro[4.5]decan-8-yl}-5-(1-methyl-1H-indazol-5-yl)-1,3-thiazol-4-yl)benzonitrile |

TABLE 1-continued

| Chemical Synthesis Example | Structure | Name |
|---|---|---|
| 6 | 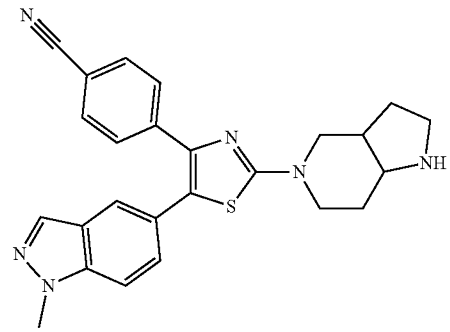 [SMILES: Cn1ncc2cc(-c3sc(N4CCC5NCCC5C4)nc3-c3ccc(C#N)cc3)ccc21] | 4-[5-(1-methyl-1H-indazol-5-yl)-2-{octahydro-1H-pyrrolo[3,2-c]pyridin-5-yl}-1,3-thiazol-4-yl]benzonitrile |
| 7 | 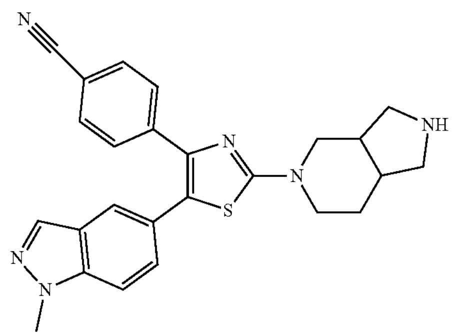 [SMILES: Cn1ncc2cc(-c3sc(N4CCC5CNCC5C4)nc3-c3ccc(C#N)cc3)ccc21] | 4-[5-(1-methyl-1H-indazol-5-yl)-2-{octahydro-1H-pyrrolo[3,4-c]pyridin-5-yl}-1,3-thiazol-4-yl]benzonitrile |
| 8 | 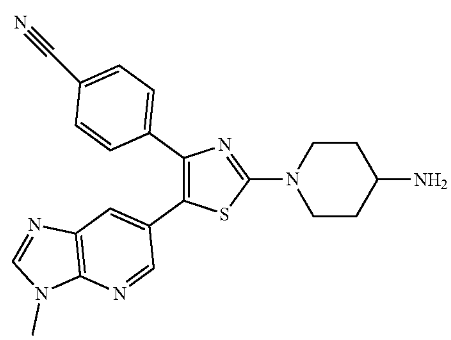 [SMILES: Cn1cnc2cc(-c3sc(N4CCC(N)CC4)nc3-c3ccc(C#N)cc3)cnc21] | 4-[2-(4-aminopiperidin-1-yl)-5-(1-methyl-1H-1,3-benzodiazol-5-yl)-1,3-thiazol-4-yl]benzonitrile |
| 9 | 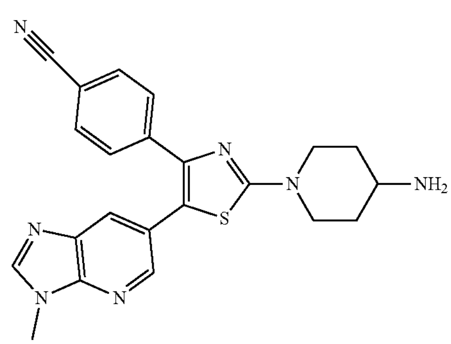 [SMILES: Cn1cnc2cc(-c3sc(N4CCC(N)CC4)nc3-c3ccc(C#N)cc3)cnc21] | 4-[2-(4-aminopiperidin-1-yl)-5-{3-methyl-3H-imidazo[4,5-b]pyridin-6-yl)-1,3-thiazol-4-yl]benzonitrile |

TABLE 1-continued

| Chemical Synthesis Example | Structure | Name |
|---|---|---|
| 10 | 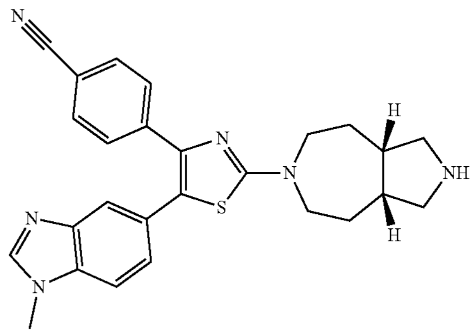 [SMILES: Cn1cnc2cc(-c3sc(N4CC[C@@H]5CNC[C@@H]5CC4)nc3-c3ccc(C#N)cc3)ccc21] | cis-4-(2-{decahydropyrrolo[3,4-d]azepin-6-yl}-5-(1-methyl-1H-1,3-benzodiazol-5-yl)-1,3-thiazol-4-yl)benzonitrile |
| 11 | 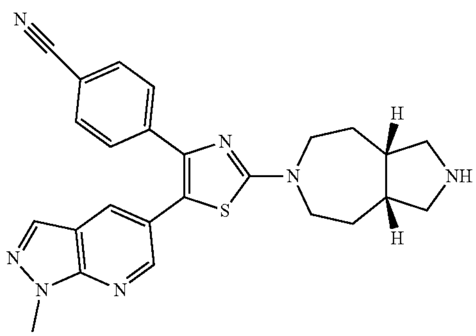 [SMILES: Cn1ncc2cc(-c3sc(N4CC[C@@H]5CNC[C@@H]5CC4)nc3-c3ccc(C#N)cc3)cnc21] | cis-4-(2-{decahydropyrrolo[3,4-d]azepin-6-yl}-5-{1-methyl-1H-pyrazolo[3,4-b]pyridin-5-yl}-1,3-thiazol-4-yl)benzonitrile |
| 12 | 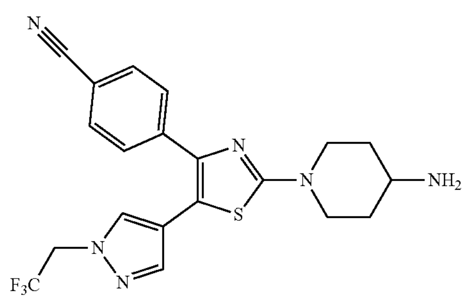 [SMILES: N#Cc1ccc(-c2nc(N3CCC(N)CC3)sc2-c2cnn(CC(F)(F)F)c2)cc1] | 4-[2-(4-aminopiperidin-1-yl)-5-[1-(2,2,2-trifluoroethyl)-1H-pyrazol-4-yl]-1,3-thiazol-4-yl]benzonitrile |
| 13 | 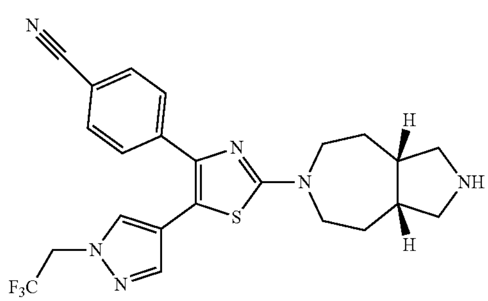 [SMILES: N#Cc1ccc(-c2nc(N3CC[C@@H]4CNC[C@@H]4CC3)sc2-c2cnn(CC(F)(F)F)c2)cc1] | 4-(2-{decahydropyrrolo[3,4-d]azepin-6-yl}-5-[1-(2,2,2-trifluoroethyl)-1H-pyrazol-4-yl]-1,3-thiazol-4-yl)benzonitrile |

TABLE 1-continued

| Chemical Synthesis Example | Structure | Name |
|---|---|---|
| 14 | 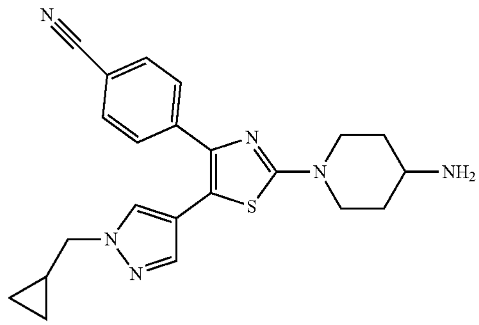 [SMILES: N#Cc1ccc(-c2nc(N3CCC(N)CC3)sc2-c2cnn(CC3CC3)c2)cc1] | 4-[2-(4-aminopiperidin-1-yl-5[1-(cyclopropylmethyl)-1H-pyrazol-4-yl]-1,3-thiazol-4-yl]benzonitrile |
| 15 | 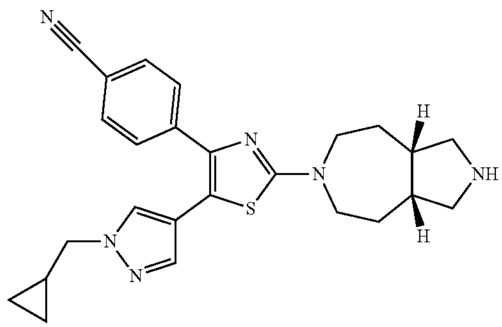 [SMILES: N#Cc1ccc(-c2nc(N3CC[C@@H]4CNC[C@@H]4CC3)sc2-c2cnn(CC3CC3)c2)cc1] | 4-{5-[1-(cyclopropylmethyl)-1H-pyrazol-4-yl]-2-{decahydropyrrolo[3,4-d]azepin-6-yl}-1,3-thiazol-4-yl]benzonitrile |
| 16 | 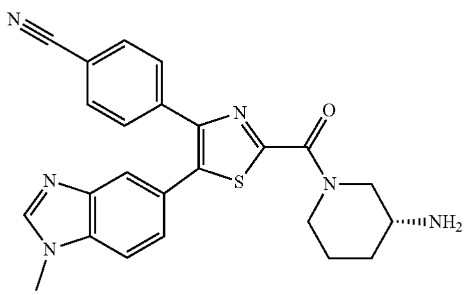 [SMILES: Cn1cnc2cc(-c3sc(C(=O)N4CCC[C@@H](N)C4)nc3-c3ccc(C#N)cc3)ccc21] | 4-{2-[(3R)-3-aminopiperidine-1-carbonyl]-5-(1-methyl-1H-1,3-benzodiazol-5-yl)-1,3-thiazol-4-yl}benzonitrile |
| 17 | 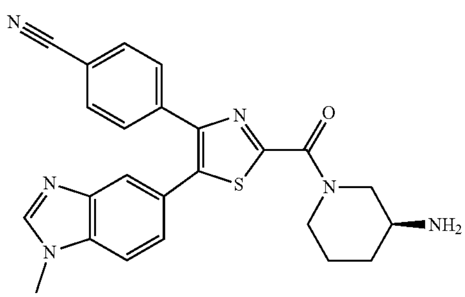 [SMILES: Cn1cnc2cc(-c3sc(C(=O)N4CCC[C@H](N)C4)nc3-c3ccc(C#N)cc3)ccc21] | 4-{2-[(3S)-3-aminopiperidine-1-carbonyl]-5-(1-methyl-1H-1,3-benzodiazol-5-yl)-1,3-thiazol-4-yl}benzonitrile |
| 18 | 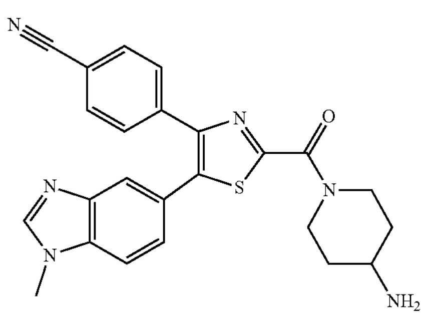 [SMILES: Cn1cnc2cc(-c3sc(C(=O)N4CCC(N)CC4)nc3-c3ccc(C#N)cc3)ccc21] | 4-[2-(4-aminopiperidine-1-carbonyl)-5-(1-methyl-1H-1,3-benzodiazol-5-yl)-1,3-thiazol-4-yl]benzonitrile |

TABLE 1-continued

| Chemical Synthesis Example | Structure | Name |
|---|---|---|
| 19 | 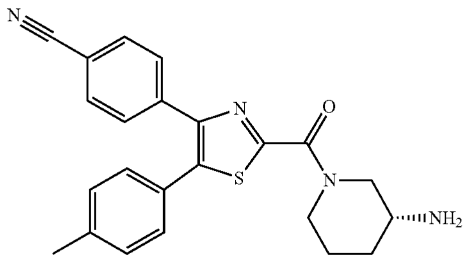 [SMILES: Cc1ccc(-c2sc(C(=O)N3CCC[C@@H](N)C3)nc2-c2ccc(C#N)cc2)cc1] | 4-{2-[(3R)-3-aminopiperidine-1-carbonyl]-5-(4-methylphenyl)-1,3-thiazol-4-yl}benzonitrile |
| 20 | 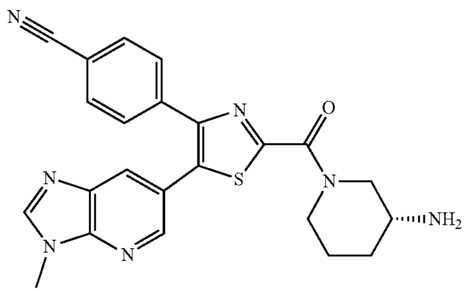 [SMILES: Cn1cnc2cc(-c3sc(C(=O)N4CCC[C@@H](N)C4)nc3-c3ccc(C#N)cc3)cnc21] | 4-{2-[(3R)-3-aminopiperidine-1-carbonyl]-5-{3-methyl-3H-imidazo[4,5-b]pyridin-6-yl}-1,3-thiazol-4-yl}benzonitrile |
| 21 | 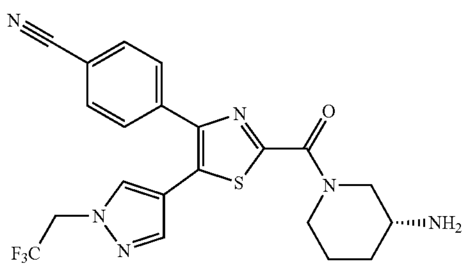 [SMILES: N#Cc1ccc(-c2nc(C(=O)N3CCC[C@@H](N)C3)sc2-c2cnn(CC(F)(F)F)c2)cc1] | 4-{2-[(3R)-3-aminopiperidine-1-carbonyl]-5-[1-(2,2,2-trifluoroethyl)-1H-pyrazol-4-yl]-1,3-thiazol-4-yl}benzonitrile |
| 22 | 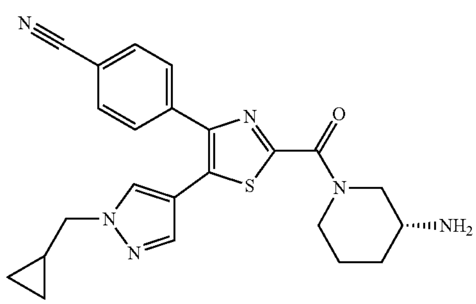 [SMILES: N#Cc1ccc(-c2nc(C(=O)N3CCC[C@@H](N)C3)sc2-c2cnn(CC3CC3)c2)cc1] | 4-{2-[(3R)-3-aminopiperidine-1-carbonyl]-5-[1-(cyclopropylmethyl)-1H-pyrazol-4-yl]-1,3-thiazol-4-yl}benzonitrile |
| 23 | 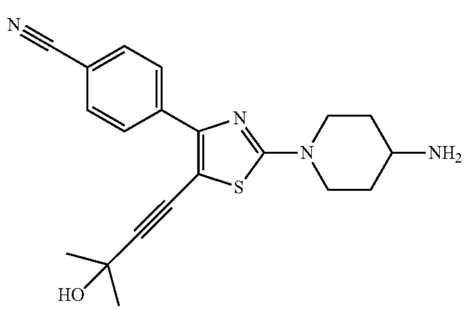 [SMILES: CC(C)(O)C#Cc1sc(N2CCC(N)CC2)nc1-c1ccc(C#N)cc1] | 4-[2-(4-aminopiperidin-1-yl)-5-(3-hydroxy-3-methylbut-1-yn-1-yl)-1,3-thiazol-4-yl]benzonitrile |

TABLE 1-continued

| Chemical Synthesis Example | Structure | Name |
|---|---|---|
| 24 | 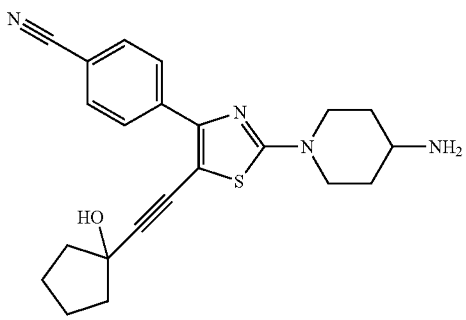 [SMILES: N#Cc1ccc(-c2nc(N3CCC(N)CC3)sc2C#CC2(O)CCCC2)cc1] | 4-[2-(4-aminopiperidin-1-yl)-5-(3-hydroxy-3-cyclopentylprop-1-yn-1-yl)-1,3-thiazol-4-yl]benzonitrile |
| 25 | 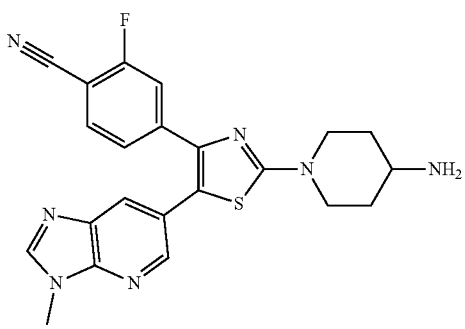 [SMILES: Cn1cnc2cc(-c3sc(N4CCC(N)CC4)nc3-c3ccc(C#N)c(F)c3)cnc21] | 4-[2-(4-aminopiperidin-1-yl)-5-{3-methyl-3H-imidazo[4,5-b]pyridin-6-yl}-1,3-thiazol-4-yl]-2-fluorobenzonitrile |
| 26 | 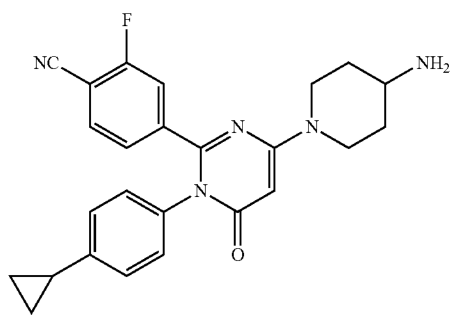 [SMILES: N#Cc1ccc(-c2nc(N3CCC(N)CC3)cc(=O)n2-c2ccc(C3CC3)cc2)cc1F] | 4-[4-(4-aminopiperidin-1-yl)-1-(4-cyclopropylphenyl)-6-oxopyrimidin-2-yl]-2-fluorobenzonitrile |
| 27 | 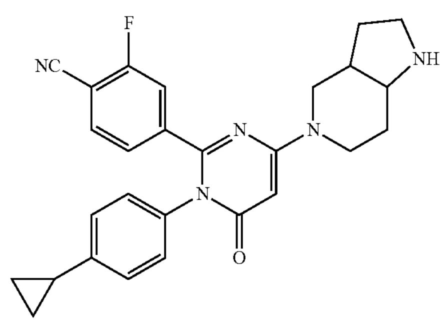 [SMILES: N#Cc1ccc(-c2nc(N3CCC4NCCC4C3)cc(=O)n2-c2ccc(C3CC3)cc2)cc1F] | 4-[4-(1,2,3,3a,4,6,7,7a-octahydropyrrolo[3,2-c]pyridin-5-yl)-1-(4-cyclopropylphenyl)-6-oxopyrimidin-2-yl]-2-fluorobenzonitrile |

TABLE 1-continued

| Chemical Synthesis Example | Structure | Name |
|---|---|---|
| 28 | 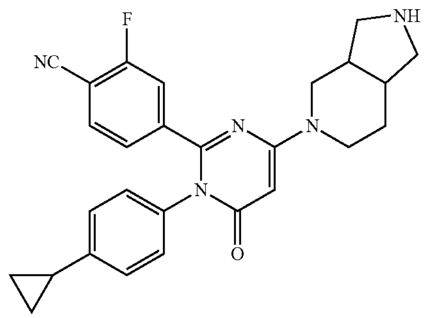 [SMILES: N#Cc1ccc(-c2nc(N3CCC4CNCC4C3)cc(=O)n2-c2ccc(C3CC3)cc2)cc1F] | 4-[4-(1,2,3,3a,4,6,7,7a-octahydropyrrolo[3,4-c]pyridin-5-yl)-1-(4-cyclopropylphenyl)-6-oxopyrimidin-2-yl]-2-fluorobenzonitrile |
| 29 | 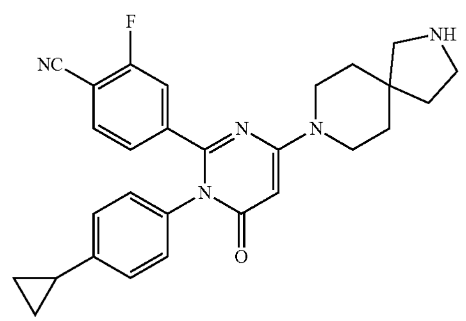 [SMILES: N#Cc1ccc(-c2nc(N3CCC4(CCNC4)CC3)cc(=O)n2-c2ccc(C3CC3)cc2)cc1F] | 4-[1-(4-cyclopropylphenyl)-4-(2,8-diazaspiro[4.5]decan-8-yl)-6-oxopyrimidin-2-yl]-2-fluorobenzonitrile |
| 30 | 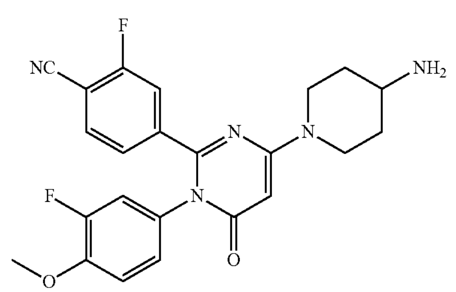 [SMILES: COc1ccc(-n2c(-c3ccc(C#N)c(F)c3)nc(N3CCC(N)CC3)cc2=O)cc1F] | 4-[4-(4-aminopiperidin-1-yl)-1-(3-fluoro-4-methoxyphenyl)-6-oxopyrimidin-2-yl]-2-fluorobenzonitrile |
| 31 | 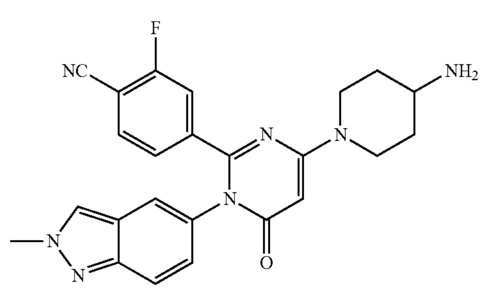 [SMILES: Cn1cc2cc(-n3c(-c4ccc(C#N)c(F)c4)nc(N4CCC(N)CC4)cc3=O)ccc2n1] | 4-[4-(4-aminopiperidin-1-yl)-1-(2-methylindazol-5-yl)-6-oxopyrimidin-2-yl]-2-fluorobenzonitrile |
| 32 | 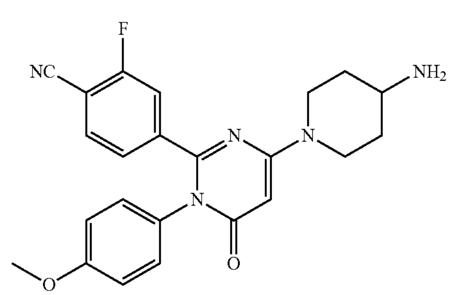 [SMILES: COc1ccc(-n2c(-c3ccc(C#N)c(F)c3)nc(N3CCC(N)CC3)cc2=O)cc1] | 4-[4-(4-aminopiperidin-1-yl)-1-(4-methoxyphenyl)-6-oxopyrimidin-2-yl]-2-fluorobenzonitrile |

TABLE 1-continued

| Chemical Synthesis Example | Structure | Name |
|---|---|---|
| 33 | 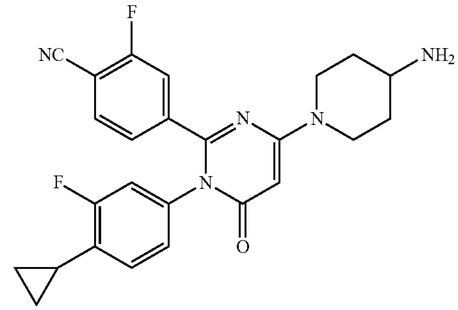 [SMILES: N#Cc1ccc(-c2nc(N3CCC(N)CC3)cc(=O)n2-c2ccc(C3CC3)c(F)c2)cc1F] | 4-[4-(4-aminopiperidin-1-yl)-1-(4-cyclopropyl-3-fluorophenyl)-6-oxopyrimidin-2-yl]-2-fluorobenzonitrile |
| 34 | 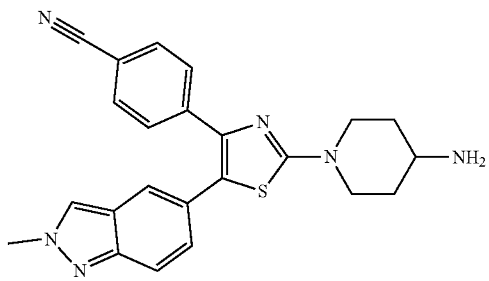 [SMILES: Cn1cc2cc(-c3sc(N4CCC(N)CC4)nc3-c3ccc(C#N)cc3)ccc2n1] | 4-[2-(4-aminopiperidin-1-yl)-5-{2-methyl-2H-indazol-5-yl)pyrazin-2-yl}-1,3-thiazol-4-yl]benzonitrile |

In some embodiments, the substituted heterocyclic derivative compound described herein has the structure provided in Table 2.

TABLE 2

TABLE 2-continued

TABLE 2-continued
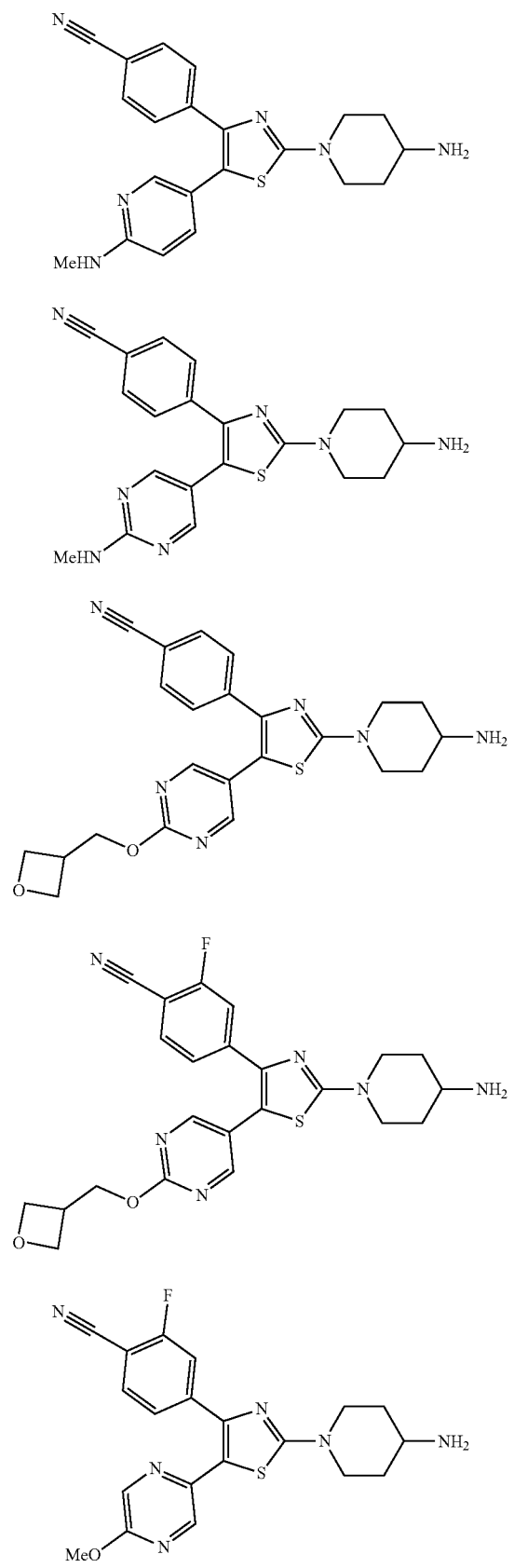
TABLE 2-continued
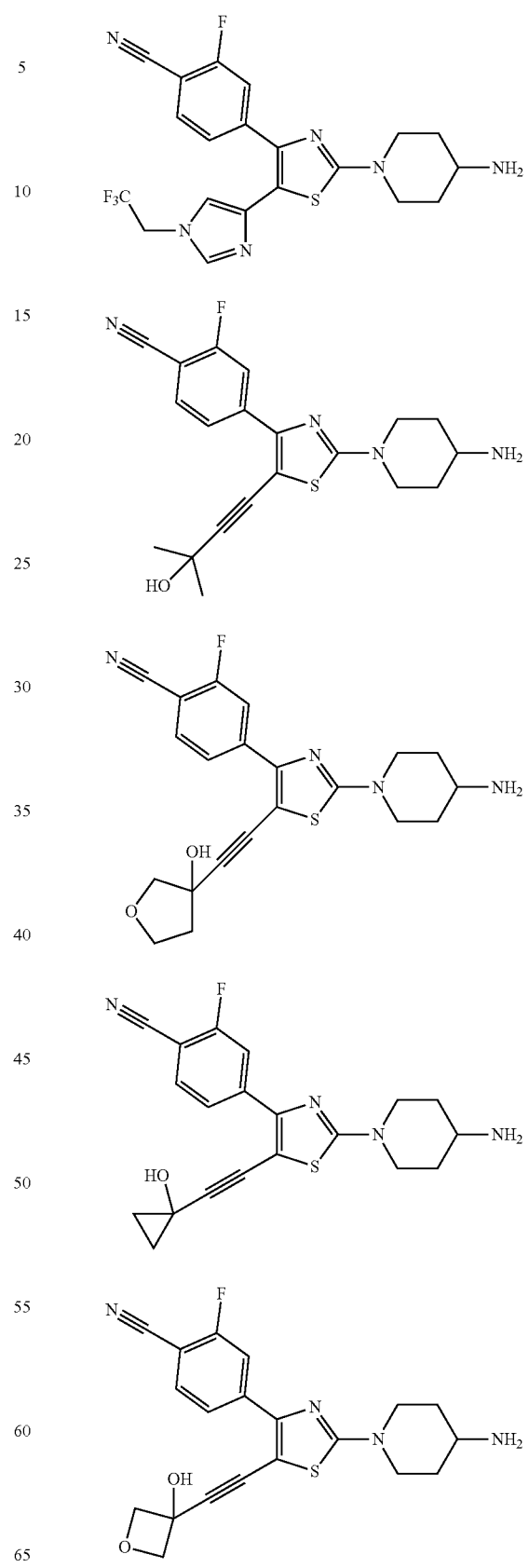

TABLE 2-continued
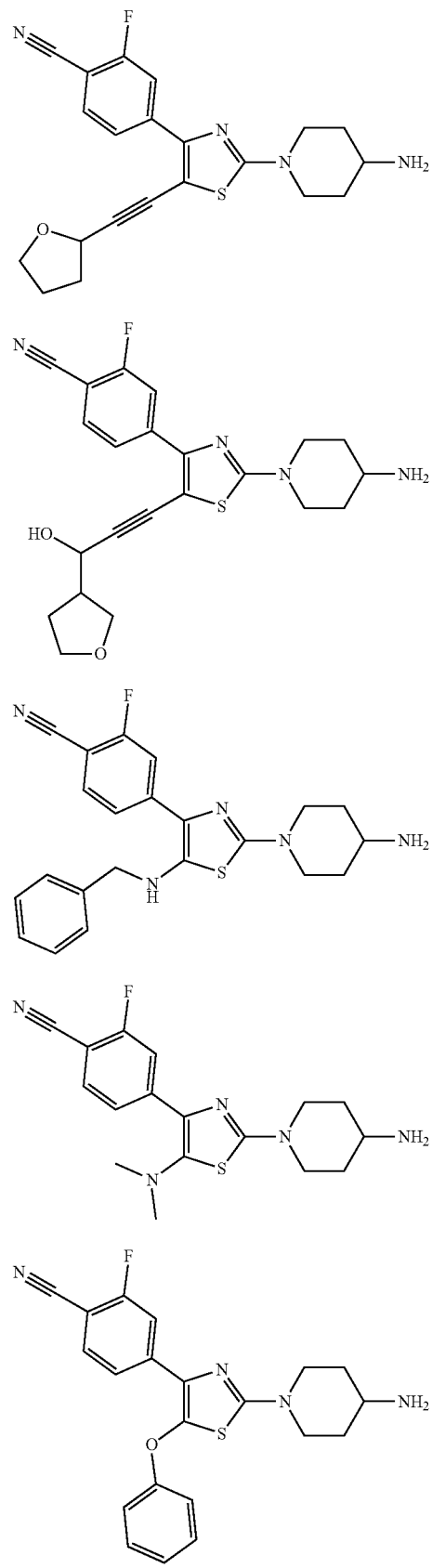
TABLE 2-continued
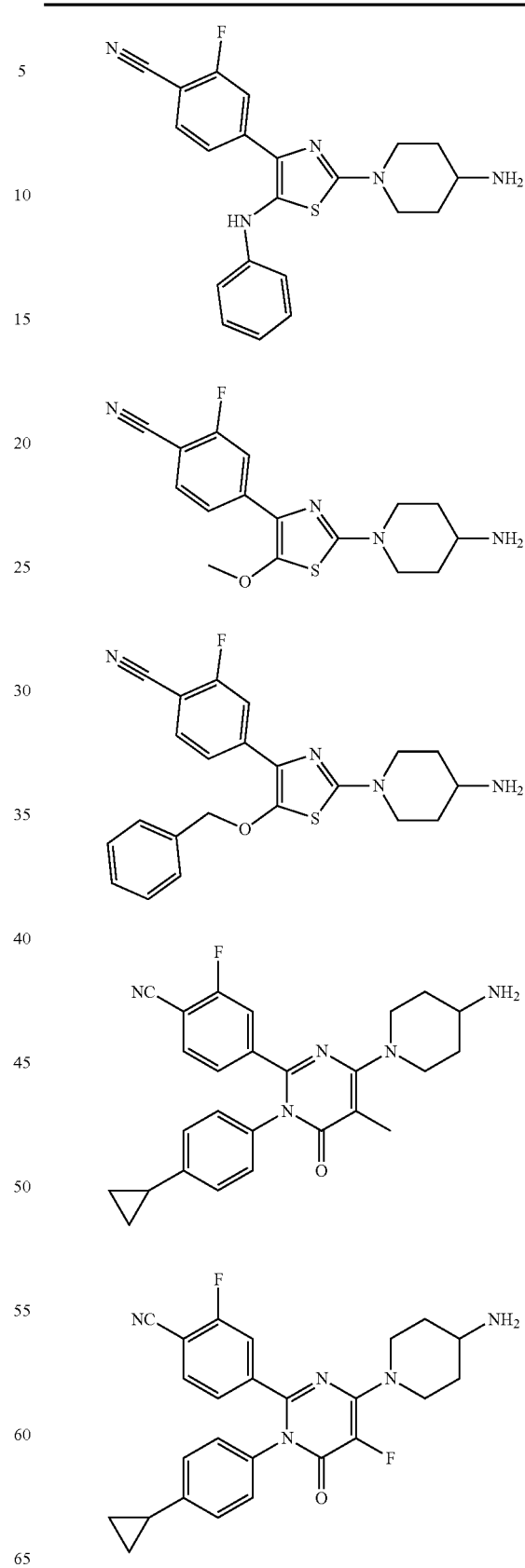

TABLE 2-continued
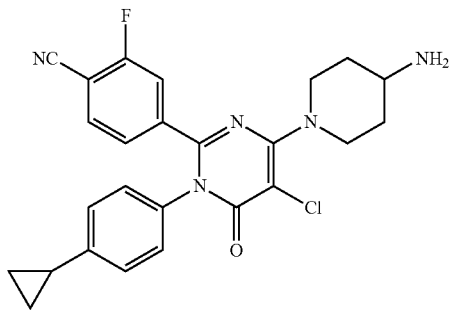 [SMILES: N#Cc1ccc(-c2nc(N3CCC(N)CC3)c(Cl)c(=O)n2-c2ccc(C3CC3)cc2)cc1F]
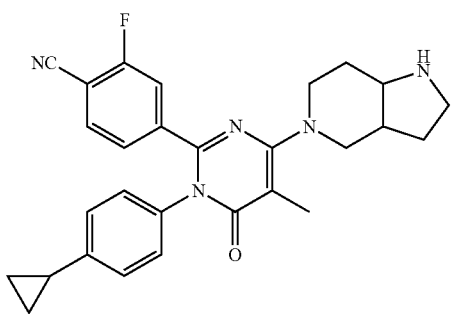 [SMILES: Cc1c(N2CCC3NCCC3C2)nc(-c2ccc(C#N)c(F)c2)n(-c2ccc(C3CC3)cc2)c1=O]
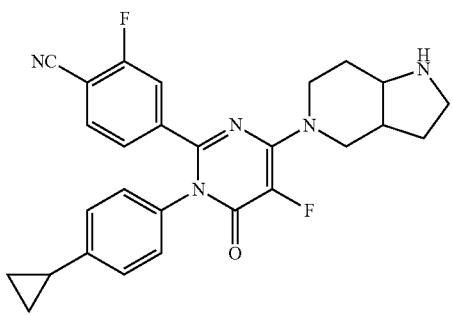 [SMILES: N#Cc1ccc(-c2nc(N3CCC4NCCC4C3)c(F)c(=O)n2-c2ccc(C3CC3)cc2)cc1F]
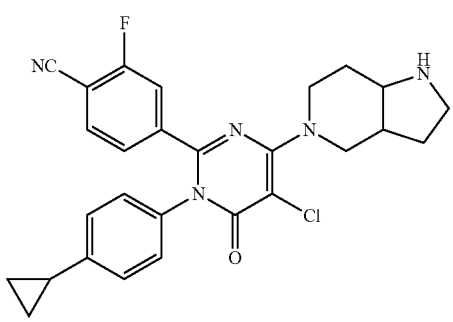 [SMILES: N#Cc1ccc(-c2nc(N3CCC4NCCC4C3)c(Cl)c(=O)n2-c2ccc(C3CC3)cc2)cc1F]
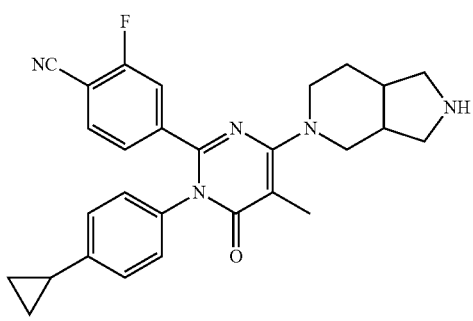 [SMILES: Cc1c(N2CCC3CNCC3C2)nc(-c2ccc(C#N)c(F)c2)n(-c2ccc(C3CC3)cc2)c1=O]
TABLE 2-continued
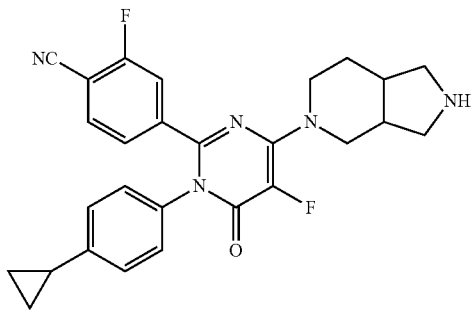 [SMILES: N#Cc1ccc(-c2nc(N3CCC4CNCC4C3)c(F)c(=O)n2-c2ccc(C3CC3)cc2)cc1F]
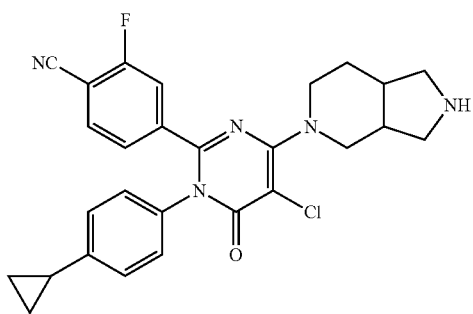 [SMILES: N#Cc1ccc(-c2nc(N3CCC4CNCC4C3)c(Cl)c(=O)n2-c2ccc(C3CC3)cc2)cc1F]
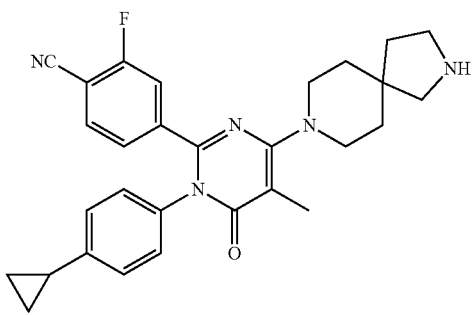 [SMILES: Cc1c(N2CCC3(CCNC3)CC2)nc(-c2ccc(C#N)c(F)c2)n(-c2ccc(C3CC3)cc2)c1=O]
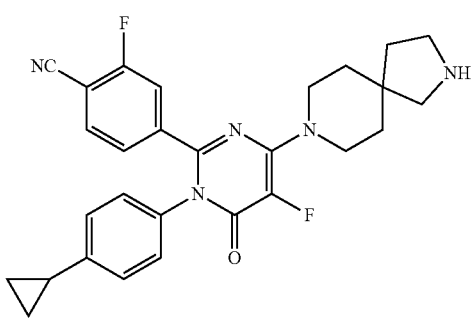 [SMILES: N#Cc1ccc(-c2nc(N3CCC4(CCNC4)CC3)c(F)c(=O)n2-c2ccc(C3CC3)cc2)cc1F]
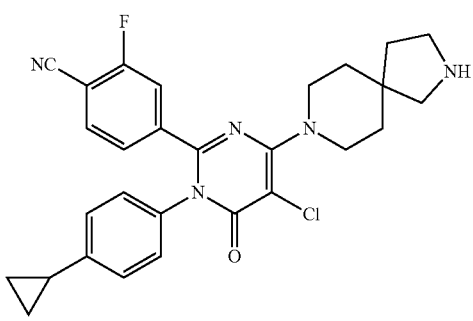

TABLE 2-continued
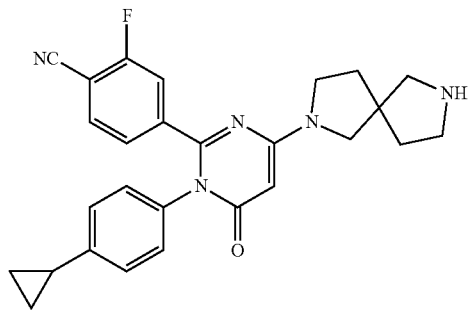 [SMILES: N#Cc1ccc(-c2nc(N3CCC4(CCNC4)C3)cc(=O)n2-c2ccc(C3CC3)cc2)cc1F]
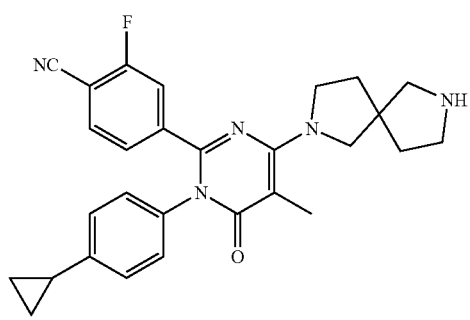 [SMILES: Cc1c(N2CCC3(CCNC3)C2)nc(-c2ccc(C#N)c(F)c2)n(-c2ccc(C3CC3)cc2)c1=O]
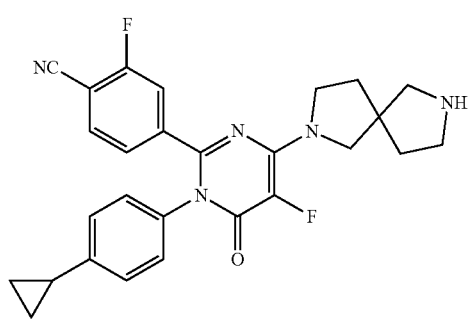 [SMILES: N#Cc1ccc(-c2nc(N3CCC4(CCNC4)C3)c(F)c(=O)n2-c2ccc(C3CC3)cc2)cc1F]
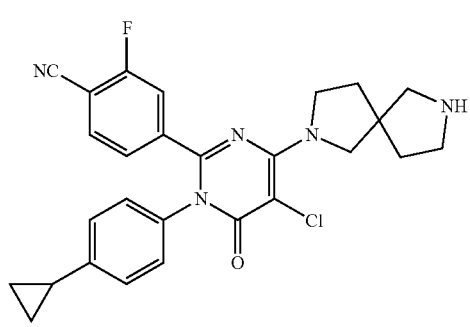 [SMILES: N#Cc1ccc(-c2nc(N3CCC4(CCNC4)C3)c(Cl)c(=O)n2-c2ccc(C3CC3)cc2)cc1F]
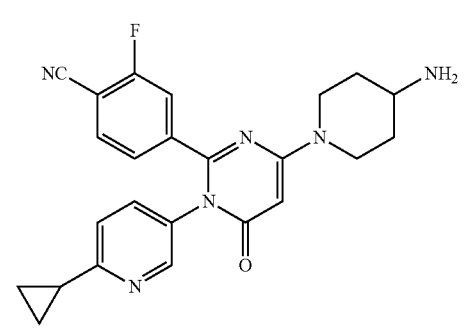
TABLE 2-continued
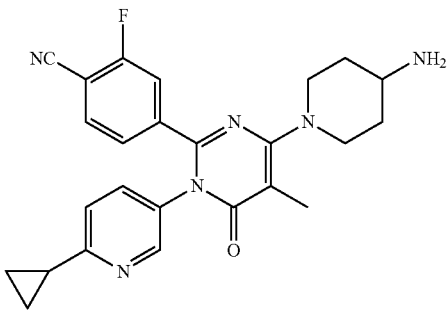 [SMILES: Cc1c(N2CCC(N)CC2)nc(-c2ccc(C#N)c(F)c2)n(-c2ccc(C3CC3)nc2)c1=O]
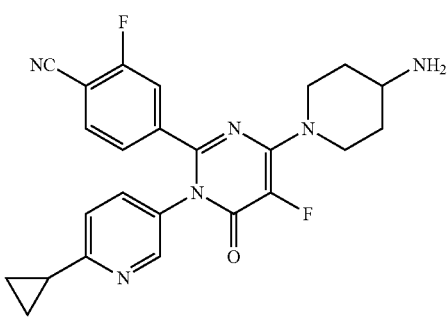 [SMILES: N#Cc1ccc(-c2nc(N3CCC(N)CC3)c(F)c(=O)n2-c2ccc(C3CC3)nc2)cc1F]
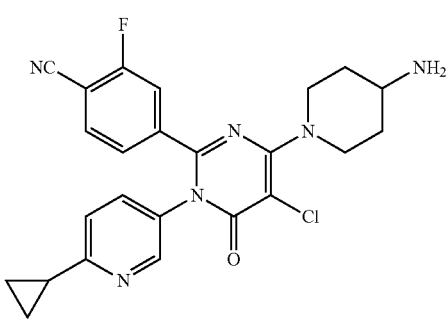 [SMILES: N#Cc1ccc(-c2nc(N3CCC(N)CC3)c(Cl)c(=O)n2-c2ccc(C3CC3)nc2)cc1F]
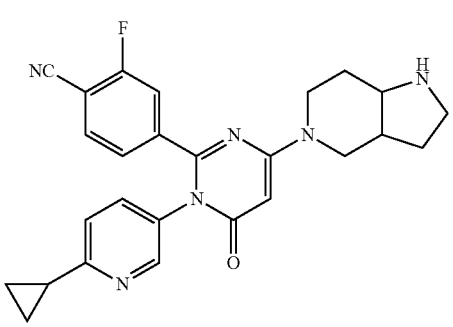 [SMILES: N#Cc1ccc(-c2nc(N3CCC4NCCC4C3)cc(=O)n2-c2ccc(C3CC3)nc2)cc1F]
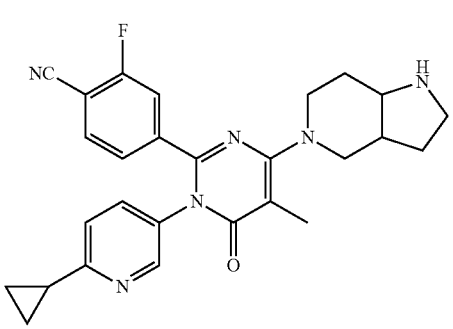 [SMILES: Cc1c(N2CCC3NCCC3C2)nc(-c2ccc(C#N)c(F)c2)n(-c2ccc(C3CC3)nc2)c1=O]

TABLE 2-continued
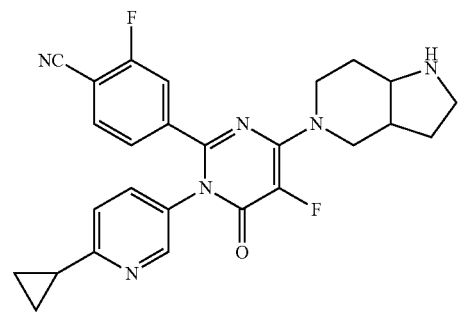
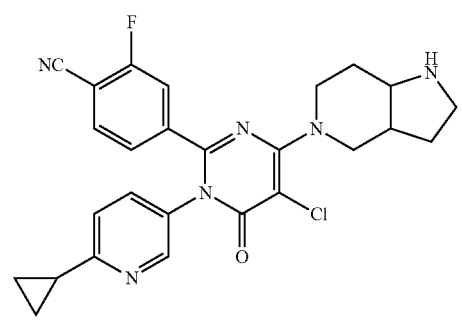
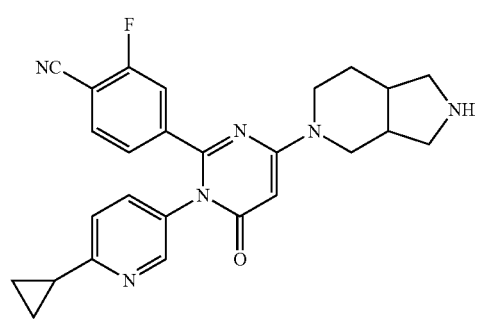 [SMILES: N#Cc1ccc(-c2nc(N3CCC4CNCC4C3)cc(=O)n2-c2ccc(C3CC3)nc2)cc1F]
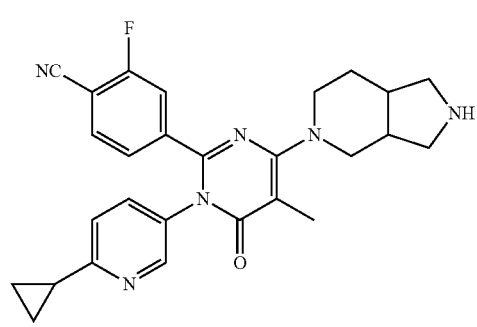
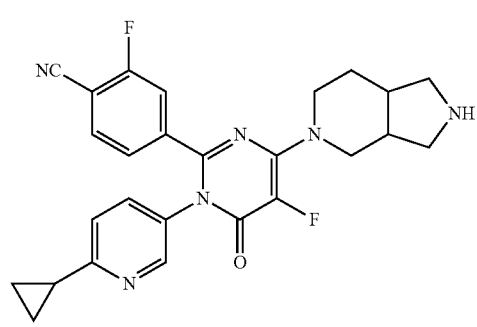 [SMILES: N#Cc1ccc(-c2nc(N3CCC4CNCC4C3)c(F)c(=O)n2-c2ccc(C3CC3)nc2)cc1F]
TABLE 2-continued
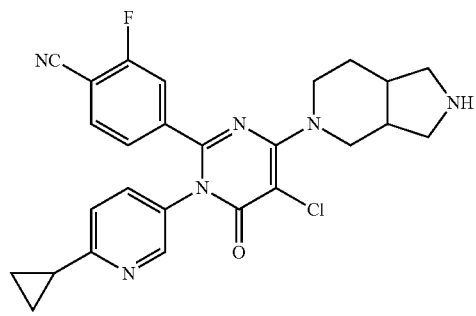 [SMILES: N#Cc1ccc(-c2nc(N3CCC4CNCC4C3)c(Cl)c(=O)n2-c2ccc(C3CC3)nc2)cc1F]
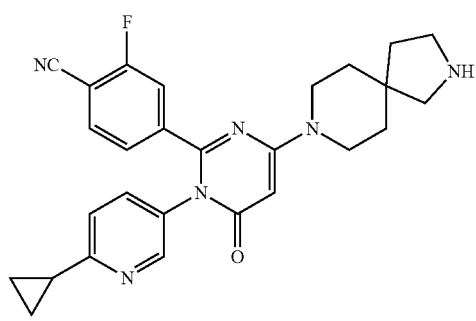 [SMILES: N#Cc1ccc(-c2nc(N3CCC4(CCNC4)CC3)cc(=O)n2-c2ccc(C3CC3)nc2)cc1F]
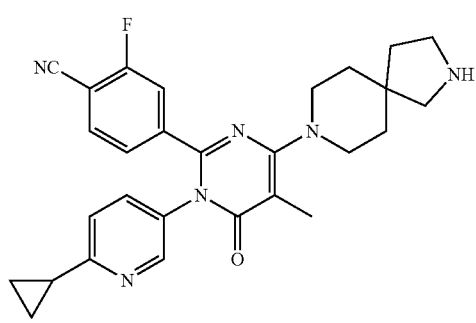 [SMILES: Cc1c(N2CCC3(CCNC3)CC2)nc(-c2ccc(C#N)c(F)c2)n(-c2ccc(C3CC3)nc2)c1=O]
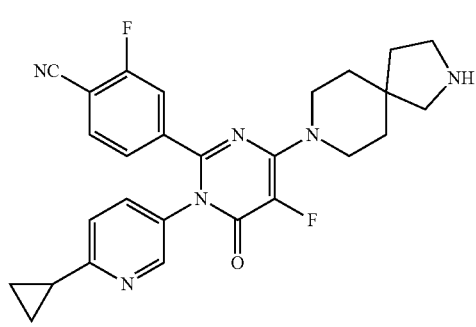 [SMILES: N#Cc1ccc(-c2nc(N3CCC4(CCNC4)CC3)c(F)c(=O)n2-c2ccc(C3CC3)nc2)cc1F]
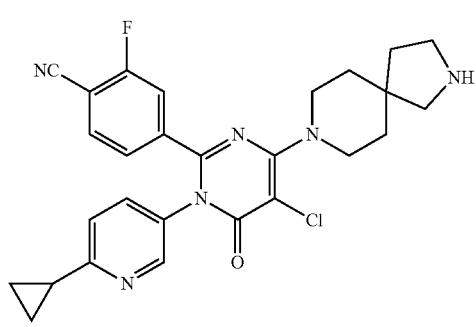

TABLE 2-continued
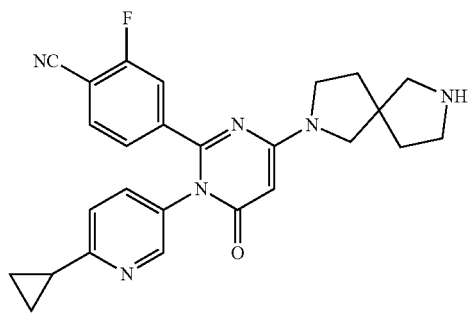 [SMILES: N#Cc1ccc(-c2nc(N3CCC4(CCNC4)C3)cc(=O)n2-c2ccc(C3CC3)nc2)cc1F]
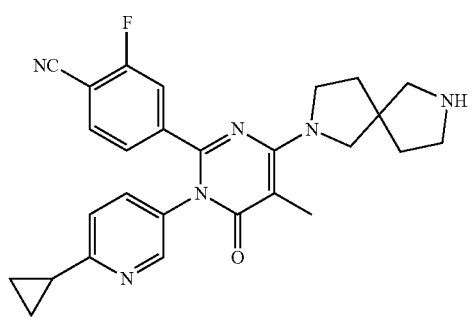 [SMILES: Cc1c(N2CCC3(CCNC3)C2)nc(-c2ccc(C#N)c(F)c2)n(-c2ccc(C3CC3)nc2)c1=O]
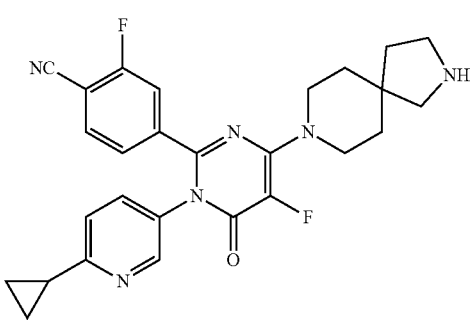 [SMILES: N#Cc1ccc(-c2nc(N3CCC4(CCNC4)CC3)c(F)c(=O)n2-c2ccc(C3CC3)nc2)cc1F]
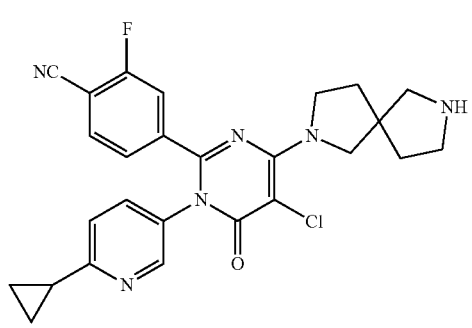 [SMILES: N#Cc1ccc(-c2nc(N3CCC4(CCNC4)C3)c(Cl)c(=O)n2-c2ccc(C3CC3)nc2)cc1F]
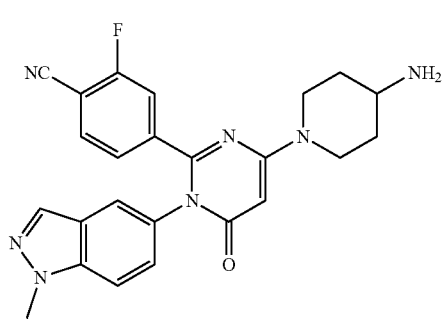 [SMILES: Cn1ncc2cc(-n3c(-c4ccc(C#N)c(F)c4)nc(N4CCC(N)CC4)cc3=O)ccc21]
TABLE 2-continued
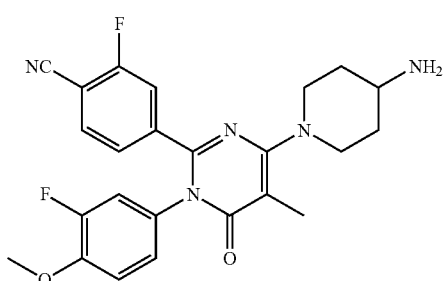
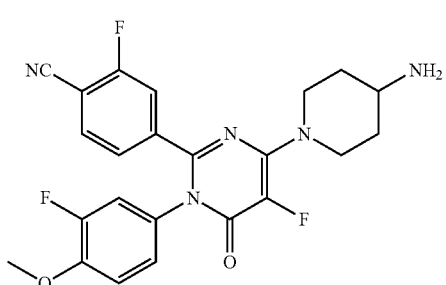
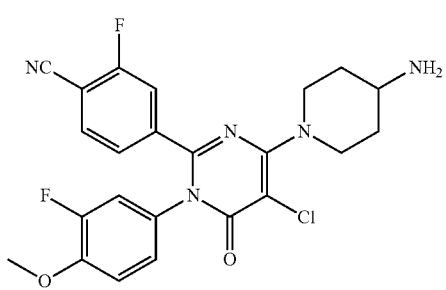 [SMILES: COc1ccc(-n2c(-c3ccc(C#N)c(F)c3)nc(N3CCC(N)CC3)c(Cl)c2=O)cc1F]
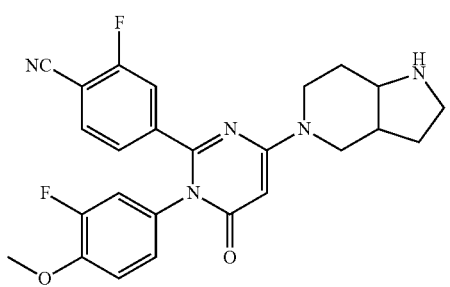 [SMILES: COc1ccc(-n2c(-c3ccc(C#N)c(F)c3)nc(N3CCC4NCCC4C3)cc2=O)cc1F]
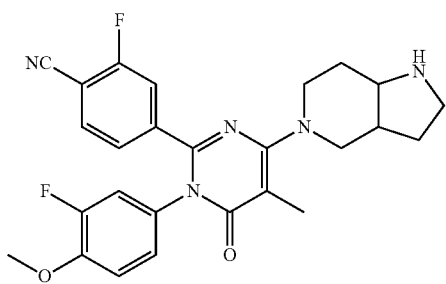 [SMILES: COc1ccc(-n2c(-c3ccc(C#N)c(F)c3)nc(N3CCC4NCCC4C3)c(C)c2=O)cc1F]

TABLE 2-continued
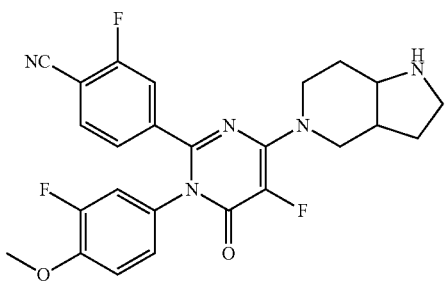 [SMILES: COc1ccc(-n2c(-c3ccc(C#N)c(F)c3)nc(N3CCC4NCCC4C3)c(F)c2=O)cc1F]
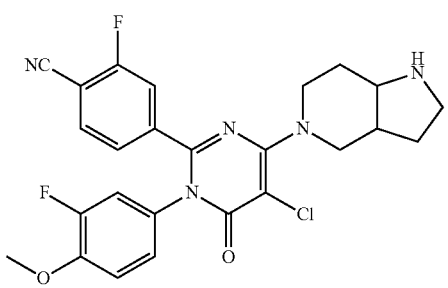 [SMILES: COc1ccc(-n2c(-c3ccc(C#N)c(F)c3)nc(N3CCC4NCCC4C3)c(Cl)c2=O)cc1F]
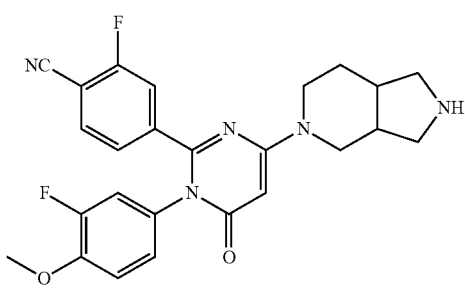 [SMILES: COc1ccc(-n2c(-c3ccc(C#N)c(F)c3)nc(N3CCC4CNCC4C3)cc2=O)cc1F]
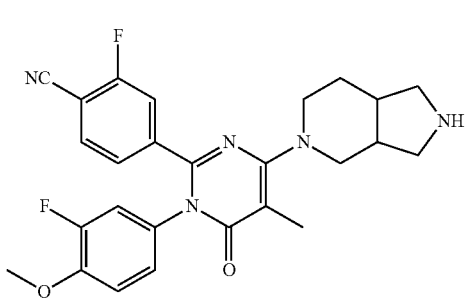 [SMILES: COc1ccc(-n2c(-c3ccc(C#N)c(F)c3)nc(N3CCC4CNCC4C3)c(C)c2=O)cc1F]
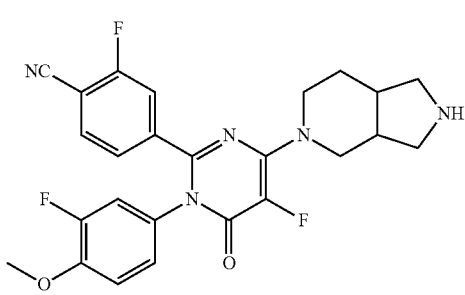 [SMILES: COc1ccc(-n2c(-c3ccc(C#N)c(F)c3)nc(N3CCC4CNCC4C3)c(F)c2=O)cc1F]
TABLE 2-continued
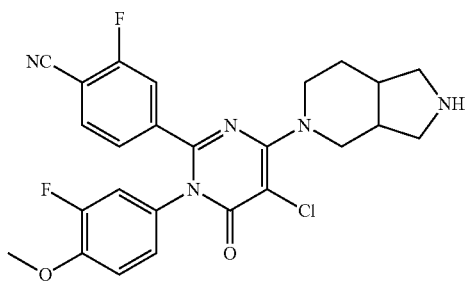 [SMILES: COc1ccc(-n2c(-c3ccc(C#N)c(F)c3)nc(N3CCC4CNCC4C3)c(Cl)c2=O)cc1F]
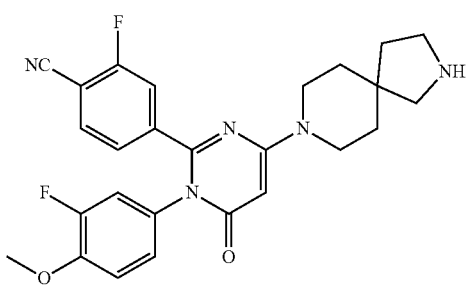 [SMILES: COc1ccc(-n2c(-c3ccc(C#N)c(F)c3)nc(N3CCC4(CCNC4)CC3)cc2=O)cc1F]
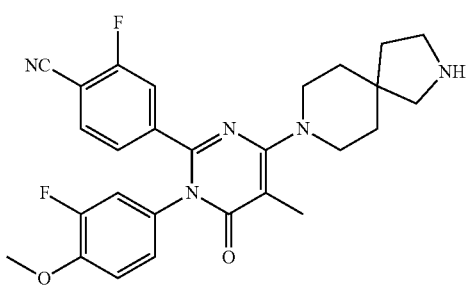 [SMILES: COc1ccc(-n2c(-c3ccc(C#N)c(F)c3)nc(N3CCC4(CCNC4)CC3)c(C)c2=O)cc1F]
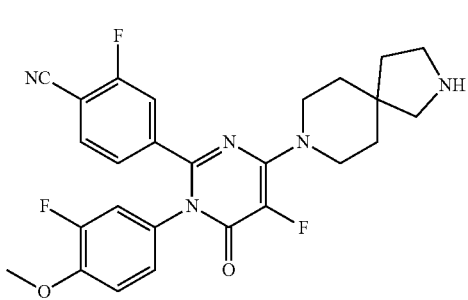 [SMILES: COc1ccc(-n2c(-c3ccc(C#N)c(F)c3)nc(N3CCC4(CCNC4)CC3)c(F)c2=O)cc1F]
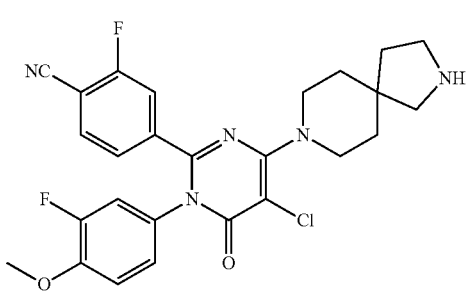

TABLE 2-continued
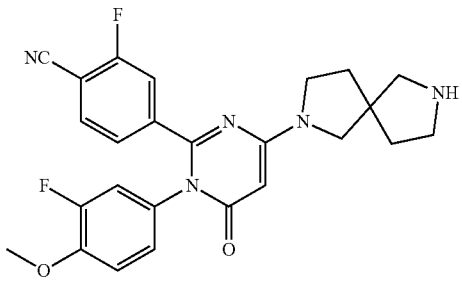 [SMILES: COc1ccc(-n2c(-c3ccc(C#N)c(F)c3)nc(N3CCC4(CCNC4)C3)cc2=O)cc1F]
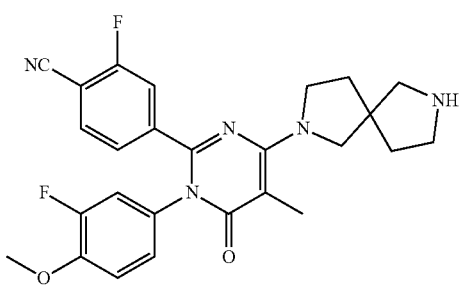 [SMILES: COc1ccc(-n2c(-c3ccc(C#N)c(F)c3)nc(N3CCC4(CCNC4)C3)c(C)c2=O)cc1F]
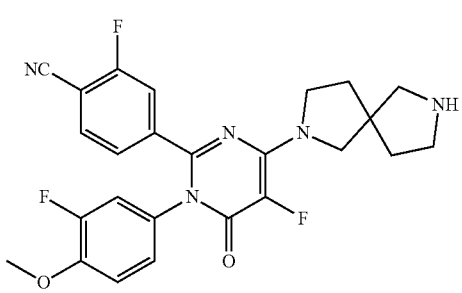 [SMILES: COc1ccc(-n2c(-c3ccc(C#N)c(F)c3)nc(N3CCC4(CCNC4)C3)c(F)c2=O)cc1F]
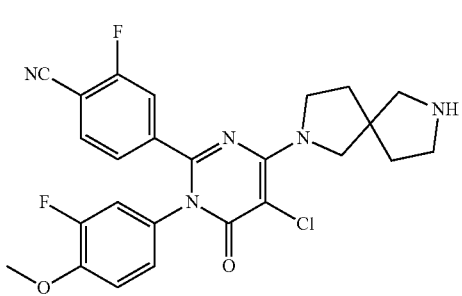 [SMILES: COc1ccc(-n2c(-c3ccc(C#N)c(F)c3)nc(N3CCC4(CCNC4)C3)c(Cl)c2=O)cc1F]
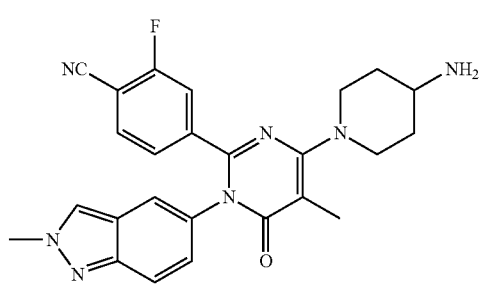 [SMILES: Cc1c(N2CCC(N)CC2)nc(-c2ccc(C#N)c(F)c2)n(-c2ccc3nn(C)cc3c2)c1=O]
TABLE 2-continued
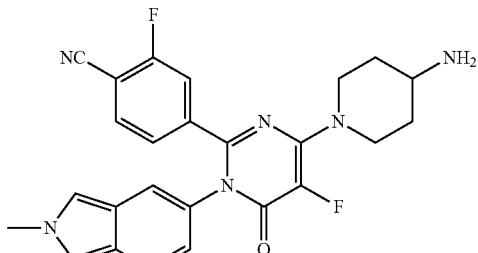
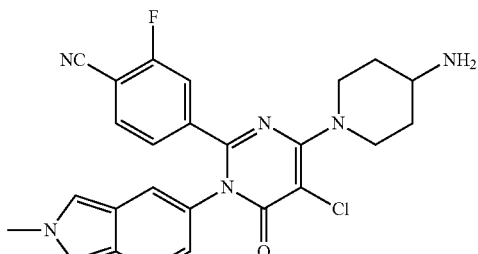
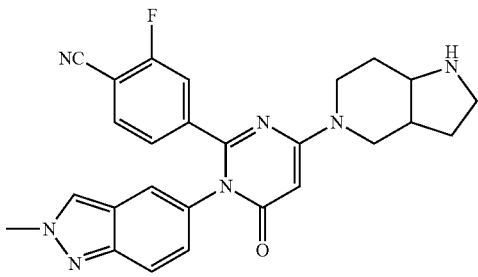 [SMILES: Cn1cc2cc(-n3c(-c4ccc(C#N)c(F)c4)nc(N4CCC5NCCC5C4)cc3=O)ccc2n1]
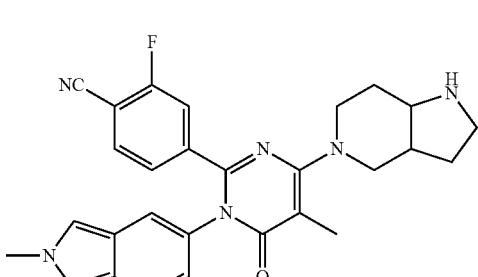
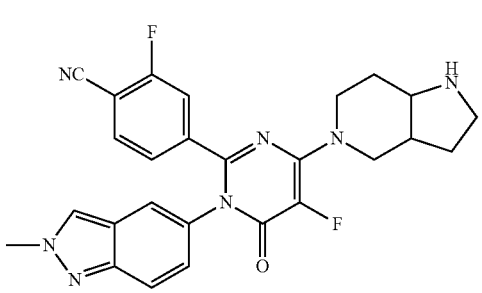 [SMILES: Cn1cc2cc(-n3c(-c4ccc(C#N)c(F)c4)nc(N4CCC5NCCC5C4)c(F)c3=O)ccc2n1]

TABLE 2-continued
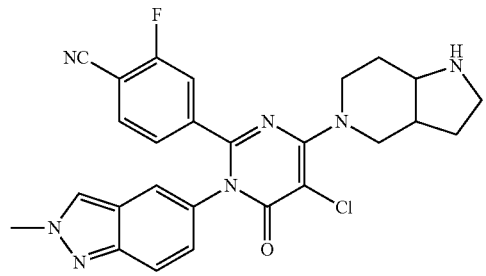 [SMILES: Cn1cc2cc(-n3c(-c4ccc(C#N)c(F)c4)nc(N4CCC5NCCC5C4)c(Cl)c3=O)ccc2n1]
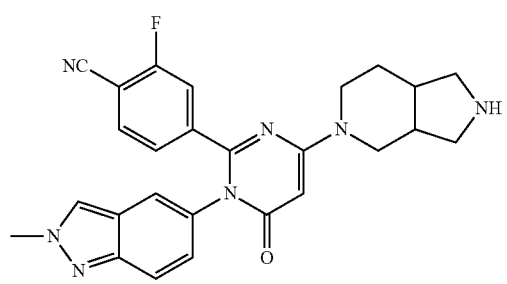 [SMILES: Cn1cc2cc(-n3c(-c4ccc(C#N)c(F)c4)nc(N4CCC5CNCC5C4)cc3=O)ccc2n1]
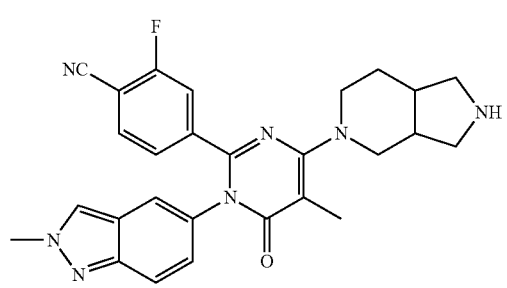 [SMILES: Cc1c(N2CCC3CNCC3C2)nc(-c2ccc(C#N)c(F)c2)n(-c2ccc3nn(C)cc3c2)c1=O]
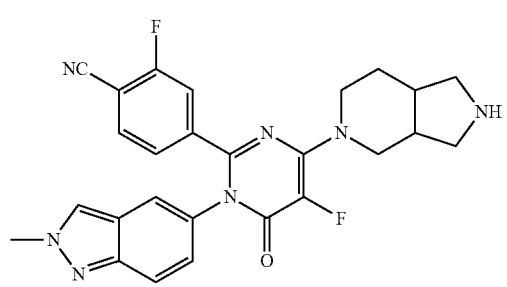 [SMILES: Cn1cc2cc(-n3c(-c4ccc(C#N)c(F)c4)nc(N4CCC5CNCC5C4)c(F)c3=O)ccc2n1]
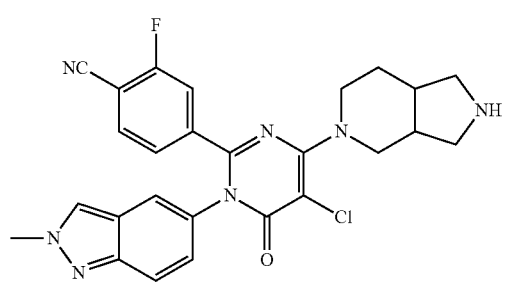 [SMILES: Cn1cc2cc(-n3c(-c4ccc(C#N)c(F)c4)nc(N4CCC5CNCC5C4)c(Cl)c3=O)ccc2n1]
TABLE 2-continued
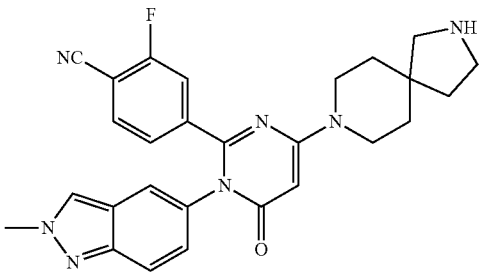 [SMILES: Cn1cc2cc(-n3c(-c4ccc(C#N)c(F)c4)nc(N4CCC5(CCNC5)CC4)cc3=O)ccc2n1]
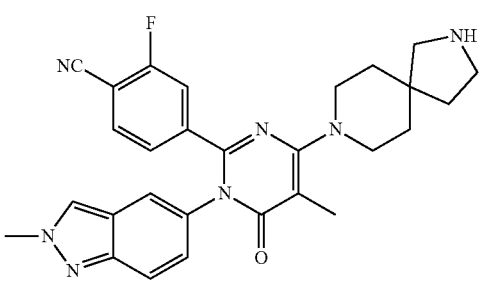 [SMILES: Cc1c(N2CCC3(CCNC3)CC2)nc(-c2ccc(C#N)c(F)c2)n(-c2ccc3nn(C)cc3c2)c1=O]
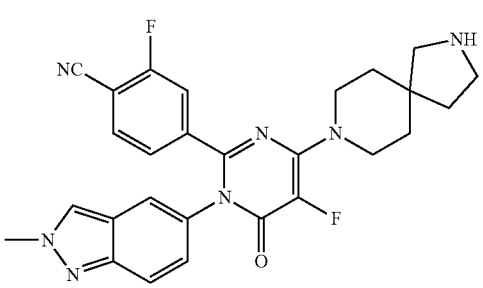 [SMILES: Cn1cc2cc(-n3c(-c4ccc(C#N)c(F)c4)nc(N4CCC5(CCNC5)CC4)c(F)c3=O)ccc2n1]
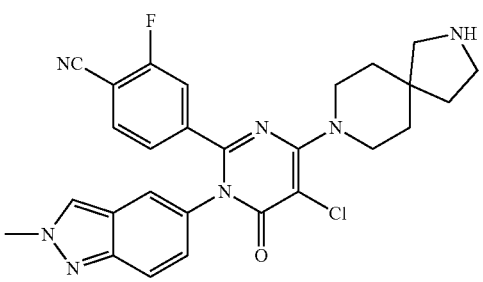 [SMILES: Cn1cc2cc(-n3c(-c4ccc(C#N)c(F)c4)nc(N4CCC5(CCNC5)CC4)c(Cl)c3=O)ccc2n1]
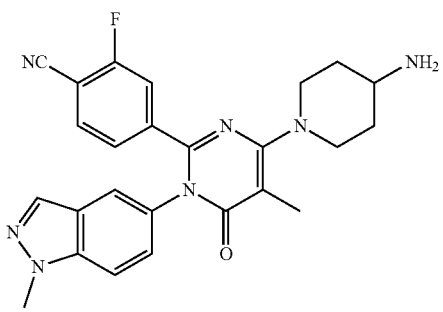 [SMILES: Cc1c(N2CCC(N)CC2)nc(-c2ccc(C#N)c(F)c2)n(-c2ccc3c(cnn3C)c2)c1=O]

TABLE 2-continued
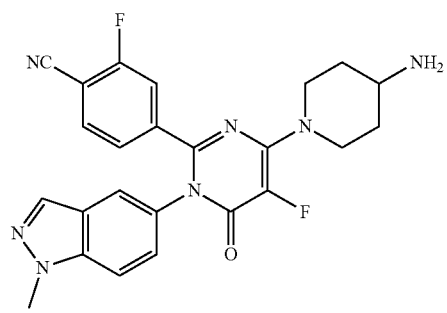 [SMILES: Cn1ncc2cc(-n3c(-c4ccc(C#N)c(F)c4)nc(N4CCC(N)CC4)c(F)c3=O)ccc21]
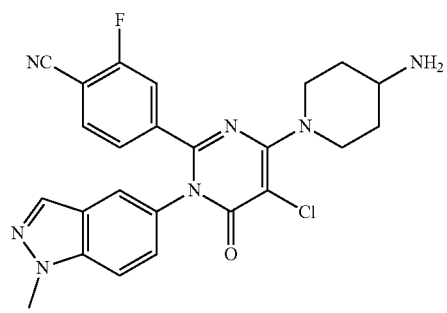 [SMILES: Cn1ncc2cc(-n3c(-c4ccc(C#N)c(F)c4)nc(N4CCC(N)CC4)c(Cl)c3=O)ccc21]
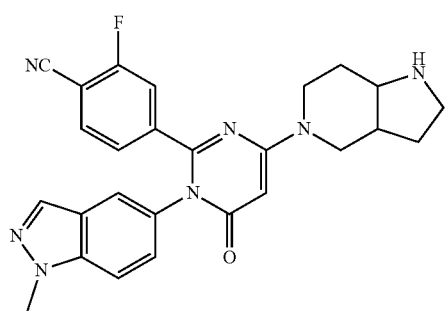 [SMILES: Cn1ncc2cc(-n3c(-c4ccc(C#N)c(F)c4)nc(N4CCC5NCCC5C4)cc3=O)ccc21]
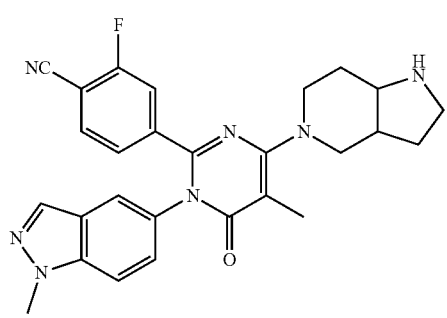 [SMILES: Cc1c(N2CCC3NCCC3C2)nc(-c2ccc(C#N)c(F)c2)n(-c2ccc3c(cnn3C)c2)c1=O]
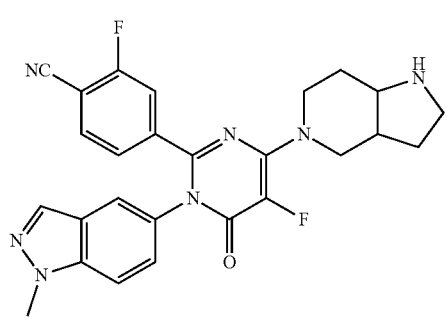 [SMILES: Cn1ncc2cc(-n3c(-c4ccc(C#N)c(F)c4)nc(N4CCC5NCCC5C4)c(F)c3=O)ccc21]
TABLE 2-continued
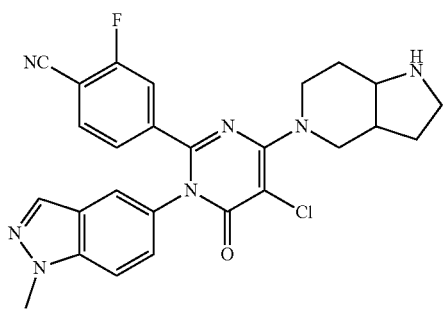 [SMILES: Cn1ncc2cc(-n3c(-c4ccc(C#N)c(F)c4)nc(N4CCC5NCCC5C4)c(Cl)c3=O)ccc21]
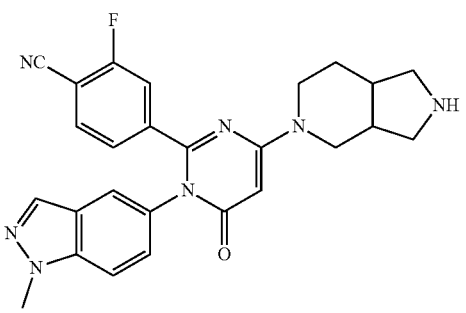 [SMILES: Cn1ncc2cc(-n3c(-c4ccc(C#N)c(F)c4)nc(N4CCC5CNCC5C4)cc3=O)ccc21]
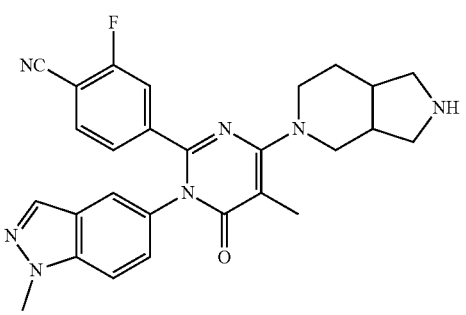 [SMILES: Cc1c(N2CCC3CNCC3C2)nc(-c2ccc(C#N)c(F)c2)n(-c2ccc3c(cnn3C)c2)c1=O]
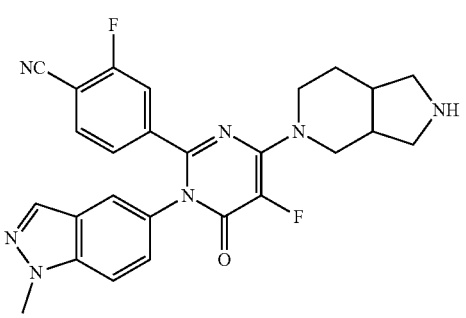 [SMILES: Cn1ncc2cc(-n3c(-c4ccc(C#N)c(F)c4)nc(N4CCC5CNCC5C4)c(F)c3=O)ccc21]
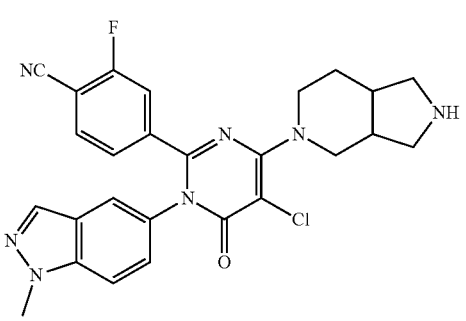

TABLE 2-continued
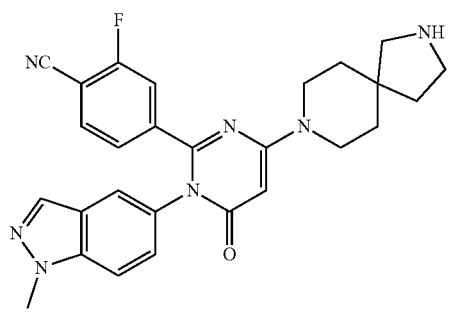 [SMILES: Cn1ncc2cc(-n3c(-c4ccc(C#N)c(F)c4)nc(N4CCC5(CCNC5)CC4)cc3=O)ccc21]
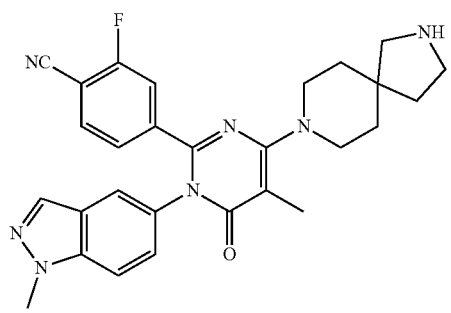 [SMILES: Cc1c(N2CCC3(CCNC3)CC2)nc(-c2ccc(C#N)c(F)c2)n(-c2ccc3c(cnn3C)c2)c1=O]
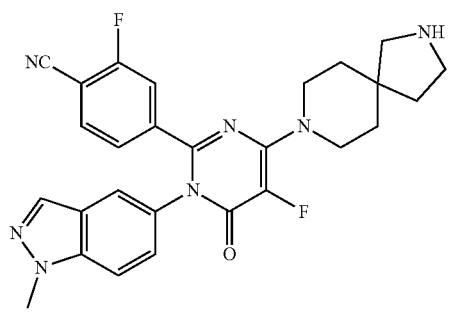 [SMILES: Cn1ncc2cc(-n3c(-c4ccc(C#N)c(F)c4)nc(N4CCC5(CCNC5)CC4)c(F)c3=O)ccc21]
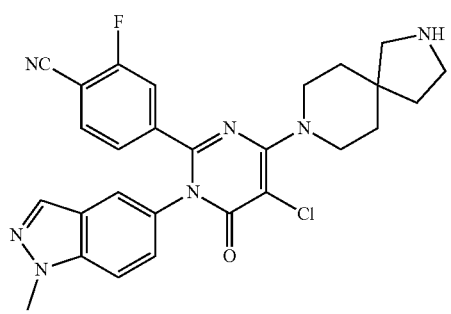 [SMILES: Cn1ncc2cc(-n3c(-c4ccc(C#N)c(F)c4)nc(N4CCC5(CCNC5)CC4)c(Cl)c3=O)ccc21]
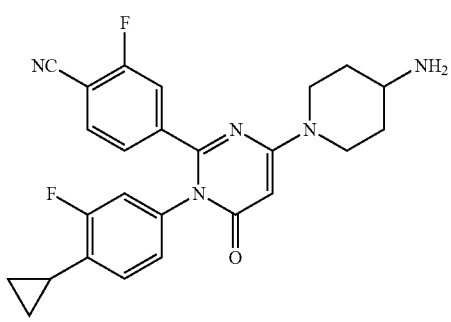 [SMILES: N#Cc1ccc(-c2nc(N3CCC(N)CC3)cc(=O)n2-c2ccc(C3CC3)c(F)c2)cc1F]
TABLE 2-continued
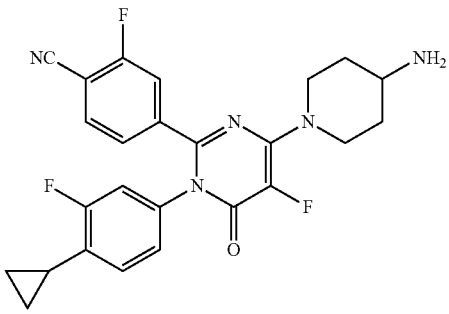 [SMILES: N#Cc1ccc(-c2nc(N3CCC(N)CC3)c(F)c(=O)n2-c2ccc(C3CC3)c(F)c2)cc1F]
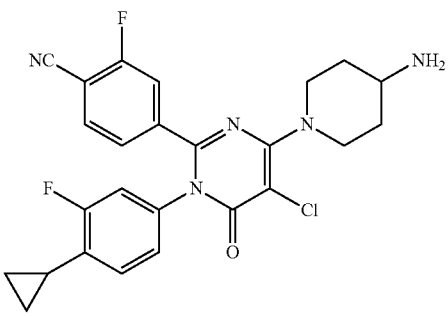 [SMILES: N#Cc1ccc(-c2nc(N3CCC(N)CC3)c(Cl)c(=O)n2-c2ccc(C3CC3)c(F)c2)cc1F]
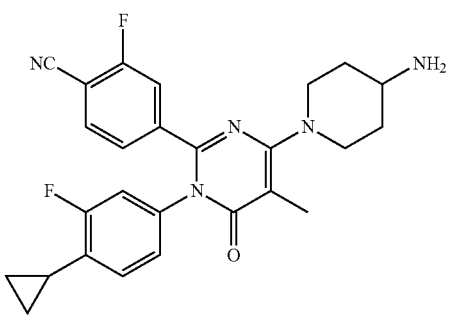
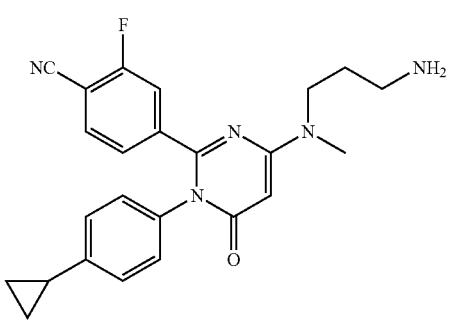 [SMILES: CN(CCCN)c1cc(=O)n(-c2ccc(C3CC3)cc2)c(-c2ccc(C#N)c(F)c2)n1]
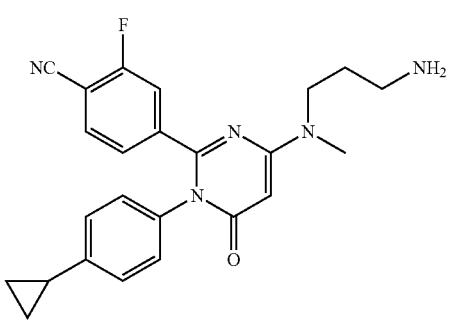 [SMILES: CN(CCCN)c1cc(=O)n(-c2ccc(C3CC3)cc2)c(-c2ccc(C#N)c(F)c2)n1]

TABLE 2-continued
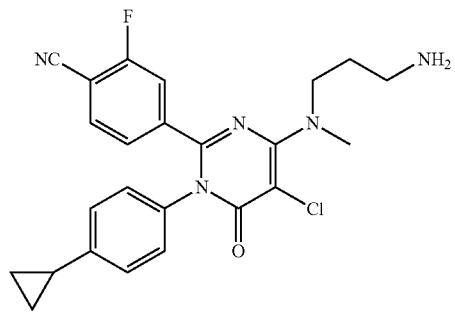 [SMILES: CN(CCCN)c1nc(-c2ccc(C#N)c(F)c2)n(-c2ccc(C3CC3)cc2)c(=O)c1Cl]
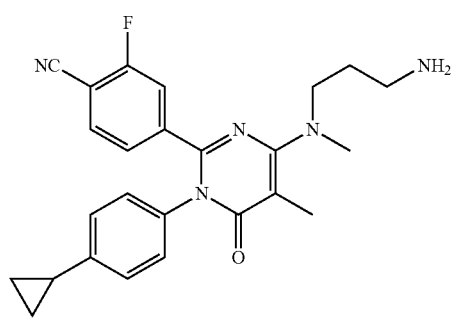 [SMILES: Cc1c(N(C)CCCN)nc(-c2ccc(C#N)c(F)c2)n(-c2ccc(C3CC3)cc2)c1=O]
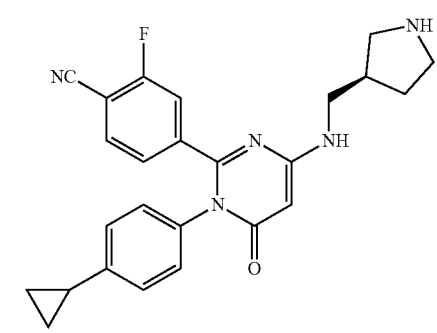 [SMILES: N#Cc1ccc(-c2nc(NC[C@@H]3CCNC3)cc(=O)n2-c2ccc(C3CC3)cc2)cc1F]
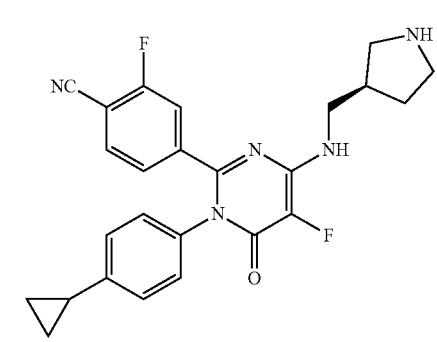 [SMILES: N#Cc1ccc(-c2nc(NC[C@@H]3CCNC3)c(F)c(=O)n2-c2ccc(C3CC3)cc2)cc1F]
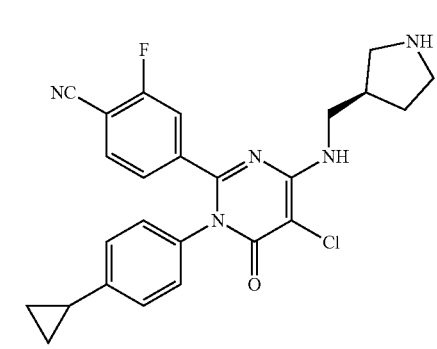 [SMILES: N#Cc1ccc(-c2nc(NC[C@@H]3CCNC3)c(Cl)c(=O)n2-c2ccc(C3CC3)cc2)cc1F]
TABLE 2-continued
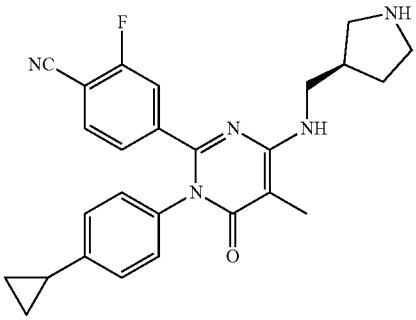 [SMILES: Cc1c(NC[C@@H]2CCNC2)nc(-c2ccc(C#N)c(F)c2)n(-c2ccc(C3CC3)cc2)c1=O]
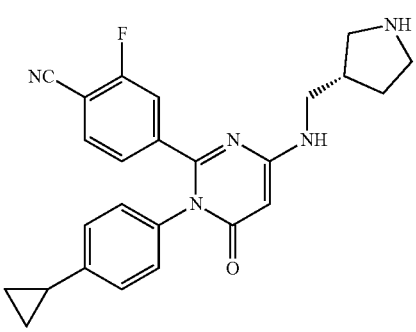 [SMILES: N#Cc1ccc(-c2nc(NC[C@H]3CCNC3)cc(=O)n2-c2ccc(C3CC3)cc2)cc1F]
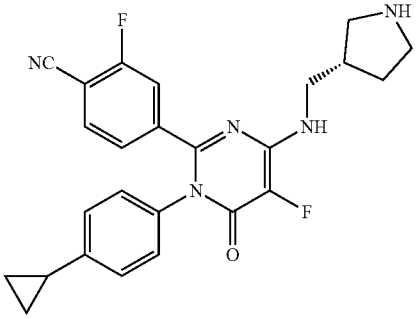 [SMILES: N#Cc1ccc(-c2nc(NC[C@H]3CCNC3)c(F)c(=O)n2-c2ccc(C3CC3)cc2)cc1F]
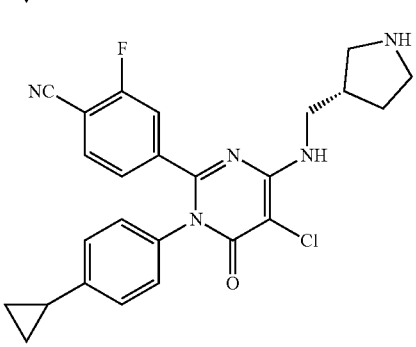
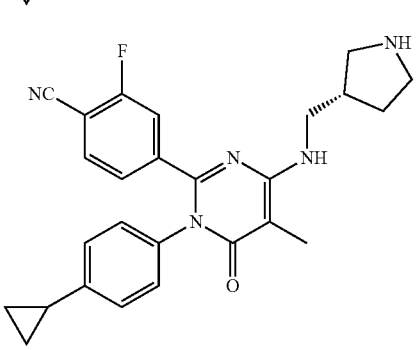

TABLE 2-continued
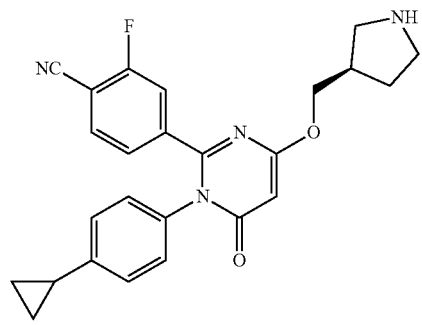 [SMILES: N#Cc1ccc(-c2nc(OC[C@@H]3CCNC3)cc(=O)n2-c2ccc(C3CC3)cc2)cc1F]
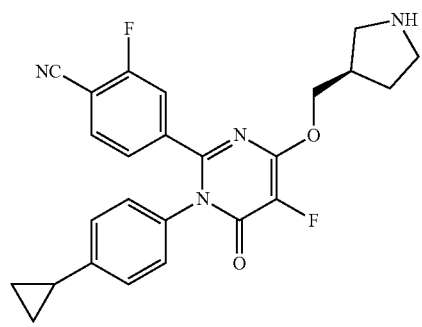 [SMILES: N#Cc1ccc(-c2nc(OC[C@@H]3CCNC3)c(F)c(=O)n2-c2ccc(C3CC3)cc2)cc1F]
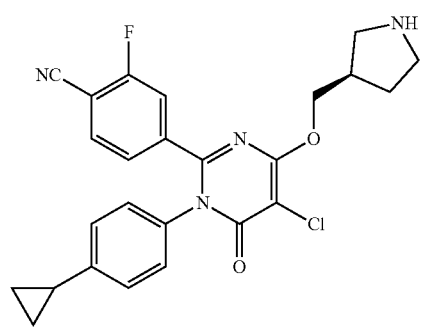 [SMILES: N#Cc1ccc(-c2nc(OC[C@@H]3CCNC3)c(Cl)c(=O)n2-c2ccc(C3CC3)cc2)cc1F]
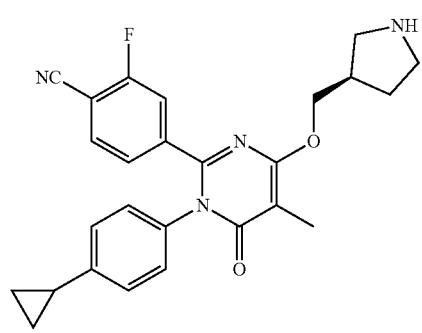 [SMILES: Cc1c(OC[C@@H]2CCNC2)nc(-c2ccc(C#N)c(F)c2)n(-c2ccc(C3CC3)cc2)c1=O]
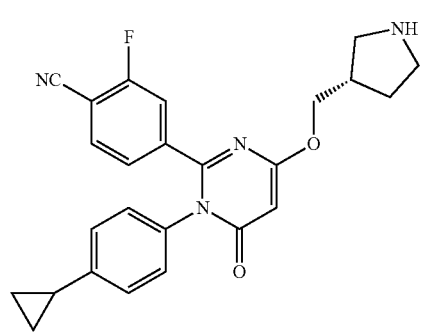 [SMILES: N#Cc1ccc(-c2nc(OC[C@H]3CCNC3)cc(=O)n2-c2ccc(C3CC3)cc2)cc1F]
TABLE 2-continued
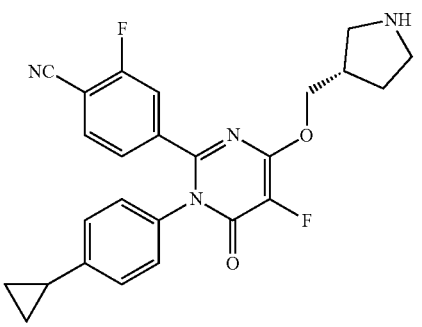 [SMILES: N#Cc1ccc(-c2nc(OC[C@H]3CCNC3)c(F)c(=O)n2-c2ccc(C3CC3)cc2)cc1F]
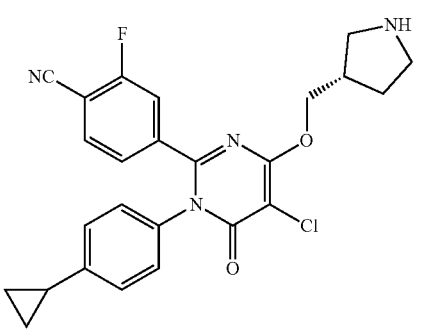 [SMILES: N#Cc1ccc(-c2nc(OC[C@H]3CCNC3)c(Cl)c(=O)n2-c2ccc(C3CC3)cc2)cc1F]
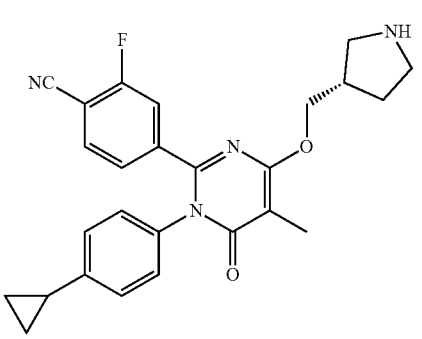 [SMILES: Cc1c(OC[C@H]2CCNC2)nc(-c2ccc(C#N)c(F)c2)n(-c2ccc(C3CC3)cc2)c1=O]
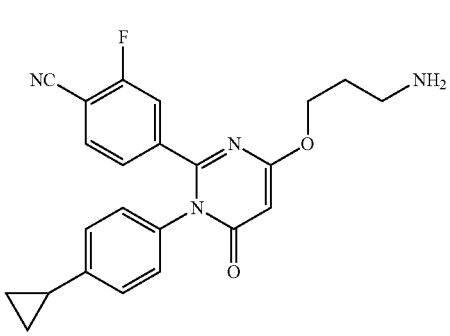 [SMILES: N#Cc1ccc(-c2nc(OCCCN)cc(=O)n2-c2ccc(C3CC3)cc2)cc1F]
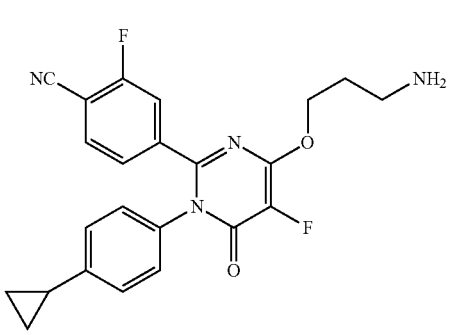 [SMILES: N#Cc1ccc(-c2nc(OCCCN)c(F)c(=O)n2-c2ccc(C3CC3)cc2)cc1F]
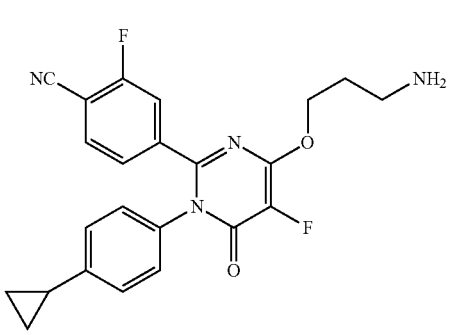 [SMILES: N#Cc1ccc(-c2nc(OCCCN)c(F)c(=O)n2-c2ccc(C3CC3)cc2)cc1F]

TABLE 2-continued

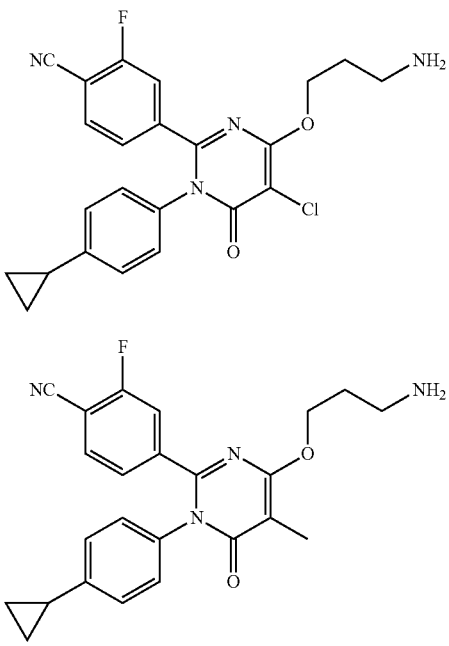

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is P. H. Stahl & C. G. Wermuth "Handbook of Pharmaceutical Salts", Verlag Helvetica Chimica Acta, Zurich, 2002.

The substituted heterocyclic derivative compounds are prepared by the general synthetic routes described below in Schemes 1-3.

The substituted thiazole derivative compounds are prepared by the general synthetic route described below in Scheme 1.

Scheme 1

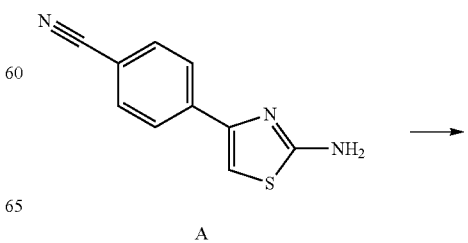

A

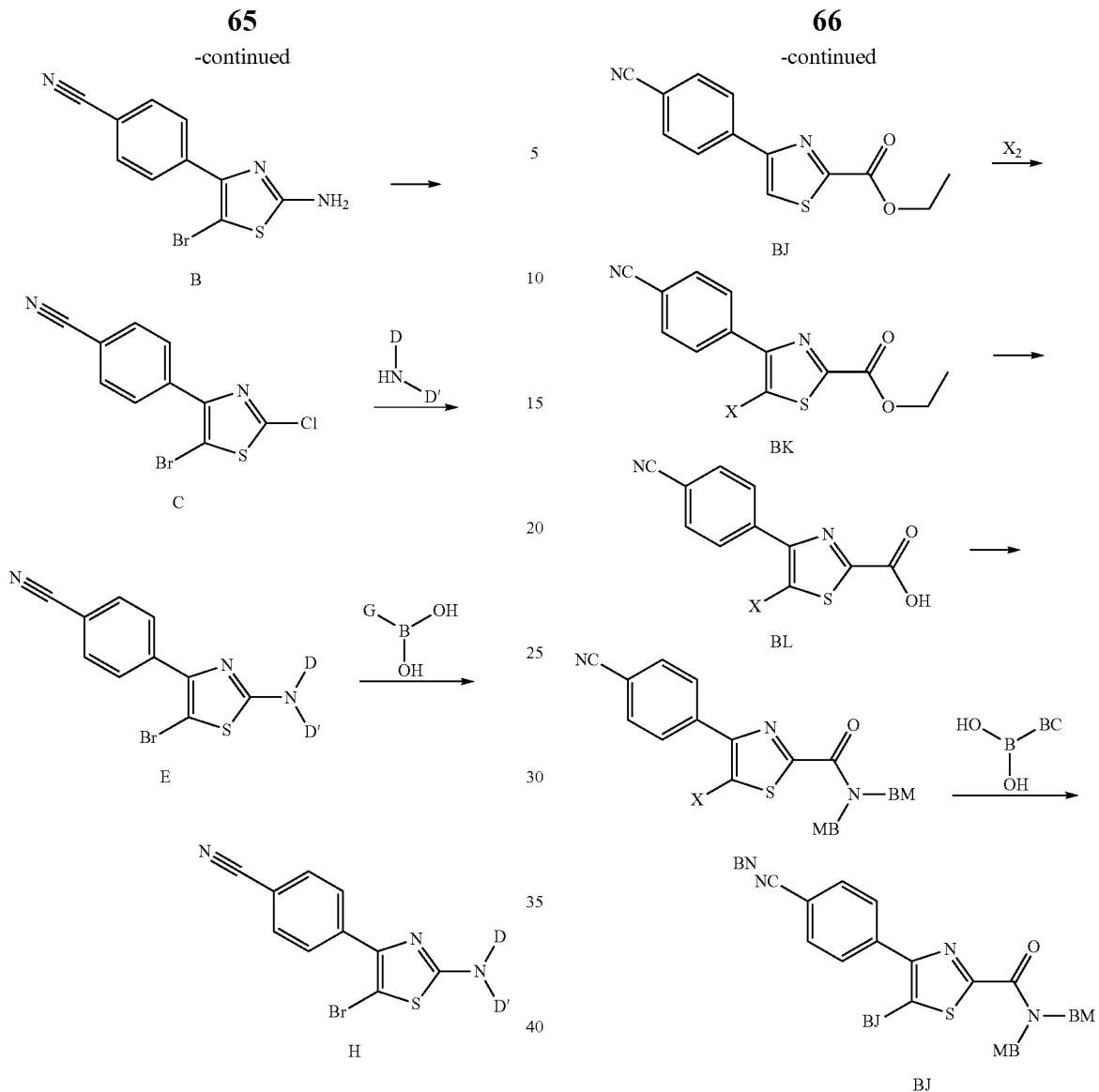

Referring to Scheme 1, bromination of compound A yields compound B. Compound C is obtained from treatment of compound B under Sandmayer substitution condition. Displacement of compound C is carried out with a variety of amines DD'-NH₂ under basic conditions to form compound E. Compound H is prepared from aryl halide compound E using palladium-mediated cross coupling conditions with boronic acids G-(OH)₂.

The substituted thiazole derivative compounds are prepared by the general synthetic route described below in Scheme 2.

Referring to Scheme 2, condensation of BH and BI in polar-protic solvent at elevated temperature provides the cyclo-annulation product thiazole BJ. Treatment with electrophilic halide results in substitution to afford BK. Upon hydrolysis to provide acid BL, BL is coupled with various amines to give amide BN using amide coupling reagents. Compound BJ is prepared from aryl halides compound BN using palladium-mediated cross coupling conditions with boronic acids BC—B(OH)₂.

The substituted pyrimidinone derivative compounds are prepared by the general synthetic route described below in Scheme 3.

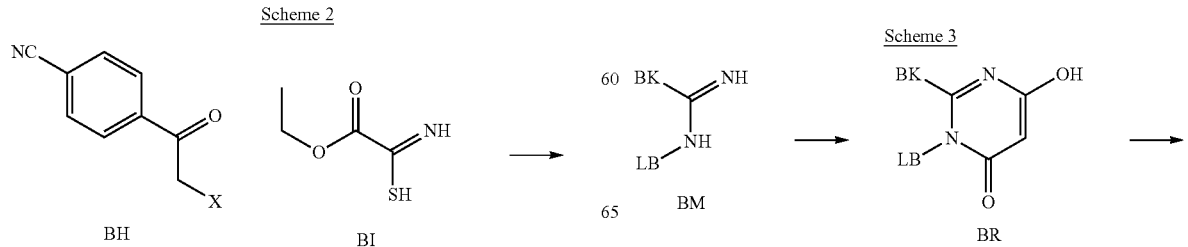

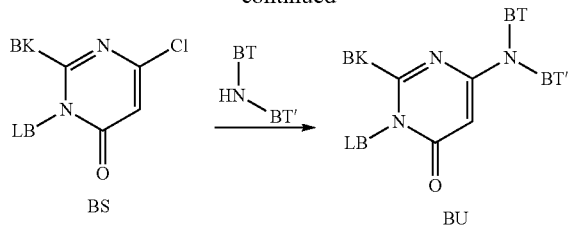

Referring to scheme 3, amidine BM reacts with an activated malonate such as bis(2,4,6-triphenyl)malonate, in an organic solvent such as toluene, and heated at an elevated temperature to give cyclized pyrimidinone intermediate BR. Chlorination of BR by a chlorinating reagent such as phosphorus oxychloride, provides BS. Chloro compound BS undergoes SNAr displacement with 1 equivalent of amine in an organic solvent such as DMF, in the presence of a base such as diisopropylethyl amine. Final product BU is obtained after removal of protective groups.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference in its entirety.

Accordingly, provided herein is a pharmaceutical composition comprising at least one substituted heterocyclic derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient.

One embodiment provides a pharmaceutical composition comprising a compound of Formula (II), or a pharmaceutically acceptable salt thereof, and a pharmaceutically acceptable excipient.

In certain embodiments, the substituted heterocyclic derivative compound as described by Formula (I) or (II) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Biology

Epigenetics is the study of heritable changes in gene expression caused by mechanisms other than the underlying DNA sequence. Molecular mechanisms that play a role in epigenetic regulation include DNA methylation and chromatin/histone modifications.

The genomes of eukaryotic organisms are highly organized within the nucleus of the cell. Tremendous compaction is required to package the 3 billion nucleotides of the human genome into the nucleus of a cell. Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can modify histones at various sites.

There are a total of six classes of histones (HI, H2A, H2B, H3, H4, and H5) organized into two groups: core histones (H2A, H2B, H3, and H4) and linker histones (HI and H5). The basic unit of chromatin is the nucleosome, which consists of about 147 base pairs of DNA wrapped around the core histone octamer, consisting of two copies each of the core histones H2A, H2B, H3, and H4.

Basic nucleosome units are then further organized and condensed by the aggregation and folding of nucleosomes to form a highly condensed chromatin structure. A range of different states of condensation are possible, and the tightness of chromatin structure varies during the cell cycle, being most compact during the process of cell division.

Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications acetylation, methylation, phosphorylation, ribosylation sumoylation, ubiquitination, citrullination, deimination, and biotinylation.

The core of histones H2A and H3 can also be modified. Histone modifications are integral to diverse biological processes such as gene regulation, DNA repair, and chromosome condensation.

Histone methylation is one of the most important chromatin marks; these play important roles in transcriptional regulation, DNA-damage response, heterochromatin formation and maintenance, and X-chromosome inactivation. A recent discovery also revealed that histone methylation affects the splicing outcome of pre-mRNA by influencing the recruitment of splicing regulators. Histone methylation includes mono-, di-, and tri-methylation of lysines, and mono-, symmetric di-, and asymmetric di-methylation of arginines. These modifications can be either an activating or repressing mark, depending on the site and degree of methylation.

Histone Demethylases

A "demethylase" or "protein demethylase," as referred to herein, refers to an enzyme that removes at least one methyl group from polypeptide. Demethylases comprise a JmjC domain, and can be a methyl-lysine or methyl-arginine demethylase. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found used a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

LSD-1

Lysine-specific demethylase 1 (LSD1) is a histone lysine demethylase that specifically demethylates monomethylated and demethylated histone H3 at K4 and also demethylates demethylated histone H3 at K9. Although the main target of LSD1 appears to be mono- and di-methylated histone lysines, specifically H3K4 and H3K9, there is evidence in the literature that LSD1 can demethylate methylated lysines on non-histone proteins like p53, E2F1, Dnmtl and STAT3.

LSD1 has a fair degree of structural similarity and amino acid identity/homology to polyamine oxidases and monoamine oxidases, all of which (i. e., MAO-A, MAO-B and LSD1) are flavin dependent amine oxidases which catalyze the oxidation of nitrogen-hydrogen bonds and/or nitrogen-carbon bonds. LSD1 also includes an N-terminal SWRIM domain. There are two transcript variants of LSD1 produced by alternative splicing.

Methods of Use

In some embodiments, the compounds disclosed herein are capable of inhibiting LSD1 activity in a biological sample by contacting the biological sample with a substituted heterocyclic compound as disclosed herein. In some embodiments, a substituted heterocyclic compound as disclosed herein is capable of modulating the level of histone 4 lysine 3 methylation in the biological sample. In some embodiments, a substituted heterocyclic compound as disclosed herein is capable of modulating histone-3 lysine-9 methylation levels in the biological sample.

In some embodiments, a substituted heterocyclic compound as disclosed herein inhibits LSD1 activity to a greater extent than MAO-A and/or MAO-B.

One embodiment provides a method of regulating gene transcription in a cell comprising inhibiting lysine-specific demethylase 1 activity by exposing the lysine-specific demethylase 1 enzyme to a compound of Formula (I).

One embodiment provides a method of regulating gene transcription in a cell comprising inhibiting lysine-specific demethylase 1 activity by exposing the lysine-specific demethylase 1 enzyme to a compound of Formula (II).

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation.

One embodiment provides a method of treating cancer in a patient in need thereof, comprising administering to the patient a compound of Formula (I), or a pharmaceutically acceptable salt thereof.

One embodiment provides a method of treating cancer in a patient in need thereof, comprising administering to the patient a compound of Formula (II), or a pharmaceutically acceptable salt thereof.

In a further embodiment is the method for treating cancer in a subject wherein the cancer is selected from prostate cancer, breast cancer, bladder cancer, lung cancer or melanoma.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm ($\delta$) and coupling constants, J are reported in Hertz. For proton spectra the solvent peak was used as the reference peak.

Example 1: 4-[2-(4-aminopiperidin-1-yl)-5-(1-methyl-1H-indazol-5-yl)-1,3-thiazol-4-yl]benzonitrile

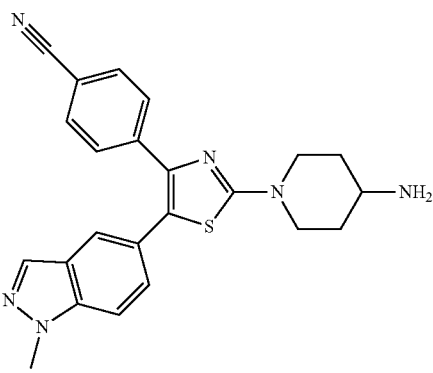 [SMILES: Cn1ncc2cc(-c3sc(N4CCC(N)CC4)nc3-c3ccc(C#N)cc3)ccc21]

Preparation 1A To a round-bottom flask charged with 4-(2-amino-1,3-thiazol-4-yl)benzonitrile (2.0 g, 10 mmol) in CCl$_4$ (50 mL) was added NBS (1.8 g, 10 mmol). The reaction was allowed to stir at room temperature for 2 hours. The heterogeneous mixture was filtered and the filter cake was washed with water and dried in vacuo to afford 4-(2-amino-5-bromo-1,3-thiazol-4-yl)benzonitrile (2.0 g, 71%) as an off-white solid. [M+H] Calc'd for C$_{10}$H$_6$BrN$_3$S, 281; Found, 281.

Preparation 1B To a round-bottom flask charged with t-BuONO (712 µL, 6 mmol) in ACN (20 mL) was added CuCl$_2$ (800 mg, 6 mmol). After 10 min, 2-amino-4-bromo-5-(4-benzonitrile)thiazole (1.12 g, 4 mmol) was added. The reaction was kept at 70° C. for 2 hours with vigorous stirring at which time the reaction was quenched with HCl (1N, 20 mL) followed by water. The heterogeneous solution was extracted with EtOAc and the combined organic layers were successively washed with brine, dried over Na$_2$SO$_4$, and concentrated in vacuo. The residue was purified by flash chromatography (33% EtOAc in hexanes) to give 4-(5-bromo-2-chloro-1,3-thiazol-4-yl)benzonitrile (1.1 g, 90%) as a beige solid.

Preparation 1C To a round bottom-flask charged with 4-(5-bromo-2-chloro-1,3-thiazol-4-yl)benzonitrile (1.2 g, 4 mmol) and piperidin-4-yl-carbamic acid tert-butyl ester (1.0 g, 5 mmol) in DMF (30 mL) was added DIEA (1.0 g, 8 mmol). The reaction was allowed to stir at 100° C. for 2 hours under inert atmosphere. Upon completion, the reaction was concentrated in vacuo and the residue purified by flash chromatography (30-50% gradient of EtOAc in hexanes) to afford tert-butyl N-{1-[5-bromo-4-(4-cyanophenyl)-1,3-thiazol-2-yl]piperidin-4-yl}carbamate (1.4 g, 80%) as a yellow solid. [M+H] Calc'd for C$_{20}$H$_{23}$BrN$_4$O$_2$S, 463; Found, 463.

Preparation 1D A vial was charged with tert-butyl N-{1-[5-bromo-4-(4-cyanophenyl)-1,3-thiazol-2-yl]piperidin-4-yl}carbamate (139 mg, 0.3 mmol), 1-methylindazole-5-boronic acid (64 mg, 0.36 mmol), Pd(dppf)Cl$_2$CH$_2$C$_{12}$ (25 mg, 0.03 mmol) and 2M Na$_2$CO$_3$ in 1,4-dioxane (10 mL). The mixture was purged with nitrogen for 2 min and allowed to stir at 120° C. 16 hrs. The crude reaction was concentrated in vacuo and the residue purified by flash chromatography (PE/EA=1/1~½) to afford a yellow solid. The solid was dissolved in DCM (10 mL) followed by the addition of TFA (1 mL) and allowed to stir at ambient temperature for 2 hours. The mixture was concentrated in vacuo and purified by prep-HPLC to afford the title compound as the HCl salt (25 mg, 31%) as a yellow solid. $^1$H NMR (400 MHz, CD$_3$OD): δ ppm 1.64-1.68 (2H, m), 2.00-2.04 (2H, m), 3.08-3.12 (2H, m), 3.21-3.22 (1H, m), 3.97 (3H, s), 4.07-4.10 (2H, m), 7.17-7.19 (1H, m), 7.43-7.52 (5H, m), 7.63 (1H, s), 7.89 (1H, s). LCMS (mobile phase: 5-95% Acetonitrile-Water-0.1% TFA): purity is >95%, Rt=2.934 min. [M+H] Calc'd for C$_{23}$H$_{22}$N$_6$S, 415; Found, 415.

Example 2: cis-4-(2-{decahydropyrrolo[3,4-d]azepin-6-yl}-5-(1-methyl-1H-indazol-5-yl)-1,3-thiazol-4-yl)benzonitrile

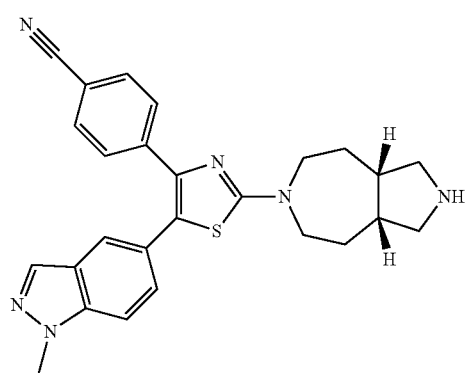 [SMILES: Cn1ncc2cc(-c3sc(N4CC[C@@H]5CNC[C@@H]5CC4)nc3-c3ccc(C#N)cc3)ccc21]

The title compound was prepared in 45% yield starting with cis-2-BOC-octahydropyrrolo[3,4-d]azepine hydrochloride and 1-methylindazole-5-boronic acid according to the procedure for the preparation of Example 1C and 1D. $^1$H NMR (400 MHz, CD$_3$OD): δ ppm 1.64-1.68 (2H, m), 2.00-2.04 (2H, m), 3.08-3.12 (2H, m), 3.21-3.22 (1H, m), 3.97 (3H, s), 4.07-4.10 (2H, m), 7.17-7.19 (1H, m), 7.43-7.52 (5H, m), 7.63 (1H, s), 7.89 (1H, s). LCMS (mobile phase: 5-95% Acetonitrile-Water-0.1% TFA): purity is >95%, Rt=2.934 min. [M+H] Calc'd for C$_{23}$H$_{22}$N$_6$S, 415; Found, 415.

Example 3: 4-[2-(4-aminopiperidin-1-yl)-5-{1-methyl-1H-pyrrolo[2,3-b]pyridin-5-yl}-1,3-thiazol-4-yl]benzonitrile

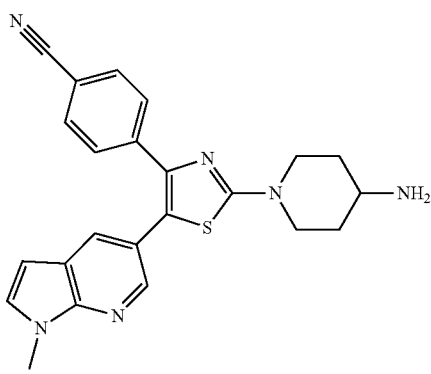 [SMILES: Cn1ccc2cc(-c3sc(N4CCC(N)CC4)nc3-c3ccc(C#N)cc3)cnc21]

The title compound was prepared in 15% overall yield according to the general procedure for the preparation of Example 1. $^1$H NMR (400 MHz, CD$_3$OD): δ ppm 1.79-1.73 (2H, m), 2.10-2.13 (2H, m), 3.17-3.24 (2H, m), 3.39-3.43 (1H, m), 3.85 (3H, s), 4.16-4.19 (2H, m), 6.47 (1H, s), 7.41

(1H, s), 7.55-7.60 (4H, m), 7.89 (1H, s), 8.06 (1H, s). LCMS (mobile phase: 5-95% Acetonitrile-Water-0.1% TFA): purity is >95%, Rt=2.904 min. [M+H] Calc'd for C$_{23}$H$_{22}$N$_6$S, 414; Found, 414.

Example 4: 4-[2-(4-aminopiperidin-1-yl)-5-{1-methyl-1H-pyrazolo[3,4-b]pyridin-5-yl}-1,3-thiazol-4-yl]benzonitrile

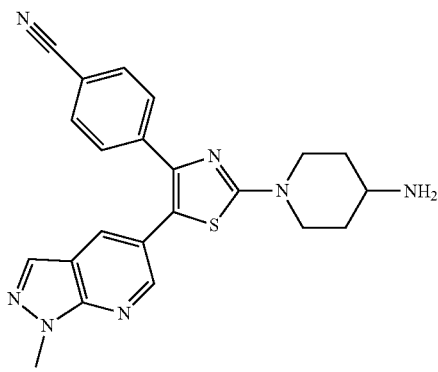 [SMILES: Cn1ncc2cc(-c3sc(N4CCC(N)CC4)nc3-c3ccc(C#N)cc3)cnc21]

The title compound was prepared in 23% overall yield according to the general procedure for the preparation of Example 1. $^1$H NMR (400 MHz, DMSO-d$_6$): δ ppm 1.62-1.66 (2H, m), 2.02-2.05 (2H, m), 3.16-3.22 (2H, m), 3.21-3.22 (1H, m), 3.99-4.02 (2H, m), 4.06 (3H, s), 7.55-7.57 (2H, d, J=8.0 Hz), 7.73-7.75 (2H, d, J=8.0 Hz), 7.88-7.95 (2H, bs), 8.16 (1H, s), 8.22 (1H, s), 8.39 (1H, s). LCMS (mobile phase: 5-95% Acetonitrile-Water-0.1% TFA): purity is >95%, Rt=2.822 min. [M+H] Calc'd for C$_{22}$H$_{21}$N$_7$S, 415; Found, 415.

Example 5: 4-(2-{2,8-diazaspiro[4.5]decan-8-yl}-5-(1-methyl-1H-indazol-5-yl)-1,3-thiazol-4-yl)benzonitrile

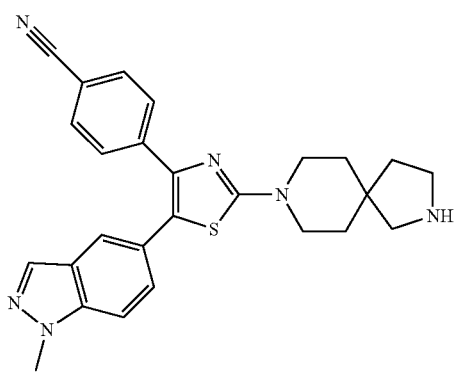 [SMILES: Cn1ncc2cc(-c3sc(N4CCC5(CCNC5)CC4)nc3-c3ccc(C#N)cc3)ccc21]

The title compound was prepared in 23% overall yield according to the general procedure for the preparation of Example 1. $^1$H NMR (300 MHz, CD$_3$OD): δ ppm 1.81-1.84 (4H, m), 2.03-2.08 (2H, m), 3.21-3.22 (2H, m), 3.42-3.47 (2H, m), 3.59-3.64 (4H, m), 4.08 (3H, s), 7.26-7.30 (1H, m), 7.52-7.62 (5H, m), 7.72 (1H, s), 7.99 (1H, s). LCMS (mobile phase: 5-95% Acetonitrile-Water-0.1% TFA): purity is >95%, Rt=3.098 min. [M+H] Calc'd for C$_{26}$H$_{26}$N$_6$S, 454; Found, 454.

Example 6: 4-[5-(1-methyl-1H-indazol-5-yl)-2-{octahydro-1H-pyrrolo[3,2-c]pyridin-5-yl})-1,3-thiazol-4-yl]benzonitrile

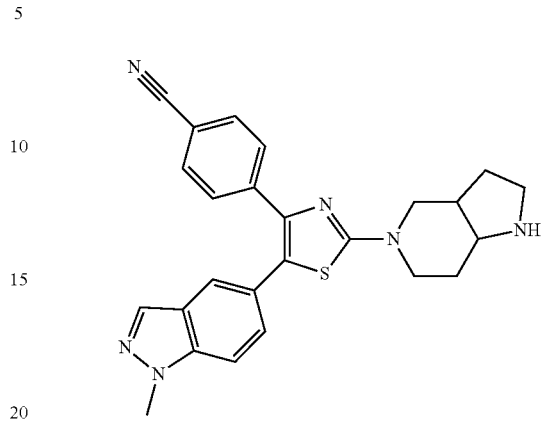

The title compound was prepared in 21% overall yield according to the general procedure for the preparation of Example 1. $^1$H NMR (400 MHz, CD$_3$OD): δ ppm 1.98-2.09 (2H, m), 2.16-2.27 (2H, m), 2.69-2.72 (1H, m), 3.36-3.43 (2H, m), 3.51-3.53 (1H, m), 3.71-3.76 (1H, m), 3.83-3.88 (1H, m), 3.94-3.99 (2H, m), 4.09 (3H, s), 7.29-7.32 (1H, m), 7.55-7.64 (5H, m), 7.75 (1H, s), 8.01 (1H, s). LCMS (mobile phase: 5-95% Acetonitrile-Water-0.02% NH$_4$OAc): purity is >95%, Rt=3.621 min. [M+H] Calc'd for C$_{25}$H$_{24}$N$_6$S, 441; Found, 441.

Example 7: 4-[5-(1-methyl-1H-indazol-5-yl)-2-{octahydro-1H-pyrrolo[3,4-c]pyridin-5-yl})-1,3-thiazol-4-yl]benzonitrile

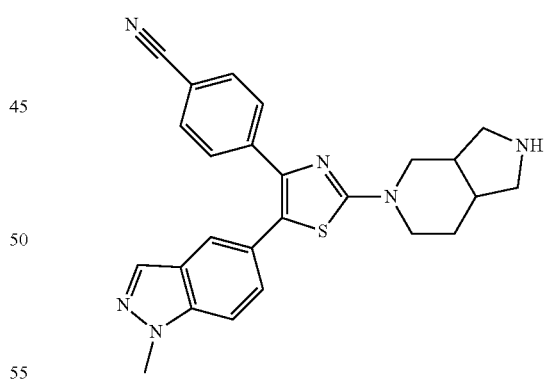

The title compound was prepared in 39% overall yield according to the general procedure for the preparation of Example 1. $^1$H NMR (400 MHz, CD$_3$OD): δ ppm 1.58-1.61 (1H, m), 1.84-1.88 (1H, m), 2.52-2.63 (2H, m), 3.05-3.11 (2H, m), 3.14-3.18 (1H, m), 3.29-3.34 (1H, m), 3.37-3.42 (1H, m), 3.50-3.55 (1H, m), 3.72-3.75 (1H, m), 3.81-3.85 (1H, m), 3.97 (3H, s), 7.14-7.17 (1H, m), 7.41-7.49 (5H, m), 7.60 (1H, s), 7.87 (1H, s). LCMS (mobile phase: 5-95% Acetonitrile-Water-0.1% TFA): purity is >95%, Rt=3.004 min. [M+H] Calc'd for C$_{25}$H$_{24}$N$_6$S, 441; Found, 441.

Example 8: 4-[2-(4-aminopiperidin-1-yl)-5-(1-methyl-1H-1,3-benzodiazol-5-yl)-1,3-thiazol-4-yl]benzonitrile

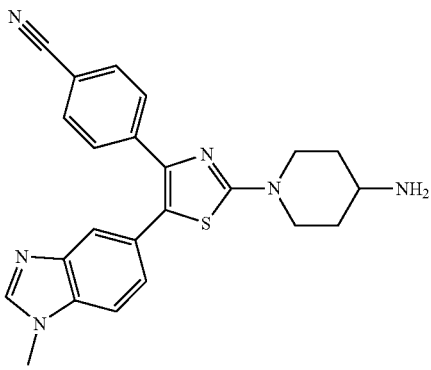 [SMILES: Cn1cnc2cc(-c3sc(N4CCC(N)CC4)nc3-c3ccc(C#N)cc3)ccc21]

The title compound was prepared in 12% overall yield according to the general procedure for the preparation of Example 1. $^1$H NMR (400 MHz, CD$_3$OD): δ ppm 1.75-1.84 (2H, m), 2.15-2.17 (2H, m), 3.23-3.30 (2H, m), 3.43-3.49 (1H, m), 4.16 (3H, s), 4.19-4.23 (2H, m), 7.55-7.58 (1H, dd, J=1.6, 8.8 Hz), 7.60-7.64 (4H, m), 7.74 (1H, d, J=0.4 Hz), 7.89-7.91 (1H, dd, J=1.6, 8.8 Hz), 9.04 (1H, s). LCMS (mobile phase: 5-95% Acetonitrile-Water-0.1% TFA): purity is >95%, Rt=2.380 min. [M+H] Calc'd for C$_{23}$H$_{22}$N$_6$S, 414; Found, 414.

Example 9: 4-[2-(4-aminopiperidin-1-yl)-5-{3-methyl-3H-imidazo[4,5-b]pyridin-6-yl}-1,3-thiazol-4-yl]benzonitrile

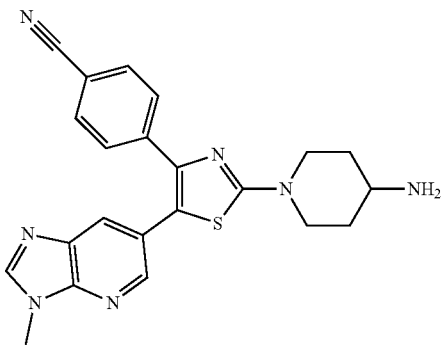 [SMILES: Cn1cnc2cc(-c3sc(N4CCC(N)CC4)nc3-c3ccc(C#N)cc3)cnc21]

The title compound was prepared in 49% overall yield according to the general procedure for the preparation of Example 1. $^1$H NMR (400 MHz, CD$_3$OD): δ ppm 1.77-1.81 (2H, m), 2.15-2.18 (2H, m), 3.23-3.33 (2H, m), 3.43-3.48 (1H, m), 4.04 (3H, s), 4.20-4.24 (2H, m), 7.60-7.65 (4H, m), 8.07 (1H, d, J=2.0 Hz), 8.42 (1H, d, J=1.6 Hz), 8.97 (1H, s). LCMS (mobile phase: 5-95% Acetonitrile-Water-0.1% TFA): purity is >95%, Rt=2.400 min. [M+H] Calc'd for C$_{22}$H$_{21}$N$_7$S, 415; Found, 415.

Example 10: cis-4-(2-{decahydropyrrolo[3,4-d]azepin-6-yl}-5-(1-methyl-1H-1,3-benzodiazol-5-yl)-1,3-thiazol-4-yl)benzonitrile

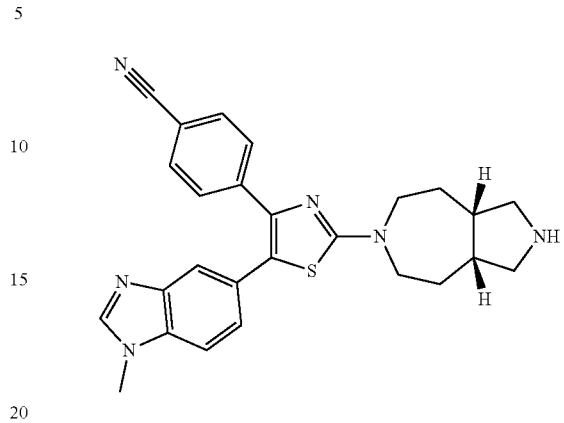

The title compound was prepared in 34% overall yield according to the general procedure for the preparation of Example 1. $^1$H NMR (400 MHz, CD$_3$OD): δ ppm 1.76-1.79 (4H, m), 2.63-2.68 (2H, m), 2.93-2.98 (2H, m), 3.47-3.57 (4H, m), 3.75-3.79 (2H, m), 4.18 (3H, s), 7.54-7.57 (1H, m), 7.62 (1H, s), 7.80-7.81 (2H, m), 7.85-7.88 (2H, m), 8.00-9.02 (1H, m), 9.40 (1H, s). LCMS (mobile phase: 5-95% Acetonitrile-Water-0.1% TFA): purity is >95%, Rt=2.401 min. [M+H] Calc'd for C$_{26}$H$_{26}$N$_6$S, 454; Found, 454.

Example 11: cis-4-(2-{decahydropyrrolo[3,4-d]azepin-6-yl}-5-{1-methyl-1H-pyrazolo[3,4-b]pyridin-5-yl}-1,3-thiazol-4-yl)benzonitrile

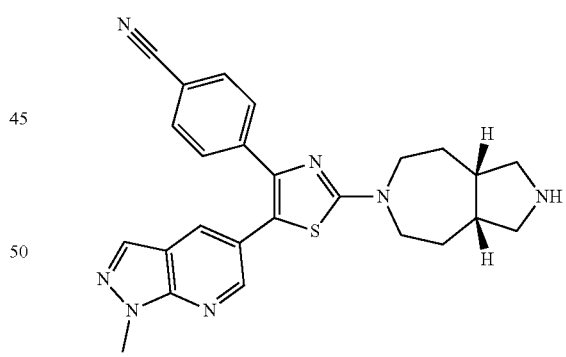

The title compound was prepared in 17% overall yield according to the general procedure for the preparation of Example 1. $^1$H NMR (400 MHz, CD$_3$OD): δ ppm 1.86-1.91 (2H, m), 1.95-1.99 (2H, m), 2.55-2.56 (2H, m), 2.64-2.68 (2H, m), 3.28-3.30 (2H, m), 3.45-3.51 (2H, m), 4.02-4.06 (2H, m), 4.11 (3H, s), 7.59-7.60 (4H, m), 8.07 (1H, s), 8.14 (1H, d, J=2.0 Hz), 8.35 (1H, d, J=2.0 Hz). LCMS (mobile phase: 5-95% Acetonitrile-Water-0.1% TFA): purity is >95%, Rt=2.883 min. [M+H] Calc'd for C$_{25}$H$_{25}$N$_7$S, 455; Found, 455.

Example 12: 4-[2-(4-aminopiperidin-1-yl)-5-[1-(2,2,2-trifluoroethyl)-1H-pyrazol-4-yl]-1,3-thiazol-4-yl]benzonitrile

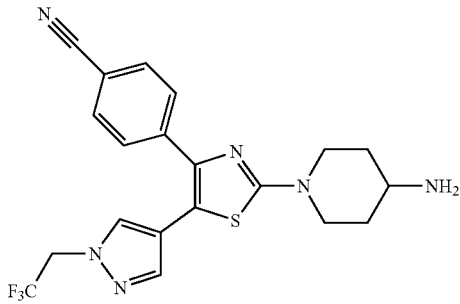 [SMILES: N#Cc1ccc(-c2nc(N3CCC(N)CC3)sc2-c2cnn(CC(F)(F)F)c2)cc1]

The title compound was prepared in 38% overall yield according to the general procedure for the preparation of Example 1. $^1$H NMR (400 MHz, CD$_3$OD): δ ppm 1.73-1.77 (2H, m), 2.11-2.14 (2H, m), 3.18-3.25 (2H, m), 3.41-3.45 (1H, m), 4.15-4.18 (2H, m), 4.94-4.98 (2H, m), 7.49 (1H, d, J=2.0 Hz), 7.67-7.69 (2H, d, J=8.4 Hz), 7.73-7.75 (2H, d, J=8.4 Hz), 7.77 (1H, d, J=2.0 Hz). LCMS (mobile phase: 5-95% Acetonitrile-Water-0.1% TFA): purity is >95%, Rt=2.963 min. [M+H] Calc'd for C$_{20}$H$_{19}$F3N$_6$S, 432; Found, 432.

Example 13: 4-(2-{decahydropyrrolo[3,4-d]azepin-6-yl}-5-[1-(2,2,2-trifluoroethyl)-1H-pyrazol-4-yl]-1,3-thiazol-4-yl)benzonitrile

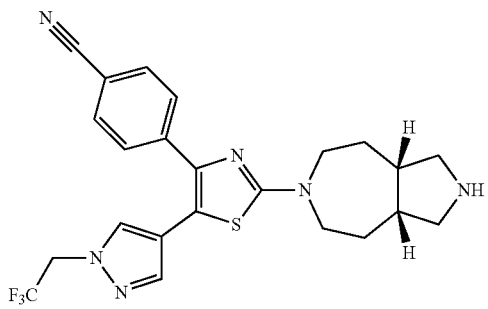 [SMILES: N#Cc1ccc(-c2nc(N3CC[C@@H]4CNC[C@@H]4CC3)sc2-c2cnn(CC(F)(F)F)c2)cc1]

The title compound was prepared in 41% overall yield according to the general procedure for the preparation of Example 1. $^1$H NMR (400 MHz, CD$_3$OD): δ ppm 1.98-2.02 (4H, m), 2.74-2.76 (2H, m), 3.02-3.06 (2H, m), 4.51-4.57 (4H, m), 3.97-4.01 (2H, m), 4.91-4.93 (2H, m), 7.46 (1H, s), 7.68-7.74 (4H, m), 7.76 (1H, s). LCMS (mobile phase: 5-95% Acetonitrile-Water-0.1% TFA): purity is >95%, Rt=2.967 min. [M+H] Calc'd for C$_{23}$H$_{23}$F3N$_6$S, 472; Found, 472.

Example 14: 4-[2-(4-aminopiperidin-1-yl)-5-[1-(cyclopropylmethyl)-1H-pyrazol-4-yl]-1,3-thiazol-4-yl]benzonitrile

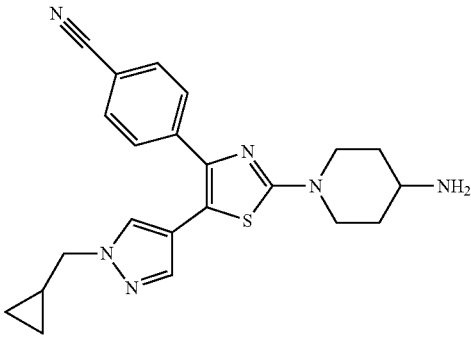 [SMILES: N#Cc1ccc(-c2nc(N3CCC(N)CC3)sc2-c2cnn(CC3CC3)c2)cc1]

The title compound was prepared in 18% overall yield according to the general procedure for the preparation of Example 1. $^1$H NMR (400 MHz, CD$_3$OD): δ ppm 0.37-0.40 (2H, m), 0.60-0.63 (2H, m), 1.27-1.31 (1H, m), 1.54-1.58 (2H, m), 1.98-2.01 (2H, m), 3.01-3.06 (1H, m), 3.12-3.18 (2H, m), 3.98-4.00 (2H, m), 4.04-4.07 (2H, m), 7.38 (1H, d, J=2.0 Hz), 7.67-7.69 (3H, m), 7.75-7.77 (2H, d, J=8.4 Hz). LCMS (mobile phase: 5-95% Acetonitrile-Water-0.1% TFA): purity is >95%, Rt=2.937 min. [M+H] Calc'd for C$_{22}$H$_{24}$N$_6$S, 404; Found, 404.

Example 15: 4-{5-[1-(cyclopropylmethyl)-1H-pyrazol-4-yl]-2-{decahydropyrrolo[3,4-d]azepin-6-yl}-1,3-thiazol-4-yl}benzonitrile The title compound was prepared in 13% overall yield according to the general procedure for the preparation of Example 1. $^1$H NMR (400 MHz, CD$_3$OD): δ ppm 0.37-0.40 (2H, m), 0.60-0.63 (2H, m), 1.27-1.31 (1H, m), 1.98-2.08 (4H, m), 2.73-2.77 (2H, m), 3.04-3.08 (2H, m), 3.52-3.62 (4H, m), 3.97-4.02 (4H, m), 7.37 (1H, s), 7.70 (1H, s), 7.75 (4H, m). LCMS (mobile phase: 5-95% Acetonitrile-Water-0.1% TFA): purity is >95%, Rt=2.906 min. [M+H] Calc'd for C$_{25}$H$_{28}$N$_6$S, 444; Found, 444.

Example 16: 4-{2-[(3R)-3-aminopiperidine-1-carbonyl]-5-(1-methyl-1H-1,3-benzodiazol-5-yl)-1,3-thiazol-4-yl}benzonitrile

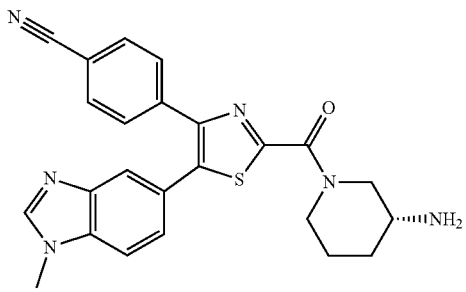 [SMILES: Cn1cnc2cc(-c3sc(C(=O)N4CCC[C@@H](N)C4)nc3-c3ccc(C#N)cc3)ccc21]

Preparation 16A. A mixture containing 4-(2-bromoacetyl)benzonitrile (4.48 g, 20 mmol), ethyl carbamothioylformate (2.66 g, 20 mmol) in absolute ethanol (50 mL) was allowed to stir at 80° C. for 16 hrs under $N_2$ atmosphere. The resulting slurry was poured into saturated $NaHCO_3$. The precipitate was filtered, washed with water, and dried in vacuo afford ethyl 4-(4-cyanophenyl)-1,3-thiazole-2-carboxylate (4.6 g, 88%) as a white solid. [M+H] Calc'd for $C_{13}H_{10}N_2O_2S$, 259; Found, 259.

Preparation 16B. A mixture containing ethyl 4-(4-cyanophenyl)-1,3-thiazole-2-carboxylate (2.58 g, 10 mmol) in AcOH (50 mL), potassium acetate (4.9 g, 50 mmol), was added $Br_2$ (8.0 g, 50 mmol) at ambient temperature. The reaction was heated 100° C. for 12 hours. Upon completion, the slurry was poured into saturated $NaHSO_3$. The heterogeneous solution was filtered, and the filter cake washed water, and dried in vacuo to afford ethyl 5-bromo-4-(4-cyanophenyl)-1,3-thiazole-2-carboxylate (1.8 g, 70%). [M+H] Calc'd for $C_{13}H_9BrN_2O_2S$, 338; Found, 338.

Preparation 16C. To a round-bottom flask charged with ethyl 5-bromo-4-(4-cyanophenyl)-1,3-thiazole-2-carboxylate (1.3 g, 3.9 mmol) in THF (20 mL) was added LiOH (1.6 g, 39 mmol) in water (5 mL). The mixture was then heated to 40° C. for 2 hours. The pH was adjusted to 3-4 with HCl (1N) and filtered. The solid was washed with dichloromethane, dried in vacuo to afford 5-bromo-4-(4-cyanophenyl)-1,3-thiazole-2-carboxylic acid (1.1 g, 91%). [M+H] Calc'd for $C_{11}H_5BrN_2O_2S$, 310; Found, 310.

Preparation 16D. To a mixture containing 5-bromo-4-(4-cyanophenyl)-1,3-thiazole-2-carboxylic acid (150 mg, 0.5 mmol) in DMF (30 mL), N-((3R)(3-piperidyl))(tert-butoxy)carboxamide (150 mg, 0.75 mmol), DIEA (390 mg, 3 mmol) was added HATU (190 mg, 0.5 mmol). The reaction was stirred under nitrogen atmosphere for 4 hours. The reaction mixture was poured into water and filtered. The filter cake was washed with water and dried in vacuo to give tert-butyl N-[(3R)-1-[5-bromo-4-(4-cyanophenyl)-1,3-thiazole-2-carbonyl]piperidin-3-yl]carbamate (150 mg, 51%). [M+H] Calc'd for $C_{21}H_{23}BrN_4O_3S$, 492; Found, 492.

Preparation 16E. A vial charged with tert-butyl N-[(3R)-1-[5-bromo-4-(4-cyanophenyl)-1,3-thiazole-2-carbonyl]piperidin-3-yl]carbamate (147 mg, 0.3 mmol)) in 1,4-dioxane (10 mL), 1-methyl-5-(tetramethyl-1,3,2-dioxaborolan-2-yl)-1H-1,3-benzodiazole (93 mg, 0.36 mmol), Pd(dppf)$Cl_2CH_2C_{12}$ (25 mg, 0.03 mmol) and $Na_2CO_3$ (1 mL, 2M) was purged with nitrogen for 2 min. The mixture was sealed and allowed to stir at 120° C. for 16 hrs. Upon completion, the reaction was concentrated in vacuo and the residue purified by flash chromatography (PE/EA=1/1~½) to afford compound tert-butyl N-[(3R)-1-[4-(4-cyanophenyl)-5-(1-methyl-1H-1,3-benzodiazol-5-yl)-1,3-thiazole-2-carbonyl]piperidin-3-yl]carbamate (130 mg, 80%) as a yellow solid. [M+H] Calc'd for $C_{29}H_{30}N_6O_3S$, 543; Found, 543.

Preparation 16F. To a round-bottom flask charge with tert-butyl N-[(3R)-1-[4-(4-cyanophenyl)-5-(1-methyl-1H-1,3-benzodiazol-5-yl)-1,3-thiazole-2-carbonyl]piperidin-3-yl]carbamate (130 mg, 0.24 mmol) in DCM (10 mL) was added TFA (1 mL). The reaction was allowed to stir at ambient temperature for 2 hours. The mixture was concentrated in vacuo and the residue purified by prep-HPLC to afford the title compound as the trifluoroacetic acid salt (102 mg, 76%) as a light yellow solid. $^1$H NMR (400 MHz, DMSO-$d_6$): δ 1.61-1.68 (2H, m), 1.83-1.88 (1H, m), 2.05-2.08 (1H, m), 3.32-3.39 (2H, m), 3.80-3.83 (1H, m), 3.84 (3H, s), 4.33-4.35 (1H, m), 4.77-4.80 (1H, m), 7.43-7.47 (1H, m), 7.60-7.69 (2H, m), 7.81-7.88 (4H, m), 8.14 (3H, br), 9.01 (1H, s). LCMS (mobile phase: 5-95% Acetonitrile-Water-0.1% TFA): purity is >95%, Rt=2.364 min. [M+H] Calc'd for $C_{24}H_{22}N_6OS$, 443; Found, 443.

Example 17: 4-{2-[(3 S)-3-aminopiperidine-1-carbonyl]-5-(1-methyl-1H-1,3-benzodiazol-5-yl)-1,3-thiazol-4-yl}benzonitrile

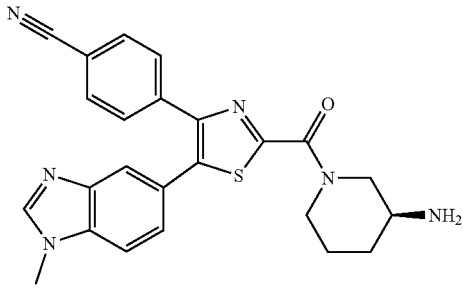 [SMILES: Cn1cnc2cc(-c3sc(C(=O)N4CCC[C@H](N)C4)nc3-c3ccc(C#N)cc3)ccc21]

The title compound was prepared as the TFA salt in 25% overall yield according to the general procedure for the preparation of Example 16. $^1$H NMR (400 MHz, DMSO-$d_6$): δ 1.61-1.68 (2H, m), 1.83-1.88 (1H, m), 2.05-2.08 (1H, m), 3.32-3.39 (2H, m), 3.80-3.83 (1H, m), 3.84 (3H, s), 4.33-4.35 (1H, m), 4.77-4.80 (1H, m), 7.43-7.47 (1H, m), 7.60-7.69 (2H, m), 7.81-7.88 (4H, m), 8.14 (3H, br), 9.01 (1H, s). LCMS (mobile phase: 5-95% Acetonitrile-Water-0.1% TFA): purity is >95%, Rt=2.360 min. [M+H] Calc'd for $C_{24}H_{22}N_6OS$, 443; Found, 443.

Example 18: 4-[2-(4-aminopiperidine-1-carbonyl)-5-(1-methyl-1H-1,3-benzodiazol-5-yl)-1,3-thiazol-4-yl]benzonitrile

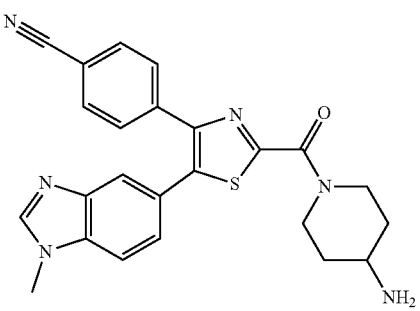 [SMILES: Cn1cnc2cc(-c3sc(C(=O)N4CCC(N)CC4)nc3-c3ccc(C#N)cc3)ccc21]

The title compound was prepared as the TFA salt in 20% overall yield according to the general procedure for the preparation of Example 16. $^1$H NMR (400 MHz, CD$_3$OD): δ ppm 1.68-1.80 (2H, m), 2.20-2.23 (2H, m), 2.89-3.11 (1H, m), 3.39-3.57 (2H, m), 4.17 (3H, s), 4.75-4.78 (1H, m), 5.69-5.73 (1H, m), 7.64-7.70 (5H, m), 7.91 (1H, s), 7.97 (1H, d, J=8.8 Hz) 9.34 (1H, s). LCMS (mobile phase: 10-80% Acetonitrile-Water-0.1% TFA): purity is >95%, Rt=2.214 min. [M+H] Calc'd for C$_{24}$H$_{22}$N$_6$OS, 443; Found, 443.

Example 19: 4-{2-[(3R)-3-aminopiperidine-1-carbonyl]-5-(4-methylphenyl)-1,3-thiazol-4-yl}benzonitrile

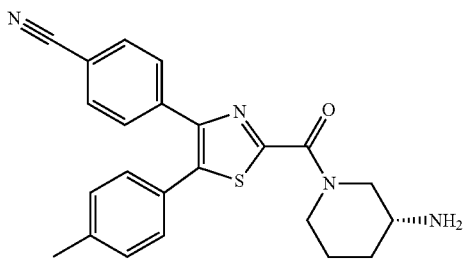 [SMILES: Cc1ccc(-c2sc(C(=O)N3CCC[C@@H](N)C3)nc2-c2ccc(C#N)cc2)cc1]

The title compound was prepared as the TFA salt in 21% overall yield according to the general procedure for the preparation of Example 16. $^1$H NMR (400 MHz, DMSO-d$_6$): δ 1.62-1.67 (2H, m), 1.83-1.87 (1H, m), 2.02-2.04 (1H, m), 2.35 (3H, s), 3.31-3.35 (2H, m), 3.80-3.83 (1H, m), 4.33-4.35 (1H, m), 4.80-4.85 (1H, m), 7.12-7.13 (1H, m), 7.26-7.31 (3H, m), 7.61-7.63 (1H, m), 7.67-7.70 (1H, m), 7.85 (2H, d, J=8.4 Hz), 8.04 (3H, br). LCMS (mobile phase: 5-95% Acetonitrile-Water-0.1% TFA): purity is >95%, Rt=3.311 min. [M+H] Calc'd for C$_{23}$H$_{22}$N$_4$OS, 403; Found, 403.

Example 20: 4-{2-[(3R)-3-aminopiperidine-1-carbonyl]-5-{3-methyl-3H-imidazo[4,5-b]pyridin-6-yl}-1,3-thiazol-4-yl}benzonitrile

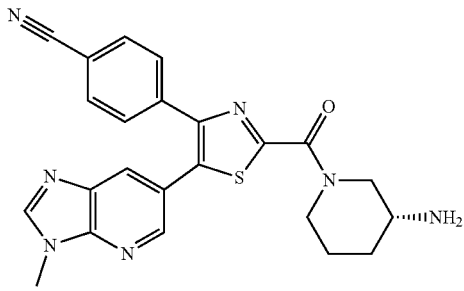 [SMILES: Cn1cnc2cc(-c3sc(C(=O)N4CCC[C@@H](N)C4)nc3-c3ccc(C#N)cc3)cnc21]

The title compound was prepared as the TFA salt in 18% overall yield according to the general procedure for the preparation of Example 16. $^1$H NMR (400 MHz, DMSO-d$_6$): δ 1.61-1.68 (2H, m), 1.84-1.89 (1H, m), 2.04-2.08 (1H, m), 3.29-3.38 (2H, m), 3.80-3.83 (1H, m), 4.30-4.35 (1H, m), 4.74-4.80 (1H, m), 7.61-7.77 (2H, m), 7.82 (2H, d, J=8.0 Hz), 8.14 (3H, br), 8.18-8.20 (1H, m), 8.36-8.38 (1H, m), 8.61 (1H, s). LCMS (mobile phase: 10-80% Acetonitrile-Water-0.1% TFA): purity is >95%, Rt=2.456 min. [M+H] Calc'd for C$_{23}$H$_{21}$N$_0$OS, 444; Found, 444.

Example 21: 4-{2-[(3R)-3-aminopiperidine-1-carbonyl]-5-[1-(2,2,2-trifluoroethyl)-1H-pyrazol-4-yl]-1,3-thiazol-4-yl}benzonitrile

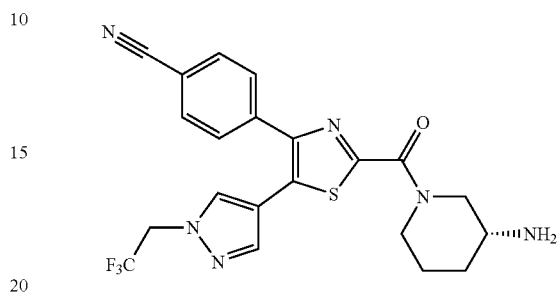

The title compound was prepared as the TFA salt in 22% overall yield according to the general procedure for the preparation of Example 16. $^1$H NMR (400 MHz, DMSO-d$_6$): δ 1.58-1.65 (2H, m), 1.80-1.85 (1H, m), 2.02-2.05 (1H, m), 3.30-3.32 (2H, m), 3.78-3.83 (1H, m), 4.28-4.31 (1H, m), 4.71-4.89 (1H, m), 5.14-5.21 (2H, m), 7.73-7.75 (2H, m), 7.80-7.82 (1H, m), 7.91 (2H, d, J=8.4 Hz), 8.07 (4H, br). LCMS (mobile phase: 5-95% Acetonitrile-Water-0.1% TFA): purity is >95%, Rt=2.982 min. [M+H] Calc'd for C$_{21}$H$_{19}$F3N$_6$OS, 461; Found, 461.

Example 22: 4-{2-[(3R)-3-aminopiperidine-1-carbonyl]-5-[1-(cyclopropylmethyl)-1H-pyrazol-4-yl]-1,3-thiazol-4-yl}benzonitrile

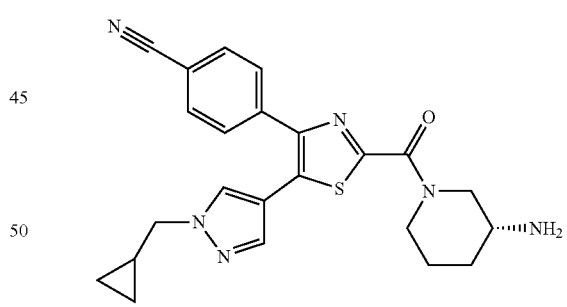

The title compound was prepared as the TFA salt in 26% overall yield according to the general procedure for the preparation of Example 16. $^1$H NMR (400 MHz, CD$_3$OD): δ 0.40-0.41 (2H, m), 0.63-0.65 (2H, m), 1.35-1.40 (1H, m), 1.59-1.64 (2H, m), 1.80-1.84 (1H, m), 2.03-2.06 (1H, m), 3.33-3.35 (2H, m), 4.02-4.04 (3H, m), 4.28-4.40 (1H, m), 4.71-4.89 (1H, m), 7.51-7.53 (1H, m), 7.79-7.88 (5H, m). LCMS (mobile phase: 5-95% Acetonitrile-Water-0.1% TFA): purity is >95%, Rt=3.002 min. [M+H] Calc'd for C$_{23}$H$_{24}$N$_6$OS, 433; Found, 433.

Example 23: 4-[2-(4-aminopiperidin-1-yl)-5-(3-hydroxy-3-methylbut-1-yn-1-yl)-1,3-thiazol-4-yl]benzonitrile

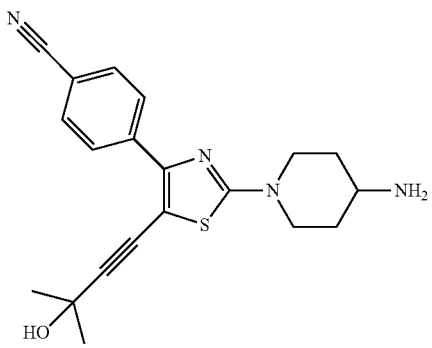 [SMILES: CC(C)(O)C#Cc1sc(N2CCC(N)CC2)nc1-c1ccc(C#N)cc1]

To a vial charged with tert-butyl N-{1-[5-bromo-4-(4-cyanophenyl)-1,3-thiazol-2-yl]piperidin-4-yl}carbamate (463 mg, 1 mmol) in DCM (10 mL) was added TFA (2 mL). The mixture was stirred at ambient temperature for 2 hrs. The reaction was concentrated in vacuo and the crude 4-[2-(4-aminopiperidin-1-yl)-5-bromo-1,3-thiazol-4-yl]-2-fluorobenzonitrile, TFA salt was used in the next step without further purification. To a vial charged with the crude 4-[2-(4-aminopiperidin-1-yl)-5-bromo-1,3-thiazol-4-yl]-2-fluorobenzonitrile, TFA salt in acetonitrile (10 mL) was added 2-methyl-but-3-yn-2-ol (252 mg, 3 mmol), PdCl$_2$(ACN)$_2$ (7 mg, 0.025 mmol), X-Phos (24 mg, 0.05 mmol), and K$_2$CO$_3$ (552 mg, 4 mmol). The reaction was purged with nitrogen and stirred at 80° C. overnight. Upon completion, the reaction was filtered, and the filtrate concentrated in vacuo. The residue was purified by prep-HPLC to afford the title compound (41 mg, 11%) as a yellow solid. $^1$H NMR (400 MHz, DMSO-d$_6$): δ 1.28-1.31 (2H, m), 1.48 (6H, s), 1.70-1.78 (2H, m), 1.81-1.82 (2H, m), 2.83 (1H, m), 3.13-3.19 (2H, m), 3.84-3.88 (2H, m), 5.58 (1H, s), 7.89 (2H, d, J=8.4 Hz), 8.29 (2H, d, J=8.0 Hz). LCMS (mobile phase: 30-95% Acetonitrile-Water-0.1% NH$_4$OH): purity is >95%, Rt=3.744 min, [M+H] Calc'd for C$_{20}$H$_{22}$N$_4$OS, 367; Found, 367.

Example 24: 4-[2-(4-aminopiperidin-1-yl)-5-(3-hydroxy-3-cyclopentylprop-1-yn-1-yl)-1,3-thiazol-4-yl]benzonitrile

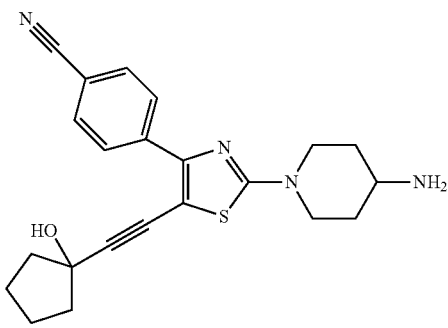 [SMILES: N#Cc1ccc(-c2nc(N3CCC(N)CC3)sc2C#CC2(O)CCCC2)cc1]

The title compound was prepared in 21% yield according to the procedure for the preparation of Example 23. $^1$H NMR (400 MHz, DMSO-d$_6$): δ 1.28-1.29 (2H, m), 1.61-1.81 (8H, m), 1.85-1.92 (4H, m), 2.83 (1H, m), 3.13-3.19 (2H, m), 3.84-3.89 (2H, m), 5.44 (1H, s), 7.89 (2H, d, J=8.4 Hz), 8.29 (2H, d, J=8.8 Hz). LCMS (mobile phase: 40-95% Acetonitrile-Water-0.1% NH$_4$OH): purity is >95%, Rt=3.838 min. [M+H] Calc'd for C$_{22}$H$_{24}$N$_4$OS, 393; Found, 393.

Example 25: 4-[2-(4-aminopiperidin-1-yl)-5-{3-methyl-3H-imidazo[4,5-b]pyridin-6-yl}-1,3-thiazol-4-yl]-2-fluorobenzonitrile

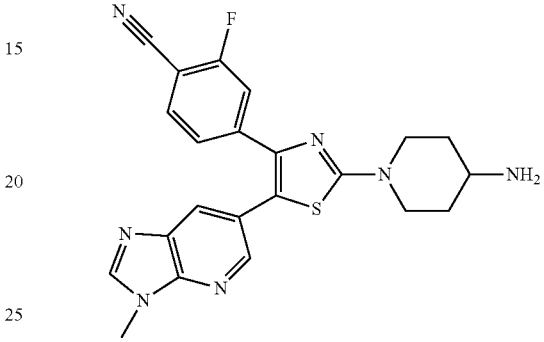

The title compound was prepared as the TFA salt in 76% overall yield according to the general procedure for the preparation of Example 1. $^1$H NMR (400 MHz, CD$_3$OD): δ 1.77-1.81 (m, 2H), 2.18 (d, J=10.4 Hz, 2H), 3.27-3.36 (m, 2H), 3.44-3.51 (m, 1H), 4.17 (s, 3H), 4.24 (d, J=13.6 Hz, 2H), 7.38 (dd, J=8.0 Hz, 1.6 Hz, 1H), 7.50 (dd, J=10.4 Hz, 1.6 Hz, 1H), 7.66-7.63 (m, 1H), 8.24 (d, J=2.0 Hz, 1H), 8.64 (d, J=2.0 Hz, 1H), 9.61 (s, 1H). LCMS (mobile phase: 5-95% Acetonitrile-Water-0.1% TFA): purity is >95%. [M+H] Calc'd for C$_{22}$H$_{20}$N$_7$FS, 434; Found, 434.

Preparation 26A: 4-Bromo-N-(4-cyclopropylphenyl)-3-fluorobenzenecarboximidamide

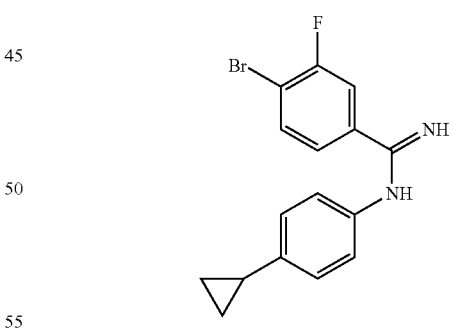

To EtMgBr (20 mL, 1M in THF) in THF (20 mL), under nitrogen, was carefully added 4-cyclopropylaniline (1.3 g, 10 mmol). After 30 minutes of stirring at rt, 4-bromo-3-fluorobenzonitrile (2 g, 10 mmol) in THF (5 mL) was added dropwise. The mixture was stirred at rt for 20 h, at which time ice-water (10 mL) was carefully added while maintaining vigorous stirring. The reaction mixture was separated between water and EtOAc. Organic extract was dried and concentrated to an orange suspension which was triturated with EtOAc and hexane, solid filtered, dried and concentrated to give the product as light yellow solid (1.37 g, 41%). ¹H NMR (400 MHz, DMSO-d₆): δ 0.61 (2H, d, J=3.8 Hz), 0.90 (2H, d, J=6.6 Hz), 1.88 (1H, m), 6.44 (2H, br s), 6.74 (2H, d, J=6.4 Hz), 7.02 (2H, d, J=8.1 Hz), 7.77 (2H, s), 7.89 (1H, d, J=10.6 Hz). [M+H] Calc'd for $C_{16}H_{14}BrFN_2$, 334; Found, 334.

Preparation 26B: 2-(4-Bromo-3-fluorophenyl)-3-(4-cyclopropylphenyl)-6-hydroxypyrimidin-4-one

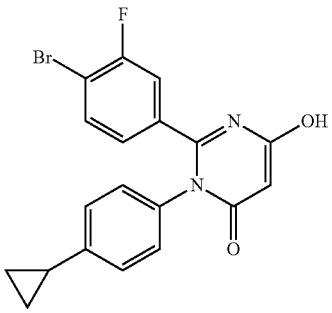 [SMILES: O=c1cc(O)nc(-c2ccc(Br)c(F)c2)n1-c1ccc(C2CC2)cc1]

A solution of 4-bromo-N-(4-cyclopropylphenyl)-3-fluorobenzenecarboximidamide (1.1 g, 3.3 mmol) and bis(2,4,6-trichlorophenyl)malonate (1.5 g, 3.3 mmol) in toluene (10 ml) was heated in a microwave oven at 160° C. for 1 h. The reaction mixture was then concentrated and purified by ISCO flash column (MeOH/CH₂Cl₂) to give 500 mg of the product (35%) as light yellow solid. ¹H NMR (400 MHz, DMSO-d₆): δ 0.62 (2H, d, J=4.7 Hz), 0.93 (2H, d, J=6.5 Hz), 1.87 (1H, m), 5.50 (1H, s), 7.00 (2H, d, J=8.3 Hz), 7.12 (3H, d&s, J=8.1 Hz), 7.38 (1H, d, J=9.8 Hz), 7.60 (1H, t, J=7.8 Hz). [M+H] Calc'd for $C_{19}H_{14}BrFN_2O_2$, 402; Found, 402.

Preparation 26C: 2-(4-Bromo-3-fluorophenyl)-6-chloro-3-(4-cyclopropylphenyl)pyrimidin-4-one

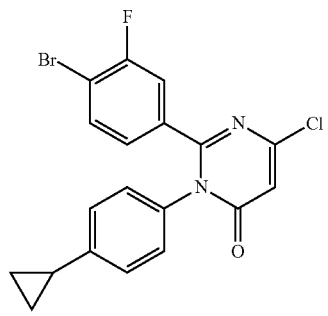 [SMILES: O=c1cc(Cl)nc(-c2ccc(Br)c(F)c2)n1-c1ccc(C2CC2)cc1]

A suspension of 2-(4-bromo-3-fluorophenyl)-3-(4-cyclopropylphenyl)-6-hydroxypyrimidin-4-one (960 mg, 2.4 mmol) in phosphorus oxychloride (10 mL) was heated at 100° C. for 4 h. The mixture was cooled to rt, concentrated, quenched with water (100 mL) and extracted with EtOAc. The organic layers were combined, washed with brine, dried (Na₂SO₄) and concentrated in vacuo. The residue was purified by ISCO flash column (EtOAc/Hexane) to afford 700 mg (70%) of the desired product. [M+H] Calc'd for $C_{19}H_{13}BrClFN_2O$, 420; Found, 420.

Preparation 26D: tert-butyl N-[1-[2-(4-bromo-3-fluorophenyl)-1-(4-cyclopropylphenyl)-6-oxopyrimidin-4-yl]piperidin-4-yl]carbamate

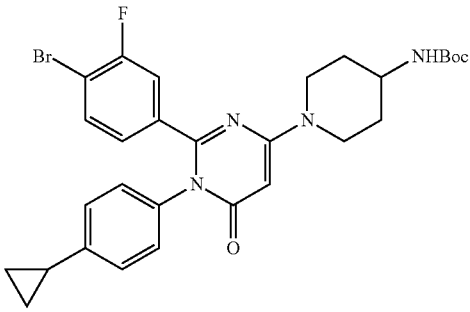 [SMILES: CC(C)(C)OC(=O)NC1CCN(c2cc(=O)n(-c3ccc(C4CC4)cc3)c(-c3ccc(Br)c(F)c3)n2)CC1]

A mixture of 2-(4-bromo-3-fluorophenyl)-6-chloro-3-(4-cyclopropylphenyl)pyrimidin-4-one (200 mg, 0.5 mmol), 4-boc-aminopiperidine (100 mg, 0.5 mmol) and DIEA (154 μL, 1.0 mmol) in DMF was heated at 90° C. for 1 h. The reaction mixture was concentrated and purified by ISCO flash column (EtOAc/Hexane) to give the product which was used for next step. [M+H] Calc'd for $C_{29}H_{32}BrFN_4O_3$, 584; Found, 584.

Example 26: 4-[4-(4-Aminopiperidin-1-yl)-1-(4-cyclopropylphenyl)-6-oxopyrimidin-2-yl]-2-fluorobenzonitrile

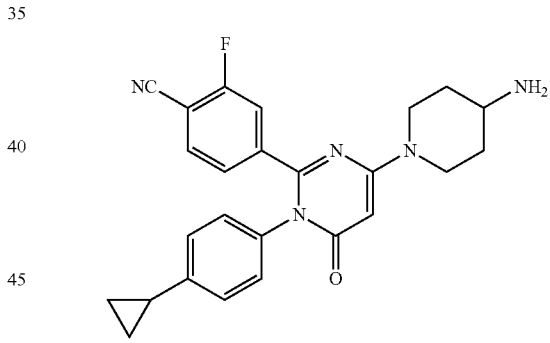

In a microwave vessel was added tert-butyl N-[1-[2-(4-bromo-3-fluorophenyl)-1-(4-cyclopropylphenyl)-6-oxopyrimidin-4-yl]piperidin-4-yl]carbamate (80 mg, 0.14 mmol), zinc cyanide (82 mg, 0.7 mmol) and Pd(PPh₃)₄ (12 mg, 0.01 mmol) in 3 mL DMF. The reaction mixture was heated at 120° C. for 1 h in a microwave oven. It was then purified by ISCO flash column (EtOAc/Hexane). The fractions were concentrated to a residue, which was dissolved in CH₂Cl₂ (5 mL) and treated with TFA (2 mL). After 2 h, the reaction mixture was concentrated and purified by prep-HPLC to afford the title compound as the formic acid salt (35 mg, 58%) as a light yellow solid. ¹H NMR (400 MHz, DMSO-d₆): δ 0.61 (2H, m), 0.92 (2H, m), 1.33 (2H, m), 1.81-1.89 (3H, m), 2.96 (2H, t, J=12.7 Hz), 3.18 (1H, m), 4.23 (2H, m), 5.57 (1H, s), 6.98 (2H, d, J=8.4 Hz), 7.07 (2H, d, J=8.4 Hz), 7.33 (1H, dd, J=8.0 and 1.2 Hz), 7.56 (1H, d, J=10.1 Hz), 7.82 (1H, t, J=7.8 Hz), 8.33 (1H, br s). [M+H] Calc'd for $C_{25}H_{24}FN_5O$, 430; Found, 430.

Example 27: 4-[4-(1,2,3,3a,4,6,7,7a-octahydropyr-rolo[3,2-c]pyridin-5-yl)-1-(4-cyclopropylphenyl)-6-oxopyrimidin-2-yl]-2-fluorobenzonitrile

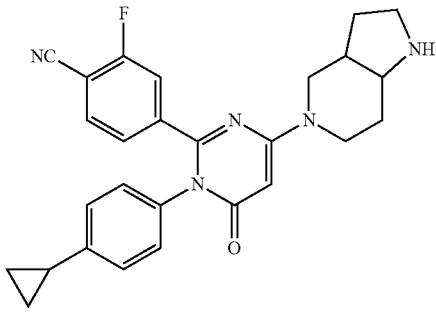 [SMILES: N#Cc1ccc(-c2nc(N3CCC4NCCC4C3)cc(=O)n2-c2ccc(C3CC3)cc2)cc1F]

The title compound was prepared as the TFA salt in 37% overall yield according to the general procedure for the preparation of Example 26 starting from 2-(4-bromo-3-fluorophenyl)-6-chloro-3-(4-cyclopropylphenyl)pyrimidin-4-one. $^1$H NMR (400 MHz, DMSO-$d_6$): δ 0.61 (2H, m), 0.93 (2H, m), 1.67-1.85 (3H, m), 2.02-2.32 (2H, m), 3.17 (1H, m), 3.29 (2H, m), 3.48 (2H, m), 3.65 (1H, m), 3.80 (2H, m), 5.52 (1H, s), 6.98 (2H, d, J=7.0 Hz), 7.07 (2H, m), 7.33 (1H, dd, J=8.0 and 1.2 Hz), 7.54 (1H, d, J=10.2 Hz), 7.83 (1H, t, J=7.7 Hz), 8.64 (1H, br s), 8.97 (1H, br s). [M+H] Calc'd for $C_{27}H_{26}FN_5O$, 456; Found, 456.

Example 28: 4-[4-(1,2,3,3a,4,6,7,7a-octahydropyr-rolo[3,4-c]pyridin-5-yl)-1-(4-cyclopropylphenyl)-6-oxopyrimidin-2-yl]-2-fluorobenzonitrile

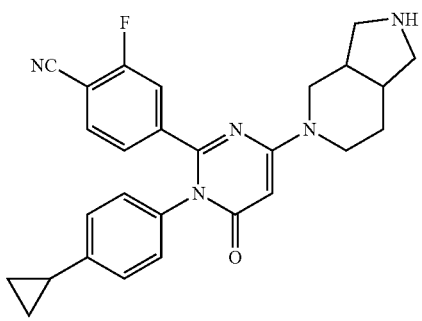 [SMILES: N#Cc1ccc(-c2nc(N3CCC4CNCC4C3)cc(=O)n2-c2ccc(C3CC3)cc2)cc1F]

The title compound was prepared as the TFA salt in 34% overall yield according to the general procedure for the preparation of Example 26 starting from 2-(4-bromo-3-fluorophenyl)-6-chloro-3-(4-cyclopropylphenyl)pyrimidin-4-one. $^1$H NMR (400 MHz, DMSO-$d_6$): δ 0.61 (2H, m), 0.93 (2H, m), 1.55 (1H, m), 1.77-1.88 (3H, m), 2.85 (1H, m), 3.07 (1H, m), 3.30 (2H, m), 3.45 (2H, m), 3.80 (2H, m), 5.53 (1H, s), 6.99 (2H, m), 7.09 (2H, m), 7.33 (1H, d, J=7.3 Hz), 7.55 (1H, d, J=10.1 Hz), 7.83 (1H, t, J=7.7 Hz), 8.73 (2H, br s). [M+H] Calc'd for $C_{27}H_{26}FN_5O$, 456; Found, 456.

Example 29: 4-[1-(4-cyclopropylphenyl)-4-(2,8-diazaspiro[4.5]decan-8-yl)-6-oxopyrimidin-2-yl]-2-fluorobenzonitrile

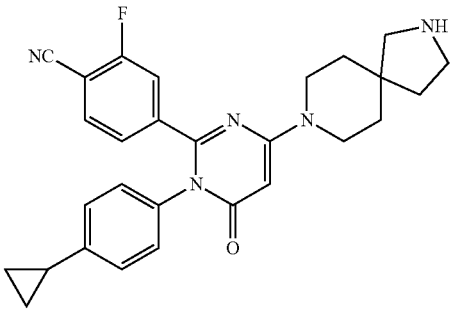 [SMILES: N#Cc1ccc(-c2nc(N3CCC4(CCNC4)CC3)cc(=O)n2-c2ccc(C3CC3)cc2)cc1F]

The title compound was prepared as the TFA salt in 49% overall yield according to the general procedure for the preparation of Example 26 starting from 2-(4-bromo-3-fluorophenyl)-6-chloro-3-(4-cyclopropylphenyl)pyrimidin-4-one. $^1$H NMR (400 MHz, DMSO-$d_6$): δ 0.62 (2H, m), 0.93 (2H, m), 1.58 (4H, m), 1.86 (3H, m), 3.06 (2H, t, J=5.5 Hz), 3.27 (2H, m), 3.57 (5H, m), 5.59 (1H, s), 6.98 (2H, d, J=8.4 Hz), 7.07 (2H, d, J=8.4 Hz), 7.33 (1H, d, J=8.0 Hz), 7.55 (1H, d, J=10.1 Hz), 7.83 (1H, t, J=7.6 Hz), 8.83 (2H, br s). [M+H] Calc'd for $C_{28}H_{28}FN_5O$, 470; Found, 470.

Example 30: 4-[4-(4-aminopiperidin-1-yl)-1-(3-fluoro-4-methoxyphenyl)-6-oxopyrimidin-2-yl]-2-fluorobenzonitrile

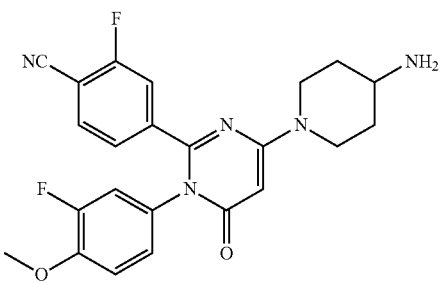 [SMILES: COc1ccc(-n2c(-c3ccc(C#N)c(F)c3)nc(N3CCC(N)CC3)cc2=O)cc1F]

The title compound was prepared as the formic acid salt in 4% overall yield according to the general procedure for the preparation of Example 26. $^1$H NMR (400 MHz, DMSO-$d_6$): δ 1.39 (2H, m), 1.92 (2H, d, J=11.1 Hz), 2.97 (2H, t, J=11.7 Hz), 3.21 (1H, m), 3.79 (3H, s), 4.27 (2H, m), 5.59 (1H, s), 6.97 (1H, dd, J=8.8 and 1.9 Hz), 7.05 (1H, t, J=8.9 Hz), 7.30 (1H, dd, J=11.9 and 2.2 Hz), 7.39 (1H, d, J=8.1 Hz), 7.61 (1H, d, J=10.0 Hz), 7.86 (1H, t, J=7.5 Hz), 8.33 (1H, br s). [M+H] Calc'd for $C_{23}H_{21}F_2N_5O_2$, 438; Found, 438.

Example 31: 4-[4-(4-aminopiperidin-1-yl)-1-(2-methylindazol-5-yl)-6-oxopyrimidin-2-yl]-2-fluorobenzonitrile

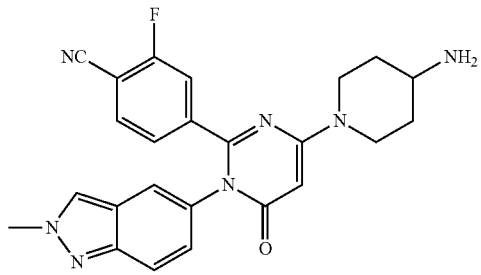 [SMILES: Cn1cc2cc(-n3c(-c4ccc(C#N)c(F)c4)nc(N4CCC(N)CC4)cc3=O)ccc2n1]

The title compound was prepared as the formic acid salt in 2% overall yield according to the general procedure for the preparation of Example 26. $^1$H NMR (400 MHz, DMSO-d$_6$): δ 1.38 (2H, m), 1.89 (2H, d, J=11.6 Hz), 2.98 (2H, t, J=12.7 Hz), 3.17 (1H, m), 4.11 (3H, s), 4.27 (2H, m), 5.60 (1H, s), 7.10 (1H, dd, J=9.1 and 1.6 Hz), 7.37 (1H, d, J=9.1 Hz), 7.50 (1H, s), 7.51 (1H, d, J=8.8 Hz), 7.61 (1H, d, J=10.4 Hz), 7.77 (1H, t, J=7.3 Hz), 8.28 (1H, s), 8.33 (1H, s). [M+H] Calc'd for C$_{24}$H$_{22}$FN$_7$O, 444; Found, 444.

Example 32: 4-[4-(4-aminopiperidin-1-yl)-1-(4-methoxyphenyl)-6-oxopyrimidin-2-yl]-2-fluorobenzonitrile

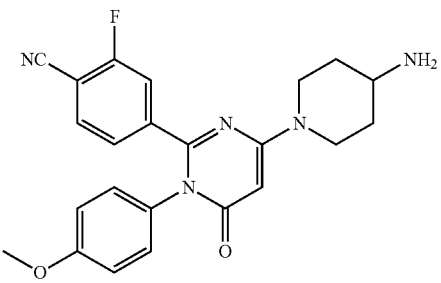 [SMILES: COc1ccc(-n2c(-c3ccc(C#N)c(F)c3)nc(N3CCC(N)CC3)cc2=O)cc1]

The title compound was prepared as the formic acid salt in 12% overall yield according to the general procedure for the preparation of Example 26. $^1$H NMR (400 MHz, DMSO-d$_6$): δ 1.39 (2H, m), 1.90 (2H, d, J=12.0 Hz), 2.96 (2H, t, J=12.5 Hz), 3.16 (1H, m), 3.70 (3H, s), 4.25 (2H, m), 5.57 (1H, s), 6.83 (2H, d, J=8.9 Hz), 7.13 (2H, d, J=8.8 Hz), 7.36 (1H, dd, J=8.0 and 1.2 Hz), 7.57 (1H, d, J=10.1 Hz), 7.83 (1H, t, J=7.8 Hz), 8.34 (1H, s). [M+H] Calc'd for C$_{23}$H$_{22}$FN$_5$O$_2$, 420; Found, 420.

Example 33: 4-[4-(4-aminopiperidin-1-yl)-1-(4-cyclopropyl-3-fluorophenyl)-6-oxopyrimidin-2-yl]-2-fluorobenzonitrile

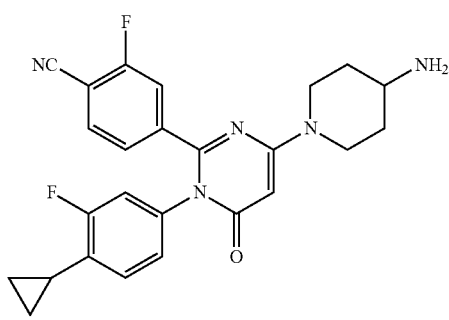 [SMILES: N#Cc1ccc(-c2nc(N3CCC(N)CC3)cc(=O)n2-c2ccc(C3CC3)c(F)c2)cc1F]

The title compound was prepared as the formic acid salt in 5% overall yield according to the general procedure for the preparation of Example 26. $^1$H NMR (400 MHz, DMSO-d$_6$): δ 0.67 (2H, m), 0.95 (3H, m), 1.16 ((1H, m), 1.46 (2H, m), 1.97 (3H, m), 2.92 (2H, m), 3.31 (1H, m), 4.30 (2H, m), 5.60 (1H, s), 6.93 (2H, m), 7.19 (1H, m), 7.38 (1H, m), 7.62 (1H, m), 7.85 (1H, m), 8.04 (2H, s). [M+H] Calc'd for C$_{25}$H$_{23}$F$_2$N$_5$O, 448; Found, 448.

Example 34: 4-[2-(4-aminopiperidin-1-yl)-5-{2-methyl-2H-indazol-5-yl)pyrazin-2-yl}-1,3-thiazol-4-yl]benzonitrile

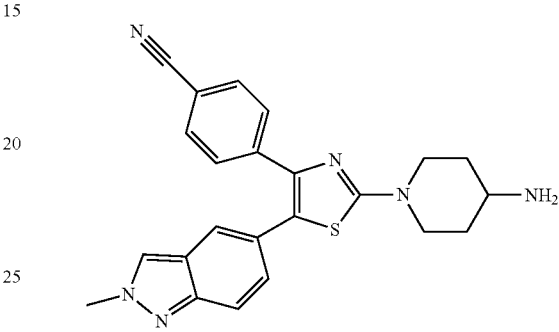

The title compound was prepared as the HCl salt in 56% overall yield according to the general procedure for the preparation of Example 1. $^1$H NMR (400 MHz, DMSO-d$_6$) δ ppm 1.52-1.80 (m, 2H), 1.92-2.11 (m, 2H), 3.03-3.25 (m, 2H), 3.25-3.40 (m, 1H), 3.90-4.05 (m, 2H), 4.17 (s, 3H), 5.21-5.89 (m, 7H), 6.95-7.17 (m, 1H), 7.52-7.65 (m, 3H), 7.65-7.76 (m, 3H), and 8.13 (br. s., 3H) 8.34 (s, 1H). LCMS (mobile phase: 5-95% Acetonitrile-Water-0.1% TFA): purity is >95%. [M+H] Calc'd for C$_{23}$H$_{22}$N$_6$S, 415; Found, 415.

II. Biological Evaluation

Example 1: In Vitro Enzyme Inhibition Assay—LSD-1

This assay determines the ability of a test compound to inhibit LSD1 demethylase activity. *E. coli* expressed full-length human LSD1 (Accession number 060341) was purchased from Active Motif (Cat#31334).

The enzymatic assay of LSD1 activity is based on Time Resolved-Fluorescence Resonance Energy Transfer (TR-FRET) detection. The inhibitory properties of compounds to LSD1 were determined in 384-well plate format under the following reaction conditions: 0.1-0.5 nM LSD1, 50 nM H3K4me1-biotin labeled peptide (Anaspec cat #64355), 2 μM FAD in assay buffer of 50 mM HEPES, pH7.3, 10 mM NaCl, 0.005% Brij35, 0.5 mM TCEP, 0.2 mg/ml BSA. Reaction product was determined quantitatively by TR-FRET after the addition of detection reagent Phycolink Streptavidin-allophycocyanin (Prozyme) and Europium-anti-unmodified histone H3 lysine 4 (H3K4) antibody (PerkinElmer) in the presence of LSD1 inhibitor such as 1.8 mM of Tranylcypromine hydrochloride (2-PCPA) in LANCE detection buffer (PerkinElmer) to final concentration of 12.5 nM and 0.25 nM respectively.

The assay reaction was performed according to the following procedure: 2 μL of the mixture of 150 nM H3K4me1-biotin labeled peptide with 2 μL of 11-point serial diluted test compound in 3% DMSO were added to each well of plate, followed by the addition of 2 μL of 0.3 nM LSD1 and 6 μM of FAD to initiate the reaction. The reaction mixture was then incubated at room temperature for one hour, and terminated by the addition of 6 μL of 1.8 mM 2-PCPA in LANCE detection buffer containing 25 nM Phycolink Streptavidin-allophycocyanin and 0.5 nM Europium-anti-unmodified H3K4 antibody. Enzymatic reaction is terminated within 15 minutes if 0.5 LSD1 enzyme is used in the plate. Plates were read by EnVision Multilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit LSD1 activity was quantified and the respective $IC_{50}$ value was determined. Table 3 provides the $IC_{50}$ values of various substituted heterocyclic compounds disclosed herein.

TABLE 3

| Chemical Synthesis Example | Name | LSD1 $IC_{50}$ (μM) |
|---|---|---|
| 1 | 4-[2-(4-aminopiperidin-1-yl)-5-(1-methyl-1H-indazol-5-yl)-1,3-thiazol-4-yl]benzonitrile | A |
| 2 | cis-4-(2-{decahydropyrrolo[3,4-d]azepin-6-yl}-5-(1-methyl-1H-indazol-5-yl)-1,3-thiazol-4-yl)benzonitrile | A |
| 3 | 4-[2-(4-aminopiperidin-1-yl)-5-{1-methyl-1H-pyrrolo[2,3-b]pyridin-5-yl}-1,3-thiazol-4-yl]benzonitrile | A |
| 4 | 4-[2-(4-aminopiperidin-1-yl)-5-{1-methyl-1H-pyrazolo[3,4-b]pyridin-5-yl}-1,3-thiazol-4-yl]benzonitrile | A |
| 5 | 4-(2-{2,8-diazaspiro[4.5]decan-8-yl}-5-(1-methyl-1H-indazol-5-yl)-1,3-thiazol-4-yl)benzonitrile | A |
| 6 | 4-[5-(1-methyl-1H-indazol-5-yl)-2-{octahydro-1H-pyrrolo[3,2-c]pyridin-5-yl}-1,3-thiazol-4-yl]benzonitrile | A |
| 7 | 4-[5-(1-methyl-1H-indazol-5-yl)-2-{octahydro-1H-pyrrolo[3,4-c]pyridin-5-yl}-1,3-thiazol-4-yl]benzonitrile | A |
| 8 | 4-[2-(4-aminopiperidin-1-yl)-5-(1-methyl-1H-1,3-benzodiazol-5-yl)-1,3-thiazol-4-yl]benzonitrile | A |
| 9 | 4-[2-(4-aminopiperidin-1-yl)-5-{3-methyl-3H-imidazo[4,5-b]pyridin-6-yl}-1,3-thiazol-4-yl]benzonitrile | A |
| 10 | cis-4-(2-{decahydropyrrolo[3,4-d]azepin-6-yl}-5-(1-methyl-1H-1,3-benzodiazol-5-yl)-1,3-thiazol-4-yl)benzonitrile | A |
| 11 | cis-4-(2-{decahydropyrrolo[3,4-d]azepin-6-yl}-5-{1-methyl-1H-pyrazolo[3,4-b]pyridin-5-yl}-1,3-thiazol-4-yl)benzonitrile | A |
| 12 | 4-[2-(4-aminopiperidin-1-yl)-5-[1-(2,2,2-trifluoroethyl)-1H-pyrazol-4-yl]-1,3-thiazol-4-yl]benzonitrile | A |
| 13 | 4-(2-{decahydropyrrolo[3,4-d]azepin-6-yl}-5-[1-(2,2,2-trifluoroethyl)-1H-pyrazol-4-yl]-1,3-thiazol-4-yl)benzonitrile | A |
| 14 | 4-{5-[1-(cyclopropylmethyl)-1H-pyrazol-4-yl]-2-{decahydropyrrolo[3,4-d]azepin-6-yl}-1,3-thiazol-4-yl}benzonitrile | A |
| 15 | 4-{5-[1-(cyclopropylmethyl)-1H-pyrazol-4-yl]-2-{decahydropyrrolo[3,4-d]azepin-6-yl}-1,3-thiazol-4-yl}benzonitrile | A |
| 16 | 4-{2-[(3R)-3-aminopiperidine-1-carbonyl]-5-(1-methyl-1H-1,3-benzodiazol-5-yl)-1,3-thiazol-4-yl}benzonitrile | A |
| 17 | 4-{2-[(3S)-3-aminopiperidine-1-carbonyl]-5-(1-methyl-1H-1,3-benzodiazol-5-yl)-1,3-thiazol-4-yl}benzonitrile | A |
| 18 | 4-[2-(4-aminopiperidine-1-carbonyl)-5-(1-methyl-1H-1,3-benzodiazol-5-yl)-1,3-thiazol-4-yl]benzonitrile | A |
| 19 | 4-{2-[(3R)-3-aminopiperidine-1-carbonyl]-5-(4-methylphenyl)-1,3-thiazol-4-yl}benzonitrile | A |
| 20 | 4-{2-[(3R)-3-aminopiperidine-1-carbonyl]-5-{3-methyl-3H-imidazo[4,5-b]pyridin-6-yl}-1,3-thiazol-4-yl}benzonitrile | A |
| 21 | 4-{2-[(3R)-3-aminopiperidine-1-carbonyl]-5-[1-(2,2,2-trifluoroethyl)-1H-pyrazol-4-yl]-1,3-thiazol-4-yl}benzonitrile | A |
| 22 | 4-{2-[(3R)-3-aminopiperidine-1-carbonyl]-5-[1-(cyclopropylmethyl)-1H-pyrazol-4-yl]-1,3-thiazol-4-yl}benzonitrile | A |
| 23 | 4-[2-(4-aminopiperidin-1-yl)-5-(3-hydroxy-3-methylbut-1-yn-1-yl)-1,3-thiazol-4-yl]benzonitrile | — |
| 24 | 4-[2-(4-aminopiperidin-1-yl)-5-(3-hydroxy-3-methylbut-1-yn-1-yl)-1,3-thiazol-4-yl]benzonitrile | — |
| 25 | 4-[2-(4-aminopiperidin-1-yl)-5-{3-methyl-3H-imidazo[4,5-b]pyridin-6-yl}-1,3-thiazol-4-yl]-2-fluorobenzonitrile | — |
| 26 | 4-[4-(4-aminopiperidin-1-yl)-1-(4-cyclopropylphenyl)-6-oxopyrimidin-2-yl]-2-fluorobenzonitrile | A |
| 27 | 4-[4-(1,2,3,3a,4,6,7,7a-octahydropyrrolo[3,2-c]pyridin-5-yl)-1-(4-cyclopropylphenyl)-6-oxopyrimidin-2-yl]-2-fluorobenzonitrile | A |
| 28 | 4-[4-(1,2,3,3a,4,6,7,7a-octahydropyrrolo[3,4-c]pyridin-5-yl)-1-(4-cyclopropylphenyl)-6-oxopyrimidin-2-yl]-2-fluorobenzonitrile | A |
| 29 | 4-[1-(4-cyclopropylphenyl)-4-(2,8-diazaspiro[4.5]decan-8-yl)-6-oxopyrimidin-2-yl]-2-fluorobenzonitrile | A |
| 30 | 4-[4-(4-aminopiperidin-1-yl)-1-(3-fluoro-4-methoxyphenyl)-6-oxopyrimidin-2-yl]-2-fluorobenzonitrile | A |
| 31 | 4-[4-(4-aminopiperidin-1-yl)-1-(2-methylindazol-5-yl)-6-oxopyrimidin-2-yl]-2-fluorobenzonitrile | A |
| 32 | 4-[4-(4-aminopiperidin-1-yl)-1-(4-methoxyphenyl)-6-oxopyrimidin-2-yl]-2-fluorobenzonitrile | A |
| 33 | 4-[4-(4-aminopiperidin-1-yl)-1-(4-cyclopropyl-3-fluorophenyl)-6-oxopyrimidin-2-yl]-2-fluorobenzonitrile | A |
| 34 | 4-[2-(4-aminopiperidin-1-yl)-5-{2-methyl-2H-indazol-5-yl)pyrazin-2-yl}-1,3-thiazol-4-yl]benzonitrile | A |

Note:
Biochemical assay $IC_{50}$ data are designated within the following ranges:
A: ≤0.10 μM
B: >0.10 μM to ≤1.0 μM
C: >1.0 μM to ≤10 μM
D: >10 μM Example 2: In Vitro Enzyme Inhibition Assay—MAO Selectivity Human recombinant monoamine oxidase proteins MAO-A and MAO-B are obtained. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay is performed. 3-(2-Aminophenyl)-3-oxopropanamine (kynuramine dihydrobromide, Sigma Aldrich), a non-fluorescent compound is chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity is estimated by measuring the conversion of kynuramine into 4-hydroxyquinoline. Assays are conducted in 96-well black plates with clear bottom (Corning) in a final volume of 100 μl. The assay buffer is 100 mM HEPES, pH 7.5. Each experiment is performed in triplicate within the same experiment.

Briefly, a fixed amount of MAO (0.25 μg for MAO-A and 0.5 μg for AO-B) is incubated on ice for 15 minutes in the reaction buffer, in the absence and/or in the presence of various concentrations of compounds as disclosed herein (e.g., from 0 to 50 μM, depending on the inhibitor strength). Tranylcypromine (Biomol International) is used as a control for inhibition.

After leaving the enzyme(s) interacting with the test compound, 60 to 90 μM of kynuramine is added to each reaction for MAO-B and MAO-A assay respectively, and the reaction is left for 1 hour at 37° C. in the dark. The oxidative deamination of the substrate is stopped by adding 50 μl of 2N NaOH. The conversion of kynuramine to 4-hydroxyquinoline, is monitored by fluorescence (excitation at 320 nm, emission at 360 nm) using a microplate reader (Infinite 200, Tecan). Arbitrary units are used to measure levels of fluorescence produced in the absence and/or in the presence of test compound.

The maximum of oxidative deamination activity is obtained by measuring the amount of 4-hydroxyquinoline formed from kynuramine deamination in the absence of test compound and corrected for background fluorescence. The Ki ($IC_{50}$) of each inhibitor is determined at Vmax/2.

Example 3: LSD1 CD11b Cellular Assay

To analyze LSD1 inhibitor efficacy in cells, a CD11b flow cytometry assay was performed. LSD1 inhibition induces CD11b expression in THP-1 (AML) cells which can be measured by flow cytometry. THP-1 cells were seeded at 100,000 cells/well in 10% Fetal Bovine Serum containing RPMI 1640 media in a 24 well plate with a final volume of 500 μL per well. LSD1 test compounds were serially diluted in DMSO. The dilutions were added to each well accordingly to a final concentration of 0.2% DMSO. The cells were incubated at 37 degrees Celsius in 5% $CO_2$ for 4 days. 250 μL of each well was transferred to a well in a 96 well round bottom plate. The plate was centrifuged at 1200 rpm at 4 degrees Celsius in a Beckman Coulter Alegra 6KR centrifuge for 5 minutes. The media was removed leaving the cells at the bottom of the wells. The cells were washed in 100 μL cold HBSS (Hank's Balanced Salt Solution) plus 2% BSA (Bovine Serum Albumin) solution and centrifuged at 1200 rpm at 4 degrees Celsius for 5 minutes. The wash was removed. The cells were resuspended in 100 μL HBSS plus 2% BSA containing 1:15 dilution of APC conjugated mouse anti-CD11b antibody (BD Pharmingen Cat#555751) and incubated on ice for 25 minutes. The cells were centrifuged and washed two times in 100 μl HBSS plus 2% BSA. After the final spin the cells were resuspended in 100 μL HBSS plus 2% BSA containing 1 ug/mL DAPI (4',6-diamidino-2-phenylindole). The cells were then analyzed by flow cytometry in a BD FACSAria machine. Cells were analyzed for CD11b expression. The percent of CD11b expressing cells for each inhibitor concentration was used to determine an $IC_{50}$ curve for each compound analyzed.

Table 4 provides the cellular $IC_{50}$ values of various substituted heterocyclic compounds disclosed herein.

TABLE 4

| Chemical Synthesis Example | Name | Cellular $IC_{50}$ (μM) |
|---|---|---|
| 1 | 4-[2-(4-aminopiperidin-1-yl)-5-(1-methyl-1H-indazol-5-yl)-1,3-thiazol-4-yl]benzonitrile | A |
| 2 | cis-4-(2-{decahydropyrrolo[3,4-d]azepin-6-yl}-5-(1-methyl-1H-indazol-5-yl)-1,3-thiazol-4-yl)benzonitrile | A |
| 3 | 4-[2-(4-aminopiperidin-1-yl)-5-{1-methyl-1H-pyrrolo[2,3-b]pyridin-5-yl}-1,3-thiazol-4-yl]benzonitrile | A |
| 4 | 4-[2-(4-aminopiperidin-1-yl)-5-{1-methyl-1H-pyrazolo[3,4-b]pyridin-5-yl}-1,3-thiazol-4-yl]benzonitrile | A |
| 5 | 4-(2-{2,8-diazaspiro[4.5]decan-8-yl}-5-(1-methyl-1H-indazol-5-yl)-1,3-thiazol-4-yl)benzonitrile | B |
| 6 | 4-[5-(1-methyl-1H-indazol-5-yl)-2-{octahydro-1H-pyrrolo[3,2-c]pyridin-5-yl}-1,3-thiazol-4-yl]benzonitrile | A |
| 7 | 4-[5-(1-methyl-1H-indazol-5-yl)-2-{octahydro-1H-pyrrolo[3,4-c]pyridin-5-yl}-1,3-thiazol-4-yl]benzonitrile | A |
| 8 | 4-[2-(4-aminopiperidin-1-yl)-5-(1-methyl-1H-1,3-benzodiazol-5-yl)-1,3-thiazol-4-yl]benzonitrile | A |
| 9 | 4-[2-(4-aminopiperidin-1-yl)-5-{3-methyl-3H-imidazo[4,5-b]pyridin-6-yl}-1,3-thiazol-4-yl]benzonitrile | A |
| 10 | cis-4-(2-{decahydropyrrolo[3,4-d]azepin-6-yl}-5-(1-methyl-1H-1,3-benzodiazol-5-yl)-1,3-thiazol-4-yl)benzonitrile | A |
| 11 | cis-4-(2-{decahydropyrrolo[3,4-d]azepin-6-yl}-5-{1-methyl-1H-pyrazolo[3,4-b]pyridin-5-yl}-1,3-thiazol-4-yl)benzonitrile | A |
| 12 | 4-[2-(4-aminopiperidin-1-yl)-5-[1-(2,2,2-trifluoroethyl)-1H-pyrazol-4-yl]-1,3-thiazol-4-yl]benzonitrile | A |
| 13 | 4-(2-{decahydropyrrolo[3,4-d]azepin-6-yl}-5-[1-(2,2,2-trifluoroethyl)-1H-pyrazol-4-yl]-1,3-thiazol-4-yl)benzonitrile | A |
| 14 | 4-{5-[1-(cyclopropylmethyl)-1H-pyrazol-4-yl]-2-{decahydropyrrolo[3,4-d]azepin-6-yl}-1,3-thiazol-4-yl}benzonitrile | B |
| 15 | 4-{5-[1-(cyclopropylmethyl)-1H-pyrazol-4-yl]-2-{decahydropyrrolo[3,4-d]azepin-6-yl}-1,3-thiazol-4-yl}benzonitrile | B |
| 16 | 4-{2-[(3R)-3-aminopiperidine-1-carbonyl]-5-(1-methyl-1H-1,3-benzodiazol-5-yl)-1,3-thiazol-4-yl}benzonitrile | A |
| 17 | 4-{2-[(3S)-3-aminopiperidine-1-carbonyl]-5-(1-methyl-1H-1,3-benzodiazol-5-yl)-1,3-thiazol-4-yl}benzonitrile | A |
| 18 | 4-[2-(4-aminopiperidine-1-carbonyl)-5-(1-methyl-1H-1,3-benzodiazol-5-yl)-1,3-thiazol-4-yl]benzonitrile | A |
| 19 | 4-{2-[(3R)-3-aminopiperidine-1-carbonyl]-5-(4-methylphenyl)-1,3-thiazol-4-yl}benzonitrile | A |
| 20 | 4-{2-[(3R)-3-aminopiperidine-1-carbonyl]-5-{3-methyl-3H-imidazo[4,5-b]pyridin-6-yl}-1,3-thiazol-4-yl}benzonitrile | B |
| 21 | 4-{2-[(3R)-3-aminopiperidine-1-carbonyl]-5-[1-(2,2,2-trifluoroethyl)-1H-pyrazol-4-yl]-1,3-thiazol-4-yl}benzonitrile | A |
| 22 | 4-{2-[(3R)-3-aminopiperidine-1-carbonyl]-5-[1-(cyclopropylmethyl)-1H-pyrazol-4-yl]-1,3-thiazol-4-yl}benzonitrile | B |
| 23 | 4-[2-(4-aminopiperidin-1-yl)-5-(3-hydroxy-3-methylbut-1-yn-1-yl)-1,3-thiazol-4-yl]benzonitrile | — |
| 24 | 4-[2-(4-aminopiperidin-1-yl)-5-(3-hydroxy-3-methylbut-1-yn-1-yl)-1,3-thiazol-4-yl]benzonitrile | — |
| 25 | 4-[2-(4-aminopiperidin-1-yl)-5-{3-methyl-3H-imidazo[4,5-b]pyridin-6-yl}-1,3-thiazol-4-yl]-2-fluorobenzonitrile | — |
| 26 | 4-[4-(4-aminopiperidin-1-yl)-1-(4-cyclopropylphenyl)-6-oxopyrimidin-2-yl]-2-fluorobenzonitrile | A |
| 27 | 4-[4-(1,2,3,3a,4,6,7,7a-octahydropyrrolo[3,2-c]pyridin-5-yl)-1-(4-cyclopropylphenyl)-6-oxopyrimidin-2-yl]-2-fluorobenzonitrile | A |

TABLE 4-continued

| Chemical Synthesis Example | Name | Cellular IC$_{50}$ (µM) |
|---|---|---|
| 28 | 4-[4-(1,2,3,3a,4,6,7,7a-octahydropyrrolo[3,4-c]pyridin-5-yl)-1-(4-cyclopropylphenyl)-6-oxopyrimidin-2-yl]-2-fluorobenzonitrile | A |
| 29 | 4-[1-(4-cyclopropylphenyl)-4-(2,8-diazaspiro[4.5]decan-8-yl)-6-oxopyrimidin-2-yl]-2-fluorobenzonitrile | A |
| 30 | 4-[4-(4-aminopiperidin-1-yl)-1-(3-fluoro-4-methoxyphenyl)-6-oxopyrimidin-2-yl]-2-fluorobenzonitrile | B |
| 31 | 4-[4-(4-aminopiperidin-1-yl)-1-(2-methylindazol-5-yl)-6-oxopyrimidin-2-yl]-2-fluorobenzonitrile | B |
| 32 | 4-[4-(4-aminopiperidin-1-yl)-1-(4-methoxyphenyl)-6-oxopyrimidin-2-yl]-2-fluorobenzonitrile | — |
| 33 | 4-[4-(4-aminopiperidin-1-yl)-1-(4-cyclopropyl-3-fluorophenyl)-6-oxopyrimidin-2-yl]-2-fluorobenzonitrile | A |
| 34 | 4-[2-(4-aminopiperidin-1-yl)-5-{2-methyl-2H-indazol-5-yl)pyrazin-2-yl}-1,3-thiazol-4-yl]benzonitrile | A |

Note:
Cellular assay IC$_{50}$ data are designated within the following ranges:
A: ≤0.10 µM
B: >0.10 µM to ≤1.0 µM
C: >1.0 µM to ≤10 µM
D: >10 µM

Example 4: In Vivo Xenograph Study—MCF-7 Xenograph

Time release pellets containing 0.72 mg 17-13 Estradiol are subcutaneously implanted into nu/nu mice. MCF-7 cells are grown in RPMI containing 10% FBS at 5% CO$_2$, 37° C. Cells are spun down and re-suspended in 50% RPMI (serum free) and 50% Matrigel at 1×10$^7$ cells/mL. MCF-7 cells are subcutaneously injected (100 µL/animal) on the right flank 2-3 days post pellet implantation and tumor volume (length× width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

Example 5: In Vivo Xenograph Study—LNCaP Xenograph

LNCaP cells with a stable knockdown of LSD1 (shLSD1 cells) or control cells (such as shNTC cells) are inoculated in the dorsal flank of nude mice by subcutaneous injection (such as 3×10$^6$ cells in 100 µl of 50% RPMI 1640/BD Matrigel). Mouse weight and tumor size are measured once per week and tumor volume is estimated using the formula (7i/6)(L×W), where L=length of tumor and W=width of tumor. A two sample t-test is performed to determine statistical differences in mean tumor volume between the two groups.

Unmodified LNCaP cells are inoculated by subcutaneous injection into the dorsal flank of nude mice (such as 3×10$^6$ cells in 100 µl of 50% RPMI 1640/BD Matrigel). After three weeks, mice are injected intraperitoneally once per day with water (control), pargyline (0.53 mg or 1.59 mg; 1 or 3 mM final concentration, assuming 70% bioavailability), or XB154 (4 or 20 µg; 1 or 5 µM final concentration, assuming 70% bioavailability) or treated with a test compound (5 mg/kg each week or 10 mg/kg each week). Treatment continues for three weeks, during which time mouse weight and tumor volume are measured as above.

shLSD1 LNCaP cells or control cells are injected in nude mice as above. After three weeks, mice are treated with 2.6 µg mitomycin C (predicted final concentration of 1 µM assuming 40% bioavailability), olaparib (for example, about 0.5 mg/kg to 25 mg/kg), or vehicle intraperitoneally once per day for three weeks. In other examples, unmodified LNCaP cells are injected in nude mice as above.

After three weeks, mice are treated with test compounds, or vehicle as above, plus MMC or olaparib. Treatment continues for three weeks, during which time mouse weight and tumor volume are measured as above.

A decrease in tumor volume compared to control in mice injected with shLSD1 cells indicates that LSD1 inhibition decreases tumor growth in vivo.

Similarly, a decrease in tumor volume compared to control in mice injected with LNCaP cells and treated with a compound disclosed herein indicates that LSD1 inhibition decreases tumor growth in vivo. Finally, a decrease in tumor volume in mice injected with LNCaP cells and treated with a compound disclosed herein plus olaparib as compared to mice treated with a compound disclosed herein alone indicates that inhibition of LSD1 plus inhibition of PARP decreases tumor growth in vivo.

The harvested xenograft tissue is examined for evidence of LSD1 inhibition. This is assessed with Western blots to examine global levels of the 2MK4 and 2MK9 histone marks, expression of FA/BRcA genes, FANCD2 ubiquitination, and LSD1 protein levels in the cases of the shRNA cells. A decrease in one or more of these parameters indicates the effective inhibition of LSD 1. Additionally, effects on DNA damage repair are assessed with staining for H$_2$AX foci.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:
1. A compound, or a pharmaceutically acceptable salt thereof, selected from the group consisting of:

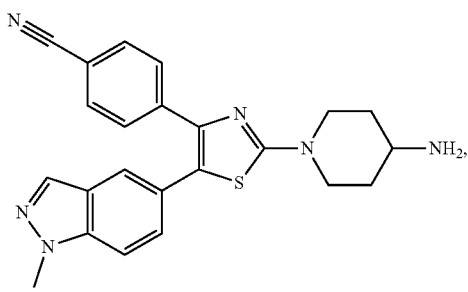

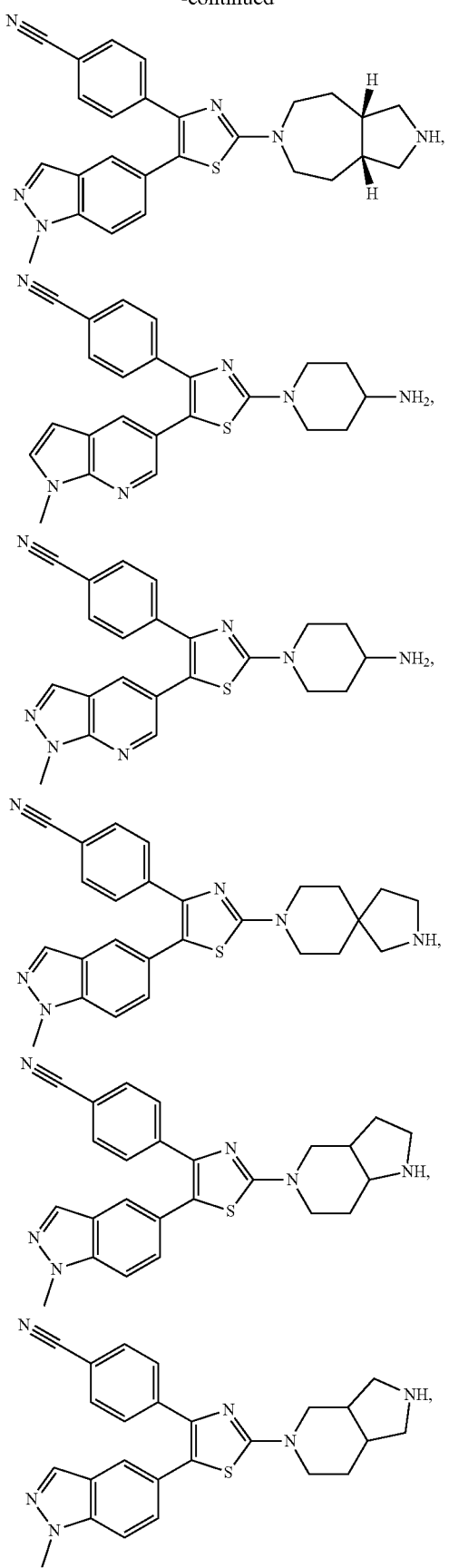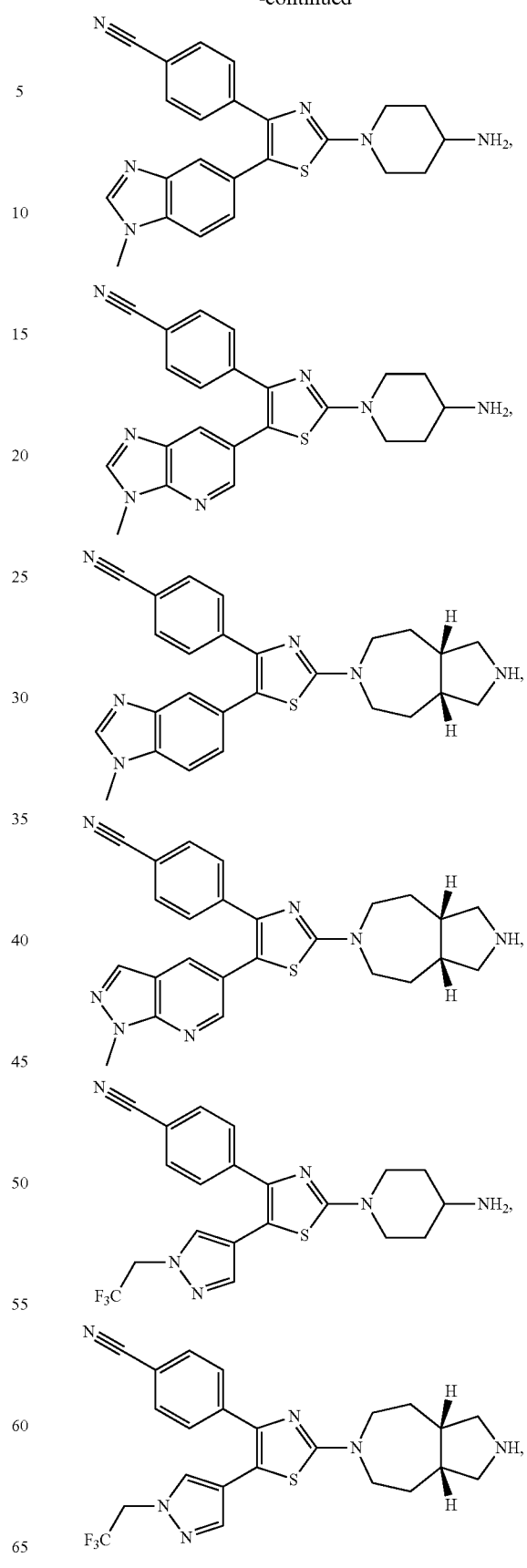

99
-continued
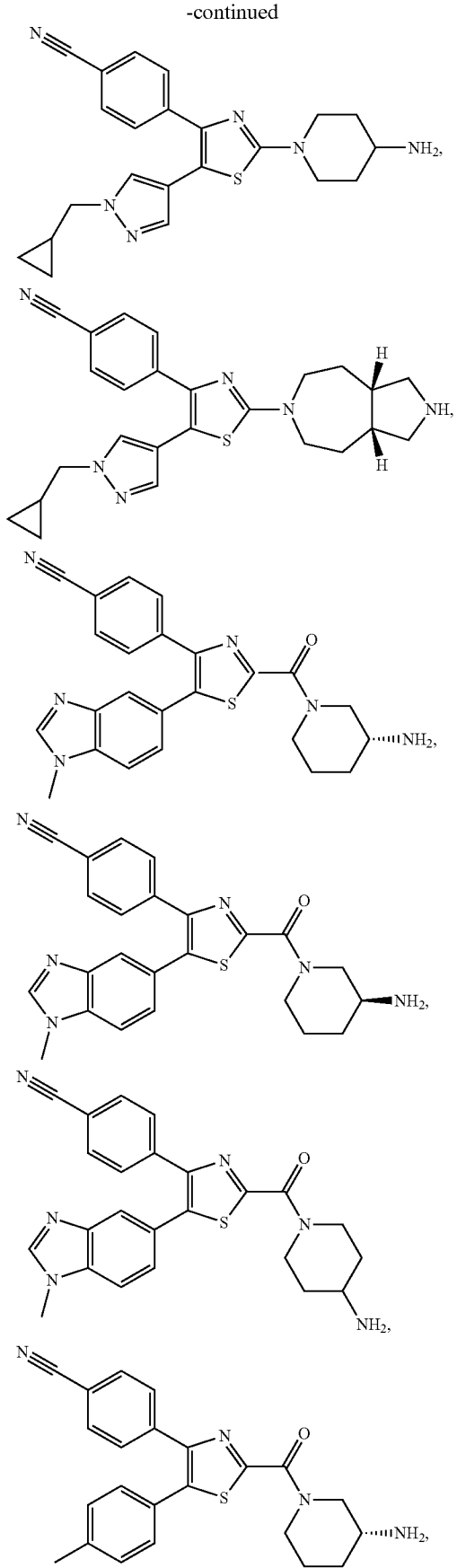
100
-continued
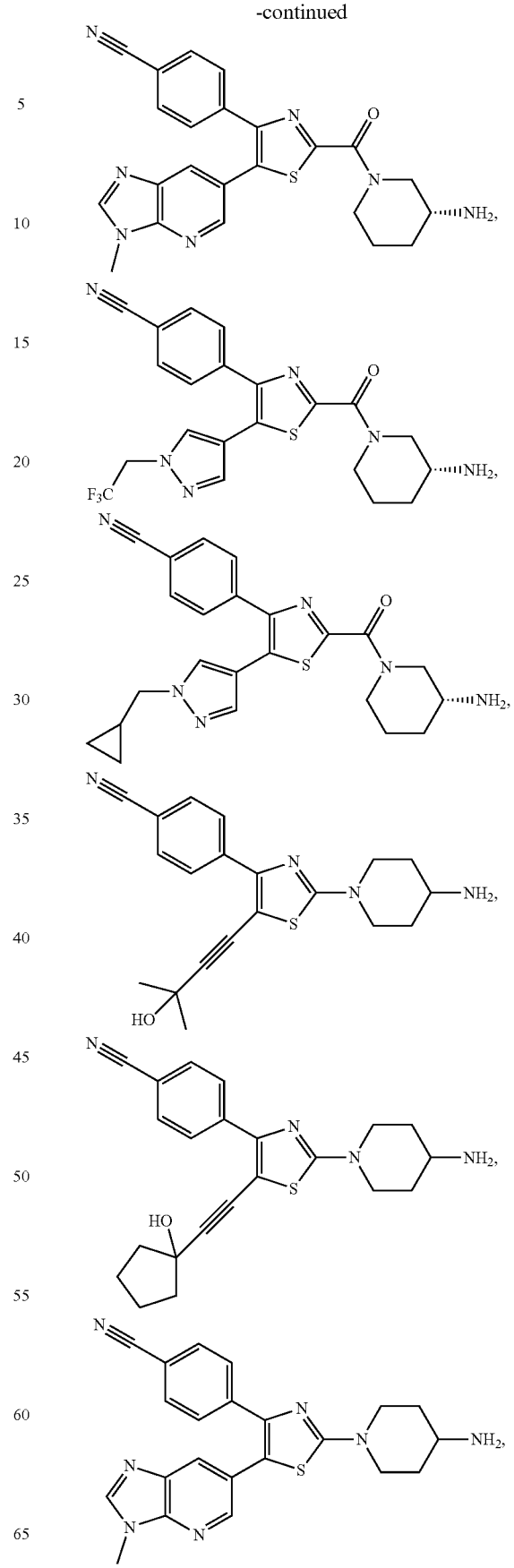

-continued

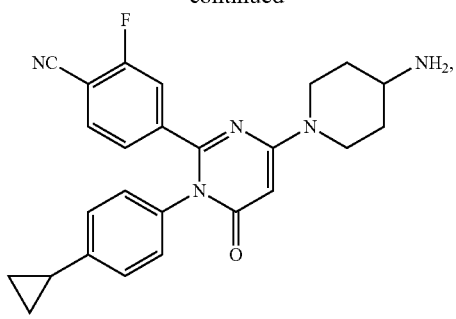
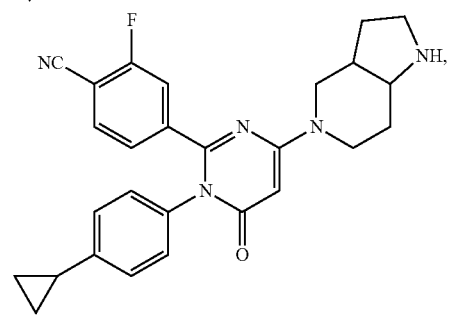
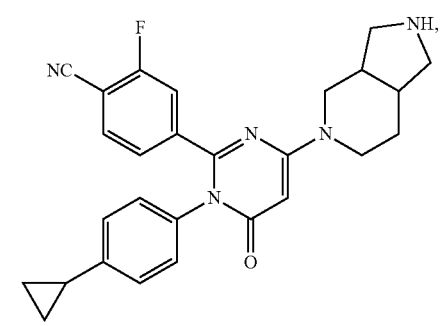
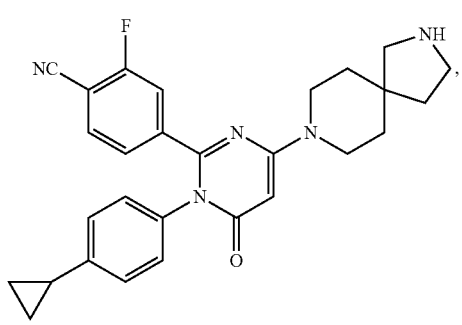
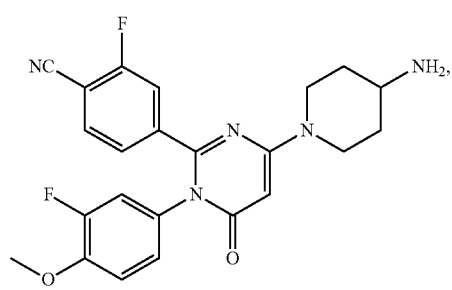

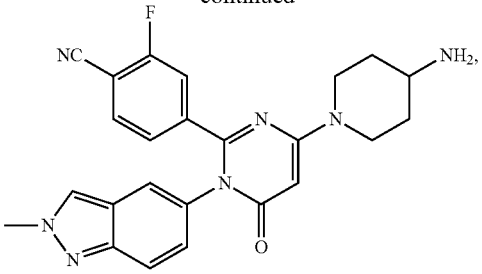
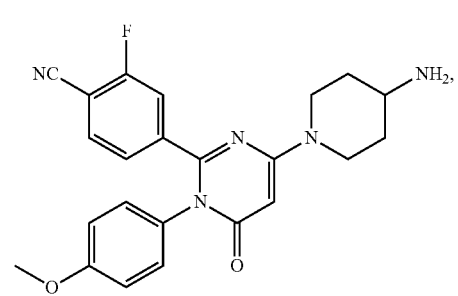
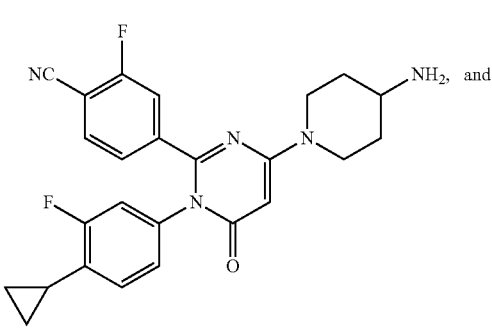
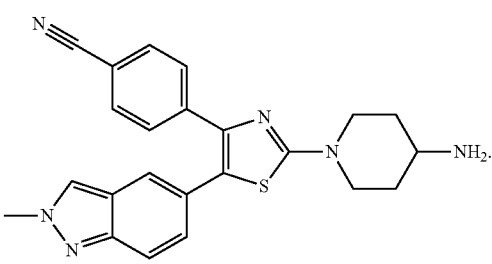

2. A pharmaceutical composition comprising the compound of claim 1 or a pharmaceutical acceptable salt thereof and a pharmaceutical acceptable carrier.

3. A method for therapeutically treating acute myeloid leukemia, breast or prostate cancer in a patient in need thereof, comprising administering to the patient the pharmaceutical composition of claim 2.

4. A method of modulating gene transcription in a cell comprising inhibiting lysine-specific demethylase 1 activity by contacting the lysine-specific demethylase 1 enzyme with the compound of claim 1.

5. A compound, or a pharmaceutically acceptable salt thereof, selected from the group consisting of:

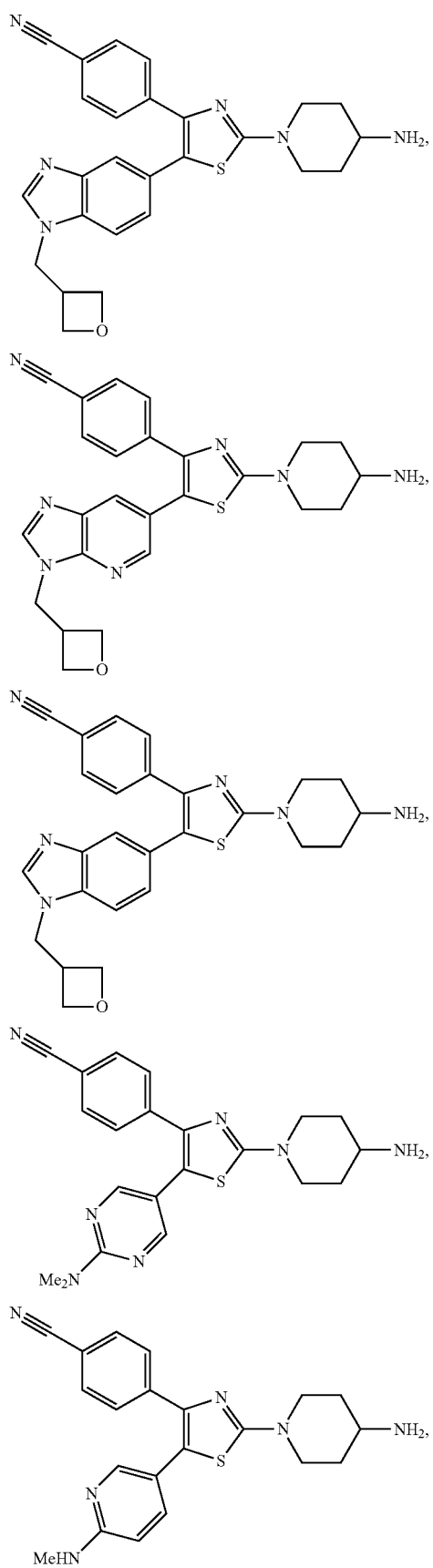
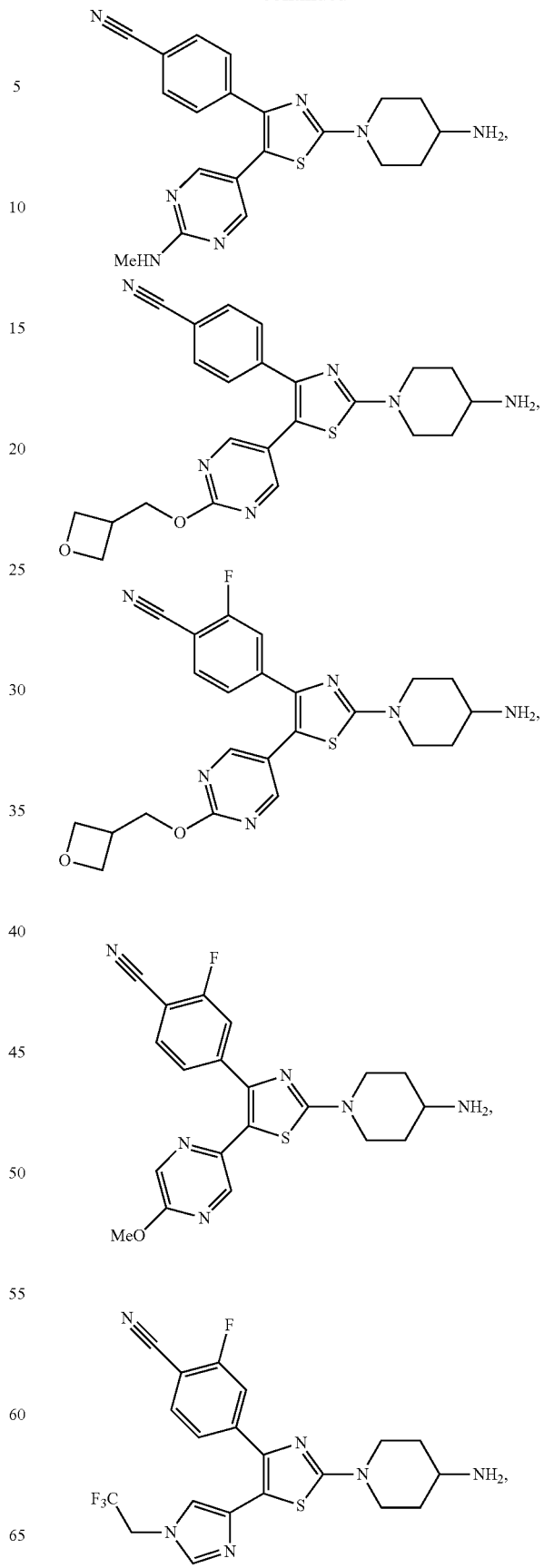

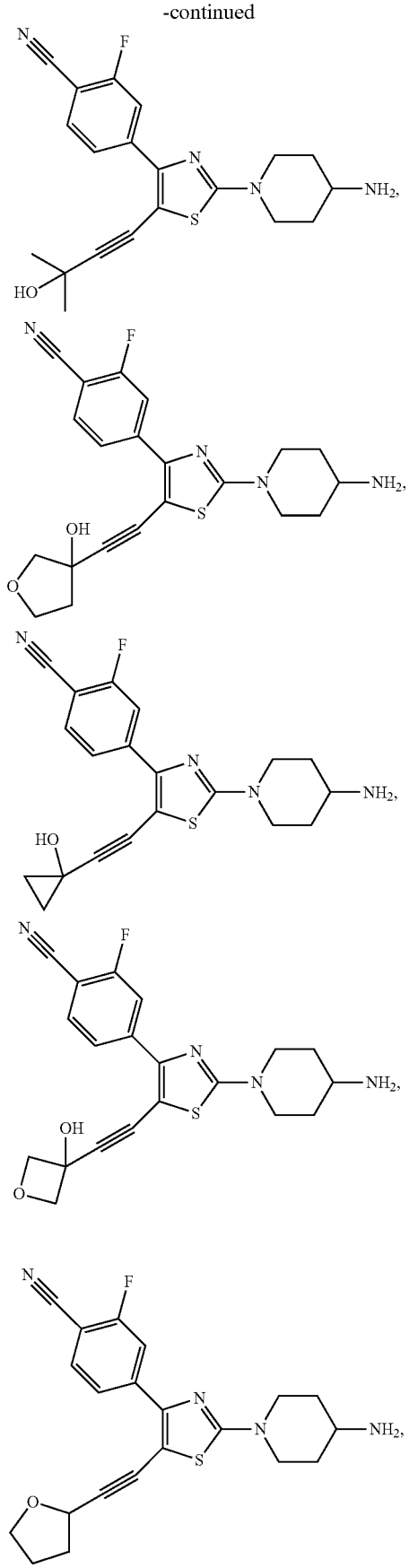
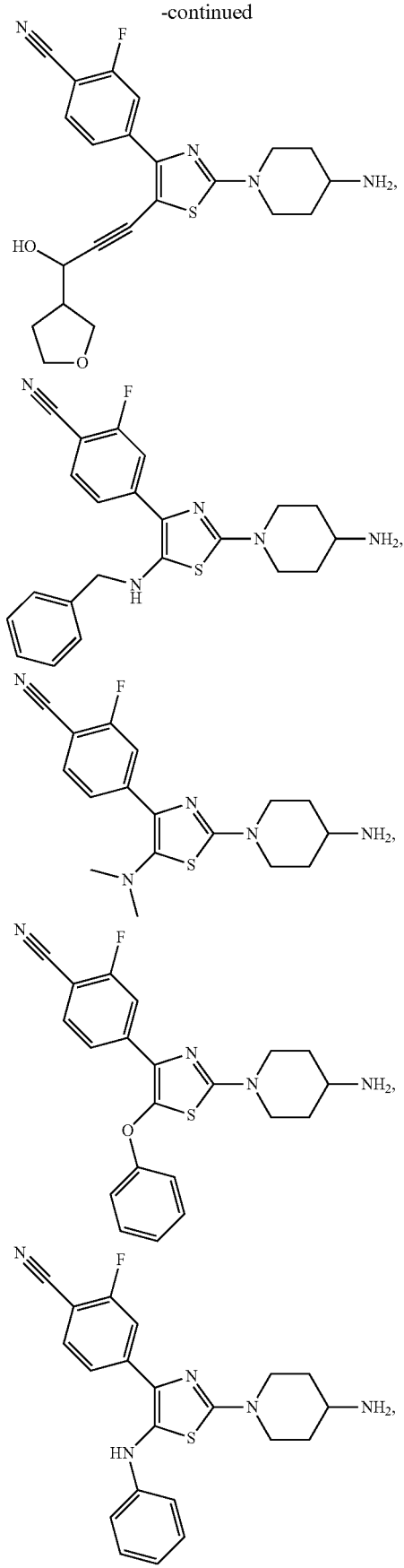

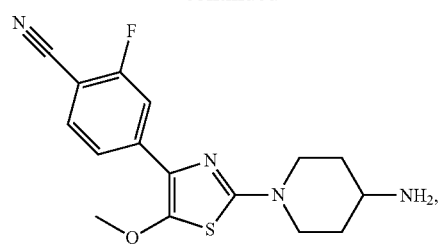
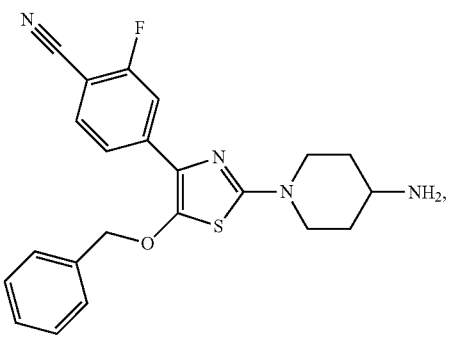
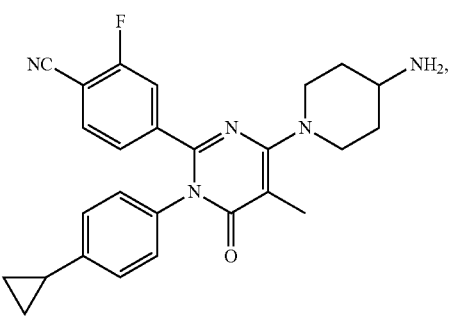
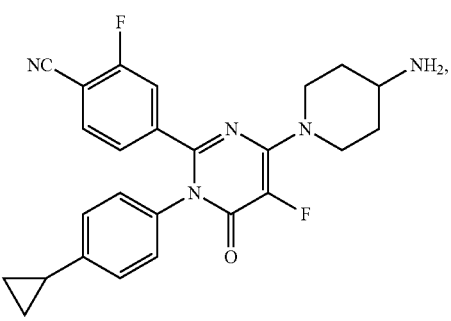
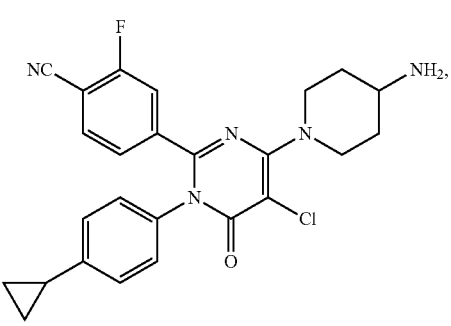
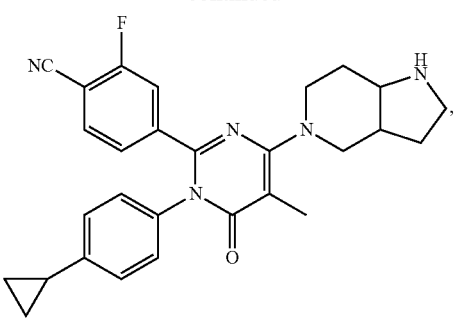
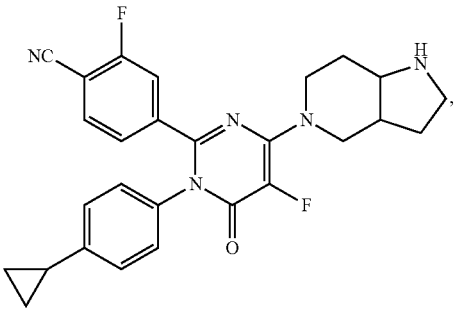
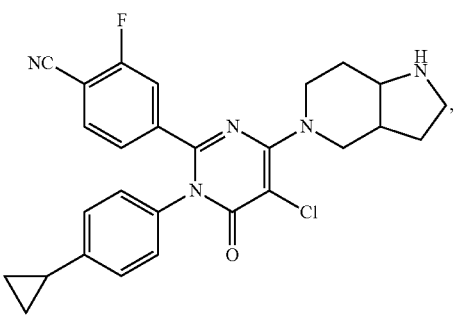
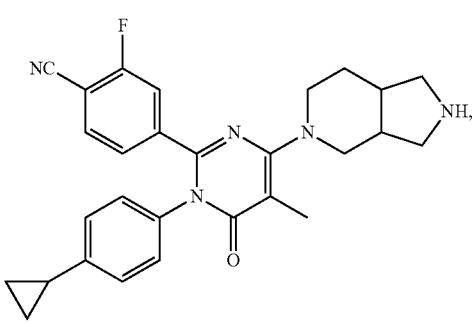
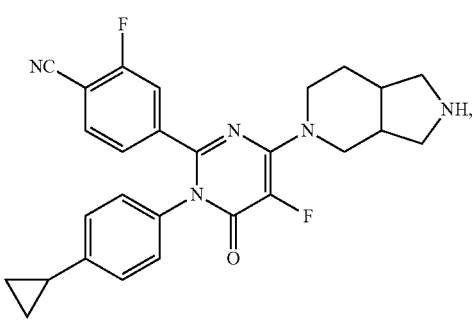

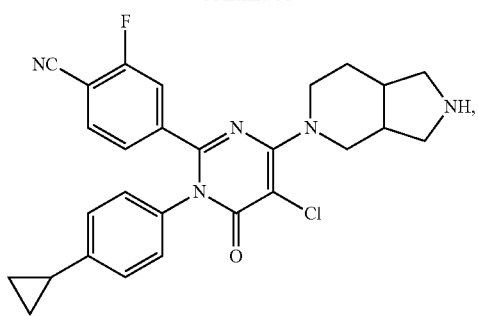
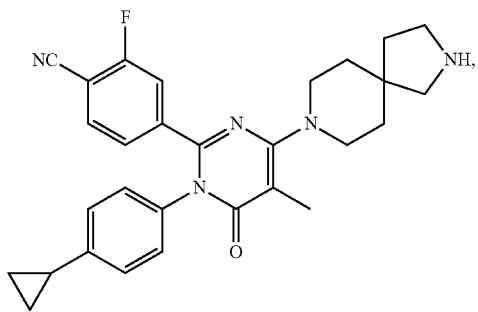
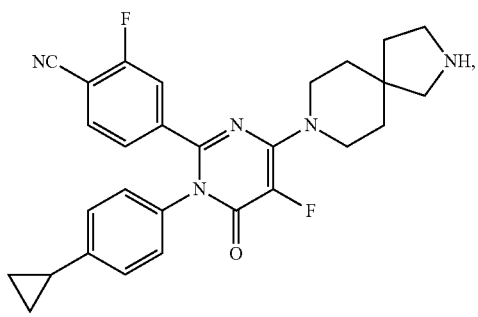
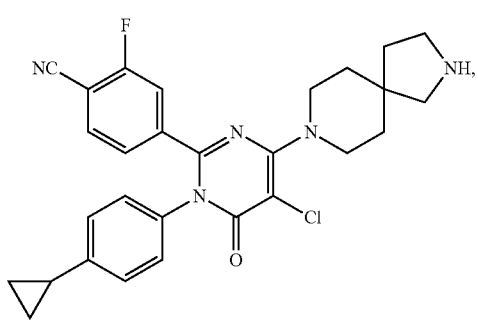
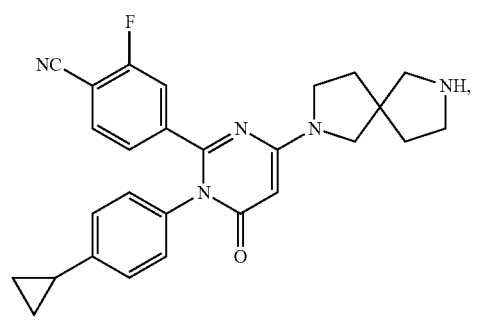
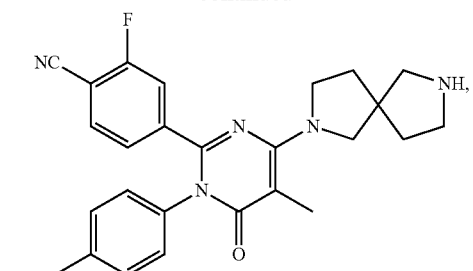
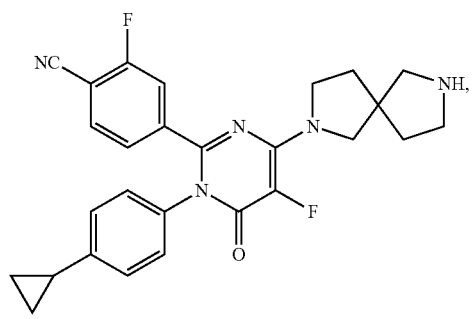
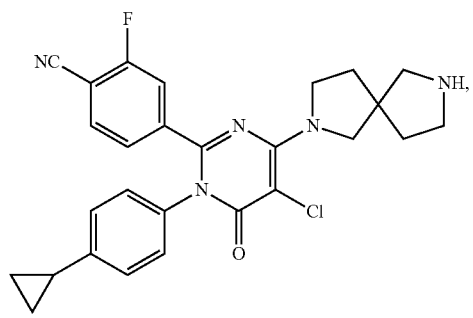
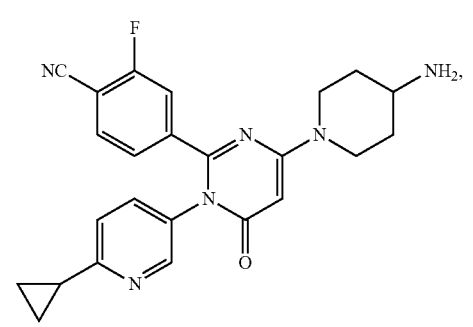
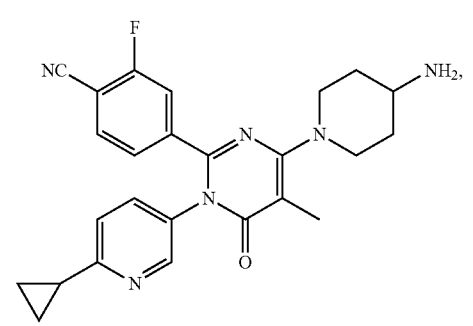

111
-continued
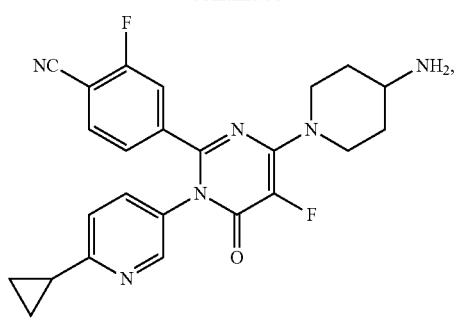
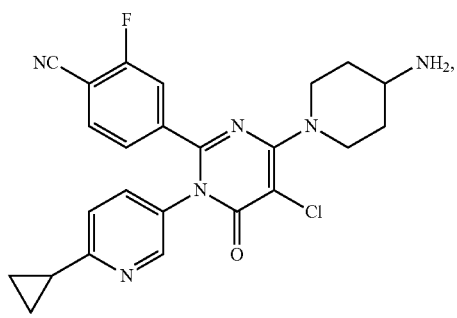
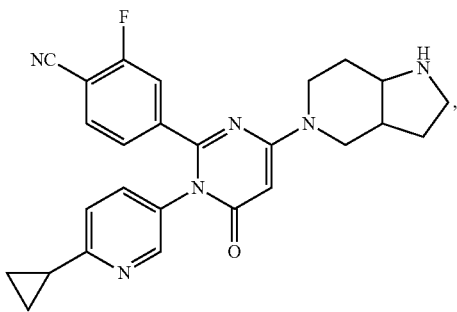
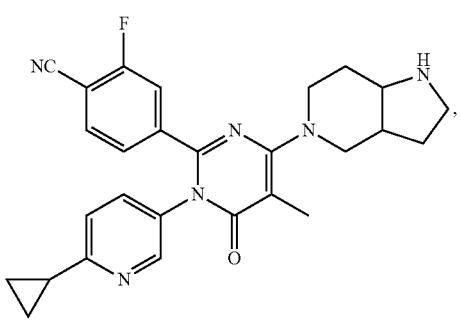
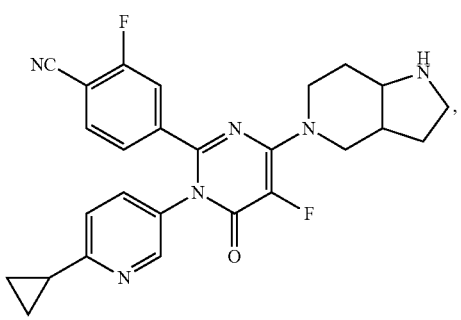
112
-continued
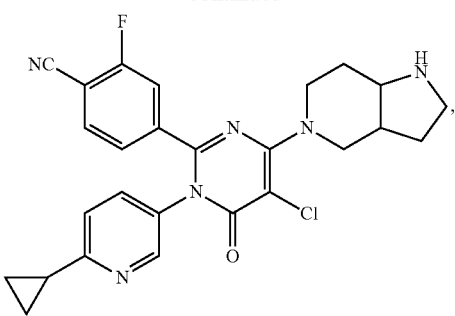
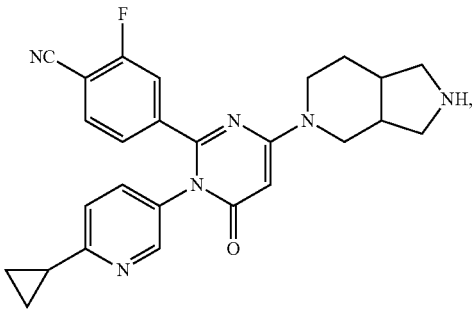
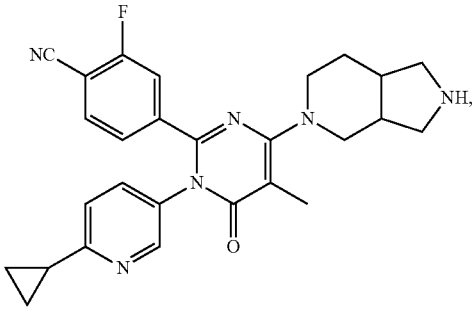
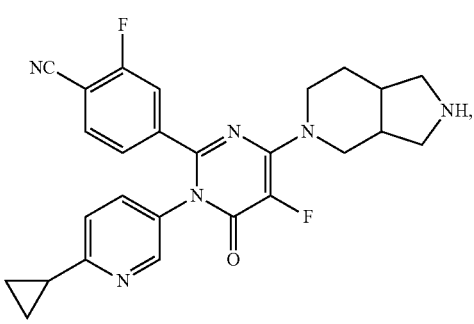
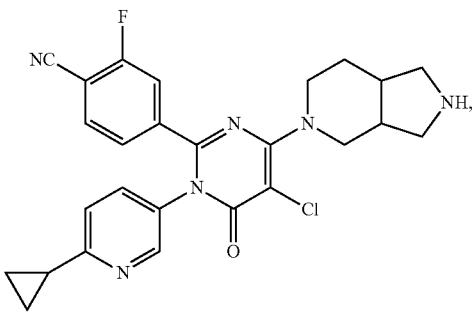

-continued
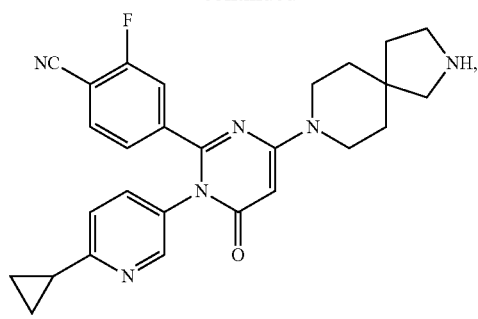
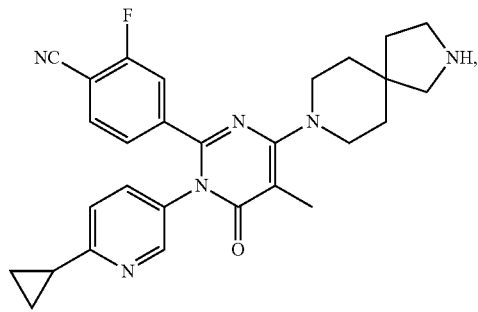
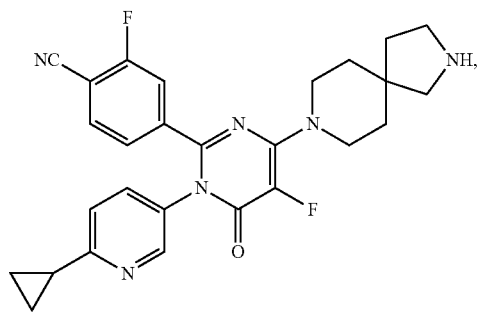
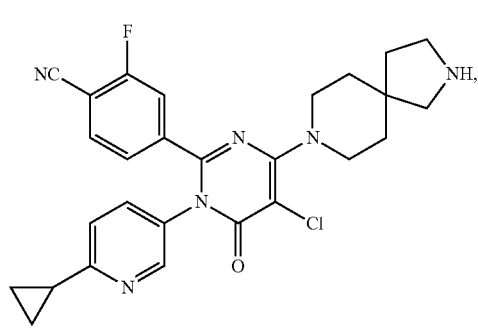
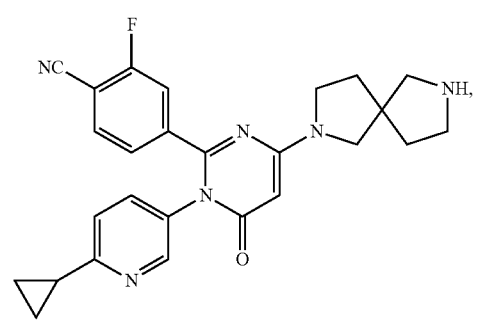
-continued
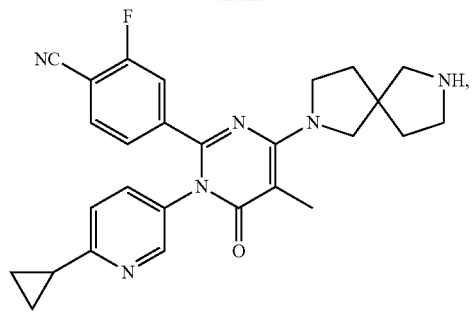
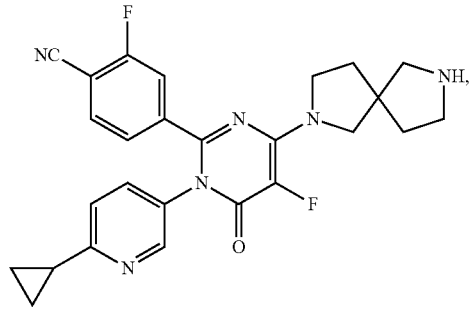
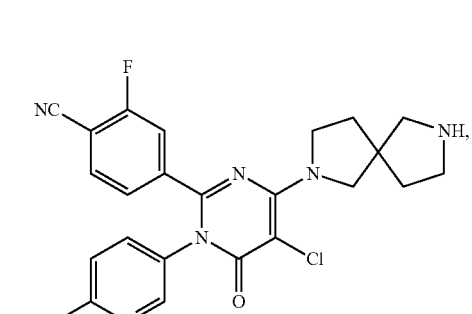
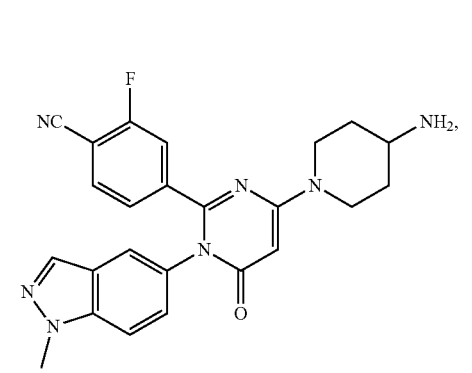
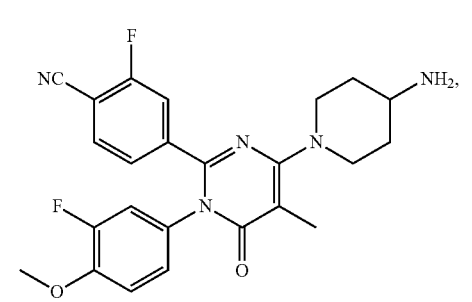

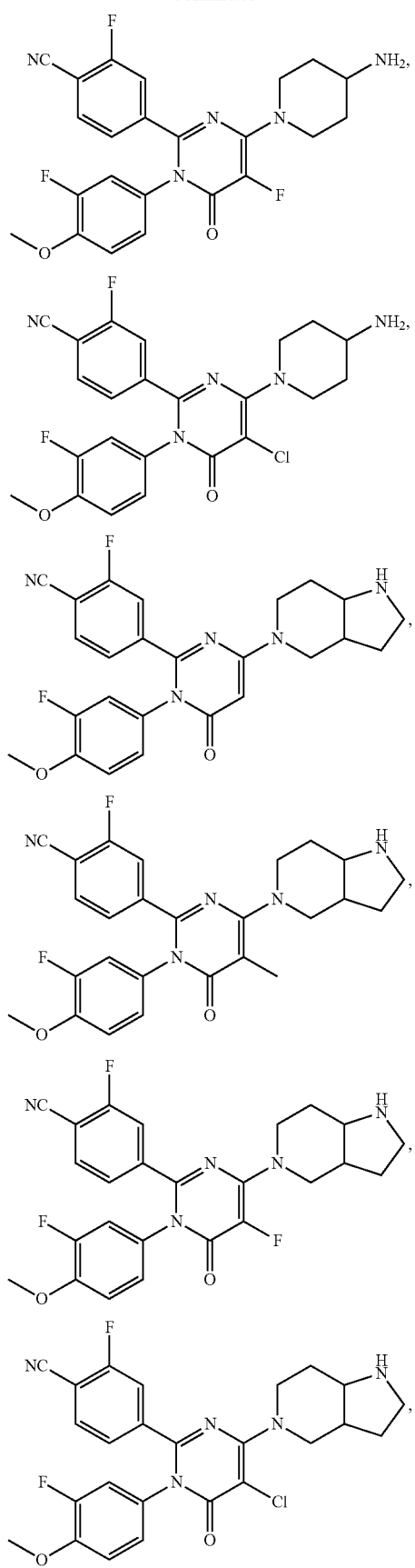
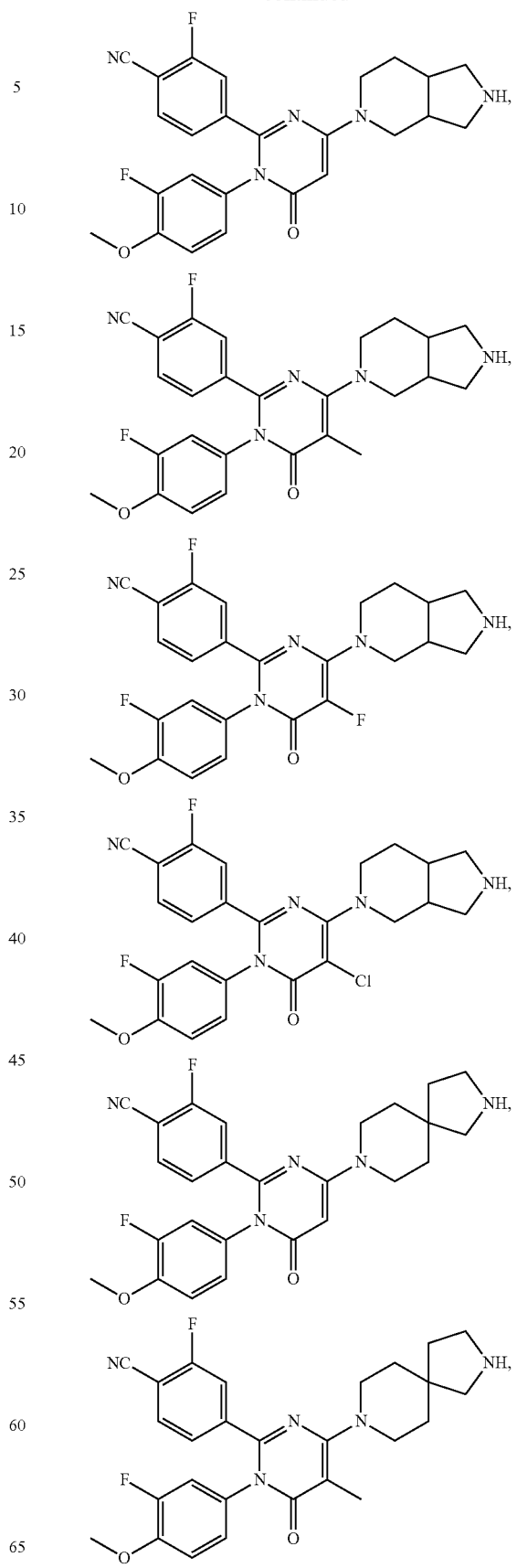

117
-continued
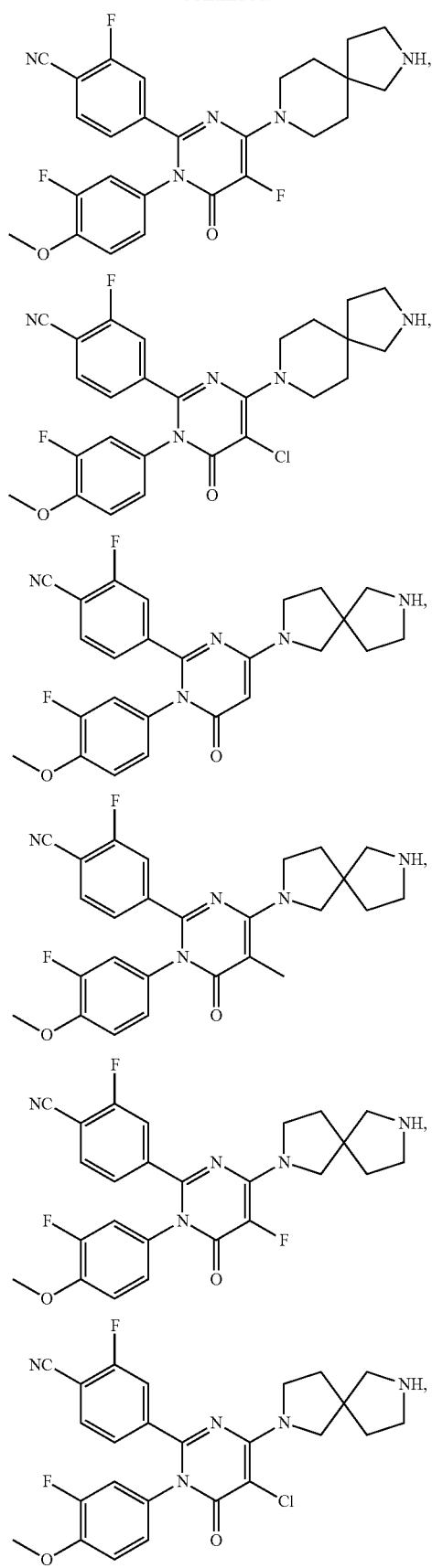
118
-continued
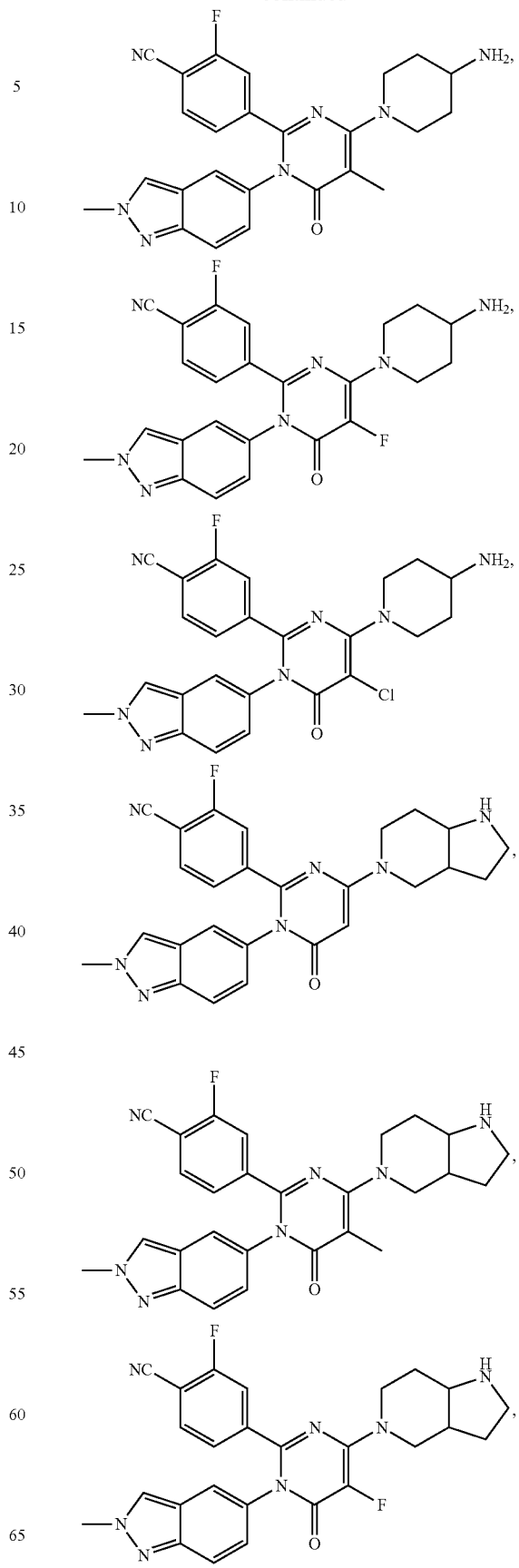

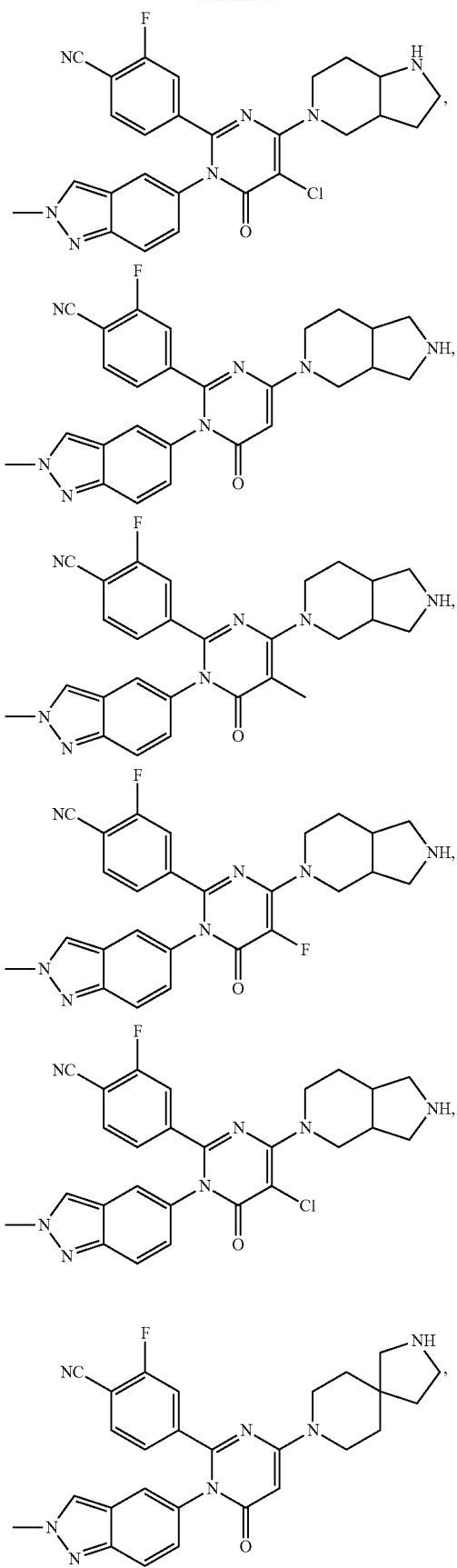
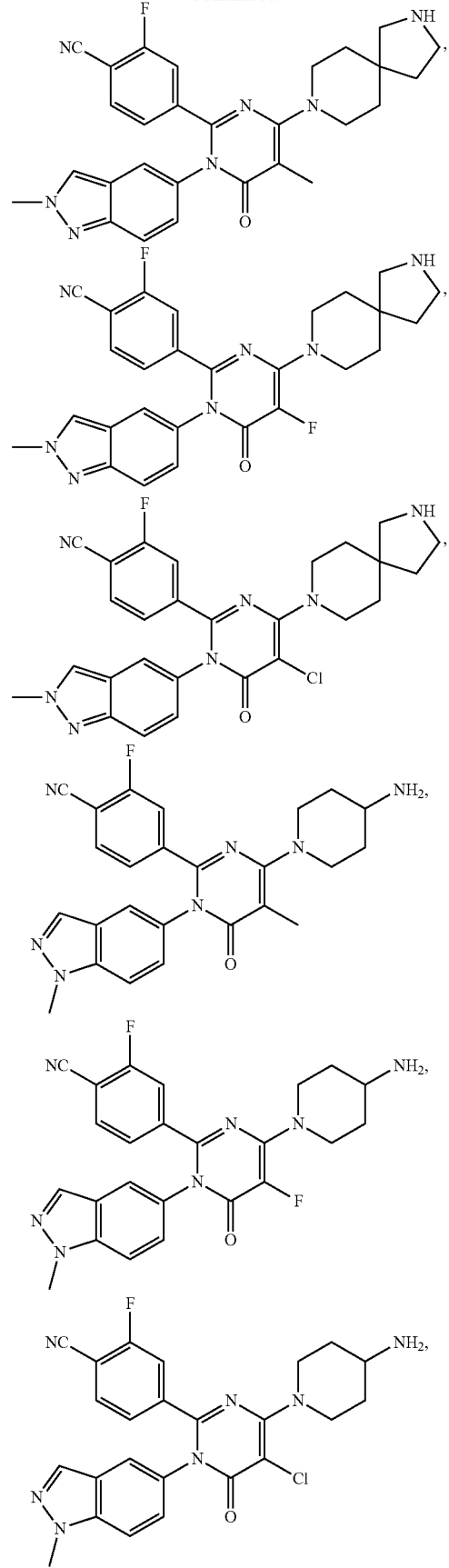

121
-continued
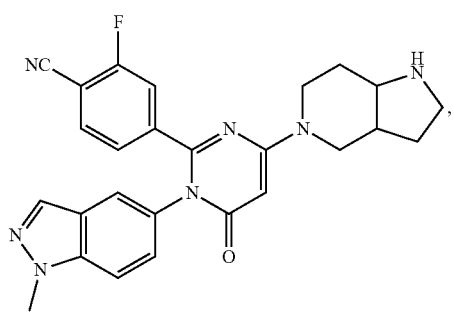
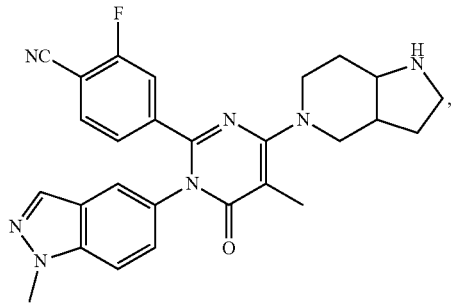
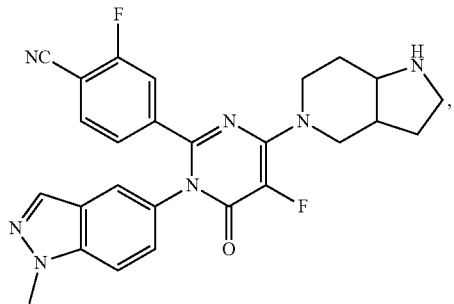
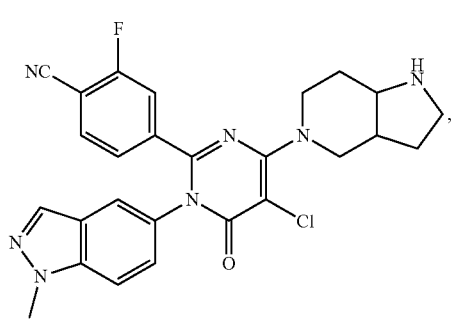
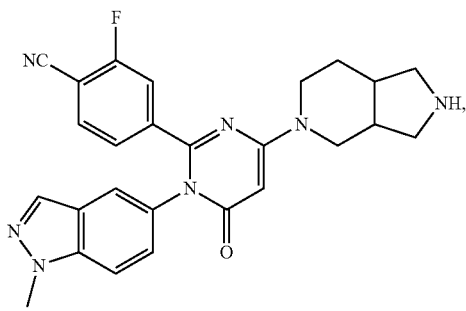
122
-continued
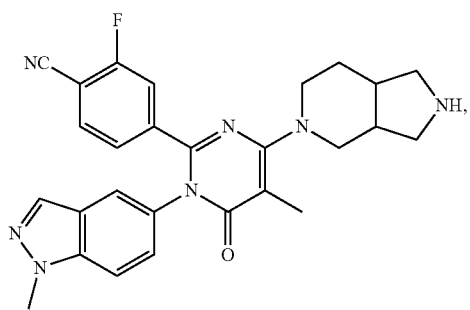
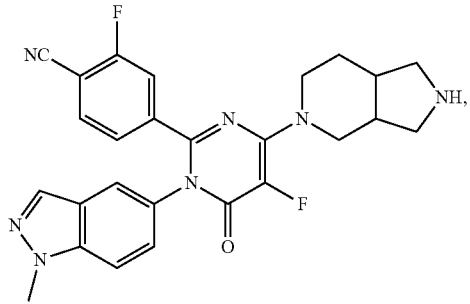
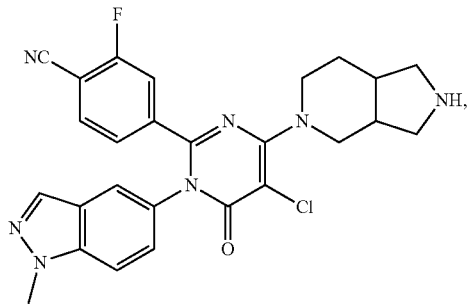
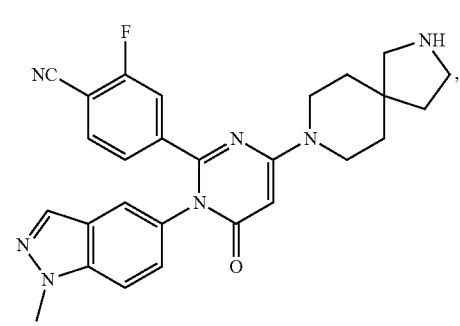
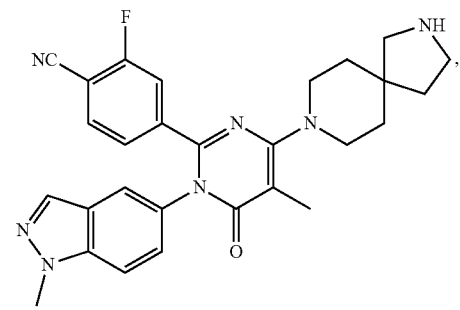

123
-continued
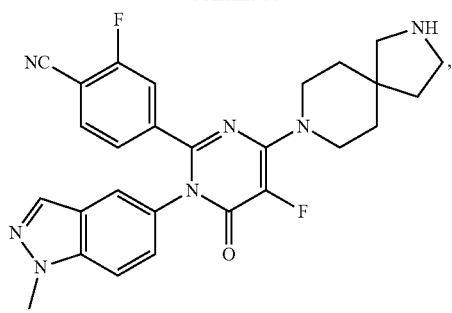
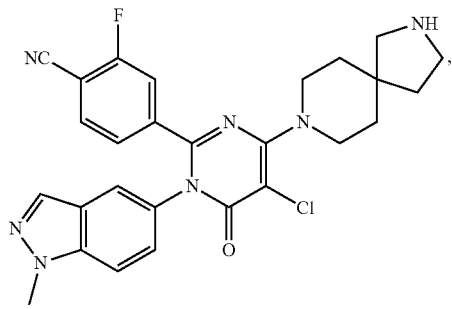
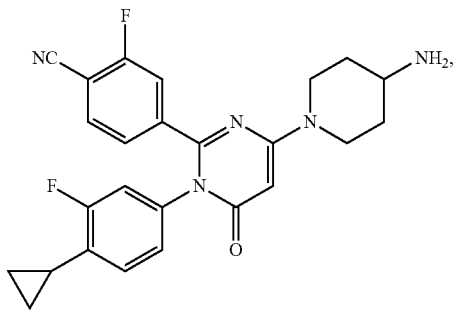
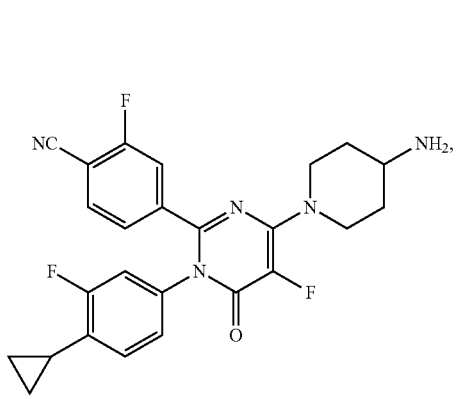
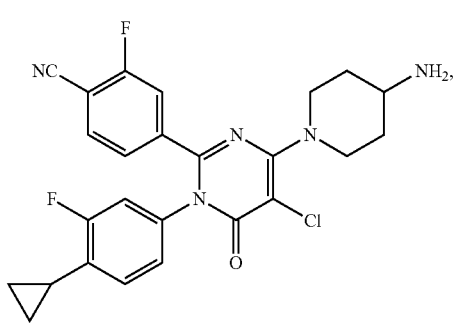
124
-continued
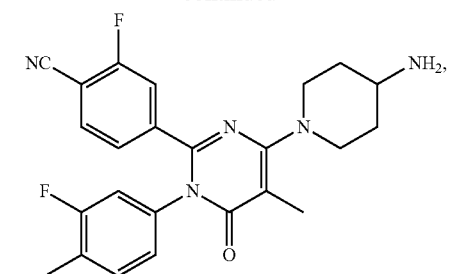
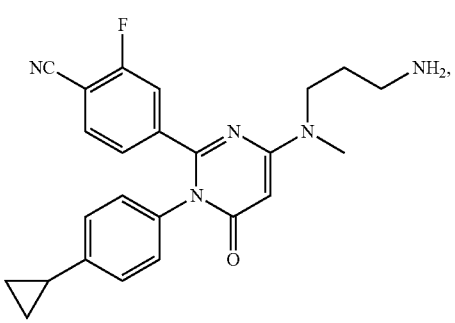
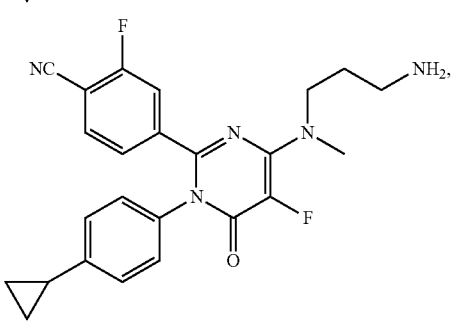
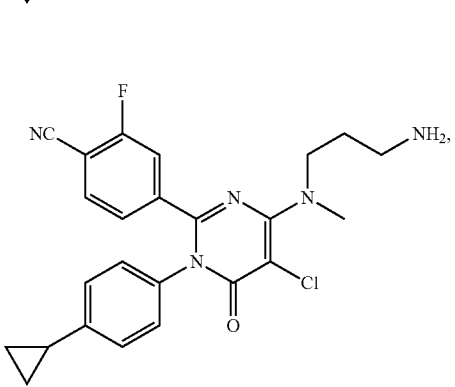
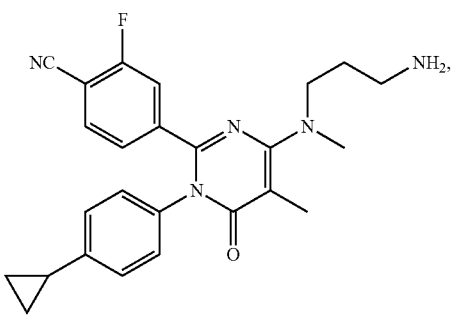

125
-continued
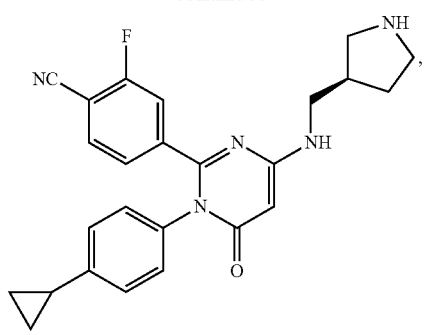
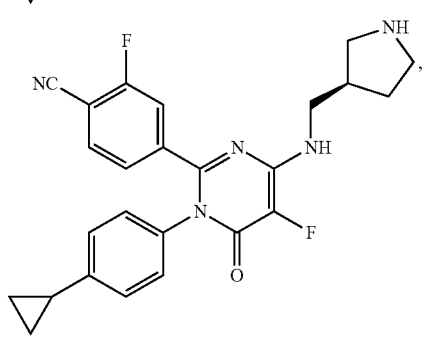
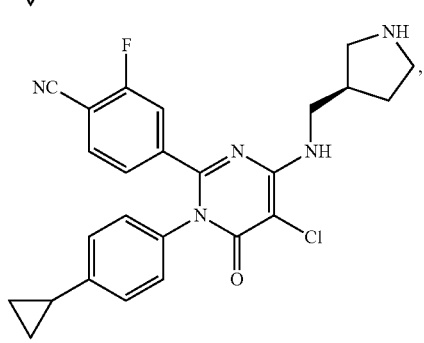
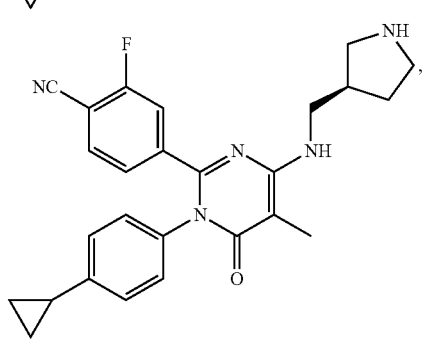
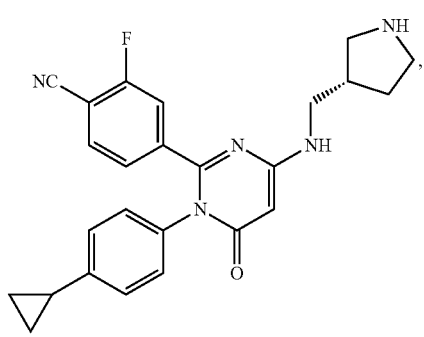
126
-continued
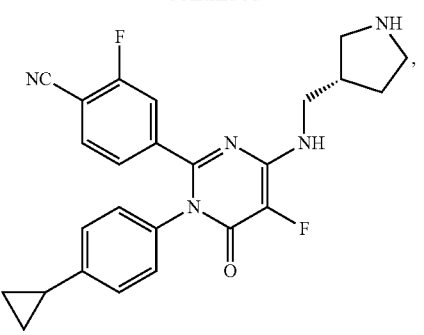
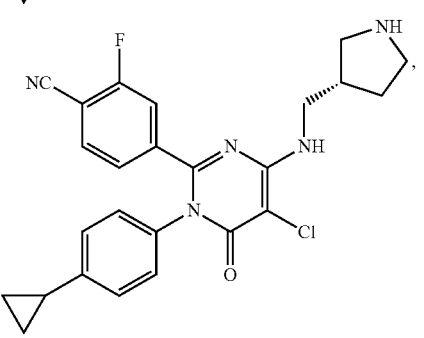
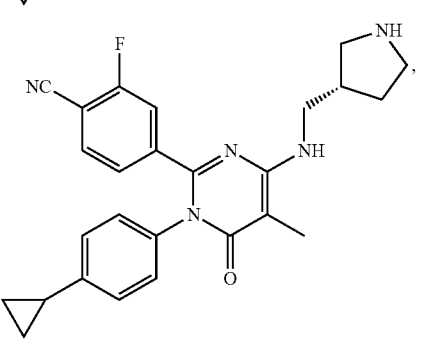
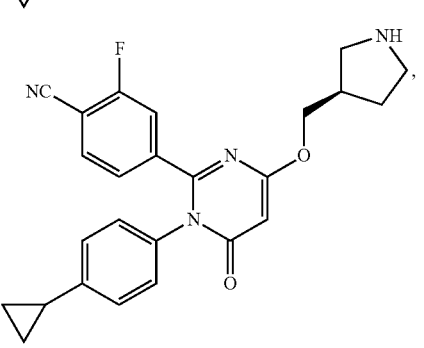

127
-continued
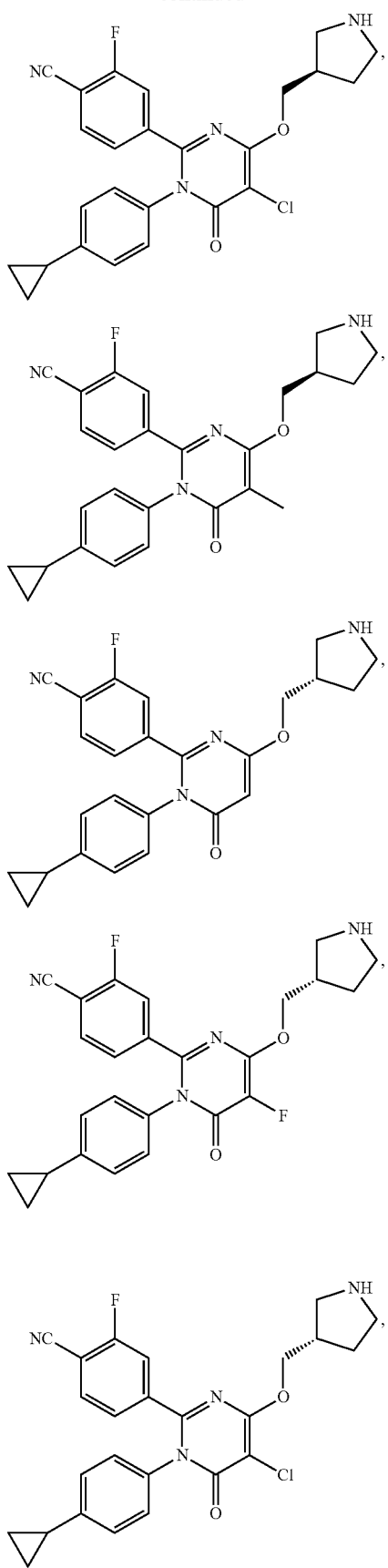
128
-continued
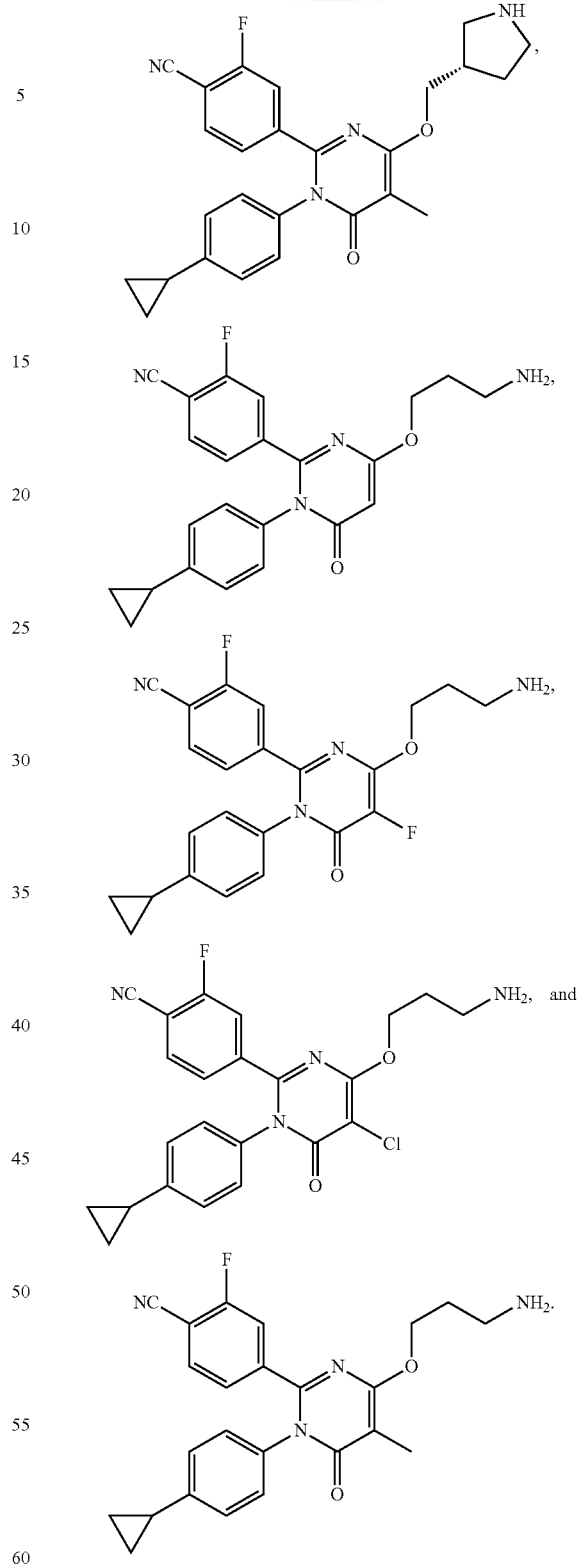
6. A pharmaceutical composition comprising the compound of claim 5 or a pharmaceutical acceptable salt thereof and a pharmaceutical acceptable carrier.
7. A method for therapeutically treating acute myeloid leukemia, breast or prostate cancer in a patient in need thereof, comprising administering to the patient the pharmaceutical composition of claim 6.

8. A method of modulating gene transcription in a cell comprising inhibiting lysine-specific demethylase 1 activity by contacting the lysine-specific demethylase 1 enzyme with the compound of claim 5.

* * * * *